US008937110B2

(12) United States Patent
Alli et al.

(10) Patent No.: US 8,937,110 B2
(45) Date of Patent: Jan. 20, 2015

(54) SILICONE HYDROGELS HAVING A STRUCTURE FORMED VIA CONTROLLED REACTION KINETICS

(71) Applicant: Johnson & Johnson Vision Care, Inc., Jacksonville, FL (US)

(72) Inventors: Azaam Alli, Jacksonville, FL (US); Douglas G. Vanderlaan, Jacksonville, FL (US); James D. Ford, Orange Park, FL (US); Scott L. Joslin, Ponte Vedra Beach, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/720,218

(22) Filed: Dec. 19, 2012

(65) Prior Publication Data
US 2014/0031447 A1   Jan. 30, 2014

Related U.S. Application Data

(60) Provisional application No. 61/579,683, filed on Dec. 23, 2011.

(51) Int. Cl.
| *C08G 61/12* | (2006.01) |
| *C08F 2/46* | (2006.01) |
| *C08G 61/04* | (2006.01) |
| *C09D 4/00* | (2006.01) |
| *C08F 20/36* | (2006.01) |
| *C08F 2/50* | (2006.01) |
| *B29C 59/16* | (2006.01) |
| *G02C 7/02* | (2006.01) |
| *G02C 7/04* | (2006.01) |
| *A61F 2/14* | (2006.01) |

(52) U.S. Cl.
CPC . *C09D 4/00* (2013.01); *C08F 20/36* (2013.01); *C08F 2/46* (2013.01); *C08F 2/50* (2013.01); *B29C 59/16* (2013.01); *G02C 7/02* (2013.01); *G02C 7/04* (2013.01); *A61F 2/14* (2013.01)
USPC .................. 522/167; 522/1; 520/1

(58) Field of Classification Search
CPC ............ C09D 4/00; C08F 20/36; C08F 2/46; C08F 2/50; C03F 7/027; B29C 59/16; C03G 5/062; G02C 7/02; G02C 7/04; A61F 2/14
USPC .......................... 522/167, 1; 520/1
See application file for complete search history.

(56) References Cited

U.S. PATENT DOCUMENTS

| 3,408,429 | A | 10/1968 | Wichterle |
| 3,660,545 | A | 5/1972 | Wichterle |
| 4,113,224 | A | 9/1978 | Clark |
| 4,136,250 | A | 1/1979 | Mueller |
| 4,139,513 | A | 2/1979 | Tanaka |
| 4,153,641 | A | 5/1979 | Deichert |
| 4,197,266 | A | 4/1980 | Clark |
| 4,246,389 | A | 1/1981 | LeBoeuf |
| 4,260,725 | A | 4/1981 | Keogh |
| 4,495,313 | A | * 1/1985 | Larsen ............... 523/106 |
| 4,810,764 | A | 3/1989 | Friends et al. |
| 4,837,289 | A | 6/1989 | Mueller et al. |
| 5,314,961 | A | 5/1994 | Anton et al. |
| 5,358,995 | A | 10/1994 | Lai et al. |
| 5,387,662 | A | 2/1995 | Kunzler et al. |
| 5,486,579 | A | 1/1996 | Lai et al. |
| 5,712,327 | A | 1/1998 | Chang et al. |
| 5,998,498 | A | 12/1999 | Vanderlaan et al. |
| 6,020,445 | A | * 2/2000 | Vanderlaan et al. ......... 526/279 |
| 6,367,929 | B1 | 4/2002 | Maiden et al. |
| 6,602,930 | B2 | 8/2003 | Imafuku |
| 6,762,264 | B2 | 7/2004 | Kunzler et al. |
| 6,867,245 | B2 | 3/2005 | Iwata |
| 6,943,203 | B2 | 9/2005 | Vanderlaan |
| 7,722,808 | B2 | 5/2010 | Matsuzawa et al. |
| 7,934,830 | B2 | 5/2011 | Blackwell et al. |
| 8,367,746 | B2 | 2/2013 | Manesis et al. |
| 2001/0044482 | A1* | 11/2001 | Hu et al. ................... 523/106 |
| 2002/0016383 | A1 | 2/2002 | Iwata |
| 2002/0107324 | A1 | 8/2002 | Vanderlaan et al. |
| 2004/0039077 | A1 | 2/2004 | Baba et al. |
| 2006/0063852 | A1 | 3/2006 | Iwata et al. |
| 2006/0187410 | A1 | 8/2006 | Sato et al. |

(Continued)

FOREIGN PATENT DOCUMENTS

| WO | 03022321 A2 | 3/2003 |
| WO | 03022322 A2 | 3/2003 |

(Continued)

OTHER PUBLICATIONS

PCT International Search Report, dated Mar. 18, 2013, for PCT Int'l Appln. No. PCT/US2012/070879.
Barton, CRC Handbook of Solubility Par., 1st. Ed. 1983, p. 85-87 and using Tables 13, 14.
Crivello, et al, vol. III, Photoinitiators for Free Radical Cationic & Anionic Photopolymerization, 2nd Edition; edited by G. Bradley; John Wiley and Sons; New York; 1998.

(Continued)

*Primary Examiner* — Ling Choi
*Assistant Examiner* — Jessica E Whiteley
(74) *Attorney, Agent, or Firm* — Karen A. Harding

(57) ABSTRACT

The present invention relates to a process comprising the steps of reacting a reactive mixture comprising at least one silicone-containing component, at least one hydrophilic component, and at least one diluent to form an ophthalmic device having an advancing contact angle of less than about 80°; and contacting the ophthalmic device with an aqueous extraction solution at an elevated extraction temperature, wherein said at least one diluent has a boiling point at least about 10° higher than said extraction temperature.

76 Claims, 7 Drawing Sheets

(56) References Cited

U.S. PATENT DOCUMENTS

| | | |
|---|---|---|
| 2006/0229423 A1 | 10/2006 | Parakka et al. |
| 2007/0066706 A1 | 3/2007 | Manesis et al. |
| 2009/0060981 A1 | 3/2009 | Chauhan |
| 2010/0048847 A1 | 2/2010 | Broad |
| 2010/0249356 A1 | 9/2010 | Rathore |
| 2010/0280146 A1 | 11/2010 | Vanderlaan |
| 2011/0046332 A1 | 2/2011 | Breiner et al. |
| 2011/0230589 A1 | 9/2011 | Maggio |
| 2011/0237766 A1 | 9/2011 | Maggio |
| 2012/0214899 A1 | 8/2012 | Lee et al. |
| 2012/0216488 A1 | 8/2012 | Liu et al. |
| 2012/0216489 A1 | 8/2012 | Lee et al. |
| 2012/0218509 A1 | 8/2012 | Back et al. |
| 2012/0219387 A1 | 8/2012 | Atkinson et al. |
| 2012/0220688 A1 | 8/2012 | Wang et al. |
| 2012/0220689 A1 | 8/2012 | Yao et al. |
| 2012/0220743 A1 | 8/2012 | Francis et al. |
| 2012/0220744 A1 | 8/2012 | Liu et al. |

FOREIGN PATENT DOCUMENTS

| | | | |
|---|---|---|---|
| WO | 2008116131 A2 | | 9/2008 |
| WO | 2009/058207 | * | 5/2009 |
| WO | 2012118677 A1 | | 9/2012 |
| WO | 2012118683 A1 | | 9/2012 |

OTHER PUBLICATIONS

Lai et al, "The role of ionic hydrophilic monomers in silicone hydrogels for contact lens application", G.; 213$^{th}$ ACS National Meeting, San Francisco, Apr. 13-17, 1997.

Moad et al, The Chemistry of Radical Polymerization, 2nd ed., pp. 472-479, 488-489, 492-497, 508-514, 2006.

International Preliminary Report on Patentability, dated Jun. 24, 2014 for PCT Int'l Appln. No. PCT/US2012/070879.

PCT International Search Report, dated Apr. 18, 2013, for PCT Int'l Appln. No. PCT/US2012/070890.

PCT International Search Report, dated Mar. 19, 2013, for PCT Int'l Appln. No. PCT/US2012/070895.

PCT International Preliminary Report on Patentability, dated Jun. 24, 2014, for PCT Int'l Appln. No. PCT/US2012/070890.

PCT International Preliminary Report on Patentability, dated Jun. 24, 2014, for PCT Int'l Appln. No. PCT/US2012/070895.

PCT International Preliminary Report on Patentability, dated Jun. 24, 2014, for PCT Int'l Appln. No. PCT/US2012/070899.

PCT International Preliminary Report on Patentability, dated Jun. 24, 2014, for PCT Int'l Appln. No. PCT/US2012/070906.

PCT International Search Report, dated Mar. 22, 2013, for PCT Int'l Appln. No. PCT/US2012/070906.

PCT International Search Report, dated May 13, 2013, for PCT Int'l Appln. No. PCT/US2012/070899.

* cited by examiner

SILICONE HYDROGELS HAVING A STRUCTURE FORMED VIA CONTROLLED REACTION KINETICS

RELATED APPLICATIONS

This application claims priority to U.S. Provisional Patent Application No. 61/579,683, filed on Dec. 23, 2011 entitled SILICONE HYDROGELS HAVING A STRUCTURE FORMED VIA CONTROLLED REACTION KINETICS, the contents of which are incorporated by reference.

FIELD OF THE INVENTION

The present invention relates to silicone hydrogels having an exceptional balance of properties which are generated by controlling the reaction kinetics of the components of the reaction mixture.

BACKGROUND OF THE INVENTION

Soft contact lenses made from silicone hydrogels offer improved oxygen permeability as compared to soft lenses made from non-silicone materials such as poly(2-hydroxyethyl methacrylate) (HEMA). Initial efforts to make silicone hydrogel contact lenses were hampered by the poor wettability, high modulus, poor clarity, hydrolytic instability or the high cost of raw materials used to make many of these silicone hydrogels. While various solutions have proven somewhat successful for each of these deficiencies, there remains a need for silicone hydrogels that can be made from inexpensive commercially available monomers, and which have excellent wettability (without the need for surface modification), low modulus, good clarity, and desirable oxygen permeability.

Silicone hydrogels formulations containing polymeric wetting agents, such as poly(N-vinylpyrrolidone) (PVP) and acyclic polyamides have been disclosed. However, these polymers are quite large and require the use of special compatibilizing components, which need to be custom manufactured. Examples of compatibilizing components include 2-propenoic acid, 2-methyl-,2-hydroxy-3-[3-[1,3,3,3-tetramethyl-1-[(trimethylsilyl)oxy]disiloxanyl]propoxy]propyl ester (SiGMA).

An alternative means of forming a wettable silicone hydrogel lens is to incorporate monomeric N-vinylpyrrolidone (NVP) into the monomer mix used to make the silicone hydrogel polymer, typically in amounts of about 25-55% (by weight) of the monomer mix. Such materials have been described in U.S. Pat. Nos. 4,136,250; 4,153,641; 4,260,725 and 6,867,245. The materials described in these references generally incorporate polyfunctional silicone monomers or macromers, that act as crosslinking agents, and thereby increase the modulus of the final polymer. U.S. Pat. No. 4,139,513 discloses that 2-propenoic acid, 2-methyl-,2-hydroxy-3-[3-[1,3,3,3-tetramethyl-1-[(trimethylsilyl)oxy]disiloxanyl]propoxy]propyl ester (SiGMA) can be used to form lenses from formulations comprising NVP and HEMA. SiGMA is the only source of silicone disclosed. However, because of the relatively low silicone content in those monomers, desirable levels of oxygen permeability in the final polymers are difficult to achieve.

US 2010/0048847 discloses silicone hydrogels made from a blend of a monomethacryloxyalkyl polydimethylsiloxane methacrylate with about 52% NVP, HEMA and TRIS, and using a blend of ethanol and ethyl acetate as a diluent. The polymers disclosed are (to varying degrees) hazy, but it was disclosed in this application that the haziness could be reduced by the addition of at least about 1.5% methacrylic acid (MAA).

Addition of anionic monomers such as MAA can, however, cause hydrolytic instability in silicone hydrogels, as was disclosed in "The role of ionic hydrophilic monomers in silicone hydrogels for contact lens application", Lai, Y., Valint, P., and Friends, G.; 213th ACS National Meeting, San Francisco, Apr. 13-17, 1997. For this reason, it remains desirable to form clear, hydrolytically stable, wettable (without surface treatment) silicone hydrogels with low moduli from a combination of a monomethacryloxyalkyl polydimethylsiloxane methacrylate such as mPDMS, and NVP.

SUMMARY OF THE INVENTION

The present invention relates to silicone hydrogels formed from a reaction mixture comprising, consisting or consisting essentially of about 25 to about 75 wt % of at least one slow reacting reactive hydrophilic component having a hydrophilic component kinetic half life;

at least one reactive silicone-containing component having a silicone-containing component kinetic half life; and at least one light-initiated initiator; wherein at least one of said components comprises at least one hydroxyl group and wherein ratio of said hydrophilic component half life to said silicone-containing component half life is at least 2.

The present invention further relates to silicone hydrogels formed from a reaction mixture comprising, consisting or consisting essentially of about 39 to about 75 wt % of at least one slow-reacting hydrophilic monomer;

at least one silicone-containing component; and at least one photoinitiator;

wherein at least one of said silicone-containing component, optional additional hydrophilic components or both comprises at least one hydroxyl group and wherein said slow-reacting hydrophilic component and said silicone-containing component are selected to have a conversion ratio at 90% conversion of at least about 20.

The present invention further relates to a process for forming a silicone hydrogel comprising photocuring a reaction mixture comprising, consisting or consisting essentially of about 39 to about 75 wt % of at least one slow-reacting hydrophilic monomer;

at least one silicone-containing component; and at least one photoinitiator;

wherein said photocuring is completed in about 30 minutes or less and at least one of said silicone-containing component, optional additional hydrophilic components or both comprises at least one hydroxyl group.

The present invention further relates to a process for forming a silicone hydrogel comprising, consisting or consisting essentially of photocuring via ebeam irradiation, a reaction mixture comprising about 39 to about 75 wt % of at least one slow-reacting hydrophilic monomer;

at least one silicone-containing component; and at least one photoinitiator;

wherein at least one of said silicone-containing component, optional additional hydrophilic components or both comprises at least one hydroxyl group.

The silicone hydrogels of the present invention are useful for making biomedical devices, ophthalmic devices, and particularly contact lenses.

DETAILED DESCRIPTION OF THE INVENTION

Figure 1:
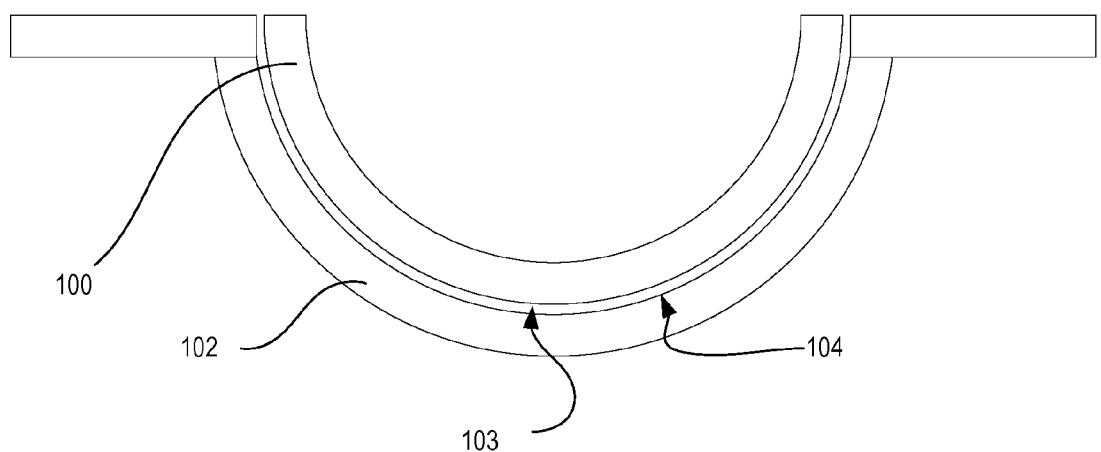
FIG. 1 is a schematic of a lens assembly.

The present invention relates to silicone hydrogels formed from reaction mixtures comprising at least one hydrophilic component which has a kinetic half life which is at least twice as long as the kinetic half life of the slowest silicone containing composition. At least one component of the reaction mixture comprises at least one hydroxyl group. The resulting silicone hydrogels are surprisingly easy to process and display an exceptional balance of properties including haze, water content and oxygen permeability.

As used herein, "diluent" refers to a non-reactive solvent for the reactive components. Diluents do not react to form part of the biomedical devices.

As used herein, a "biomedical device" is any article that is designed to be used while either in or on mammalian tissues or fluid, and in one embodiment in or on human tissue or fluids. Examples of these devices include but are not limited to catheters, implants, stents, and ophthalmic devices such as intraocular lenses, punctal plugs and contact lenses. For example, the biomedical devices are ophthalmic devices, particularly contact lenses, most particularly contact lenses made from silicone hydrogels.

As used herein, the terms "ophthalmic device" refers to products that reside in or on the eye. As used herein, the terms "lens" and "ophthalmic device" refer to devices that reside in or on the eye. These devices can provide optical correction, wound care, drug delivery, diagnostic functionality, cosmetic enhancement or effect, glare reduction, UV blocking or a combination of these properties. Non-limiting examples of ophthalmic devices include lenses, punctal plugs and the like. The term lens (or contact lens) includes but is not limited to soft contact lenses, hard contact lenses, intraocular lenses, overlay lenses, ocular inserts, and optical inserts.

As used herein "reaction mixture" refers to reactive and non-reactive components (including the diluent) that are mixed together and reacted to form the silicone hydrogels of the present invention. The reactive components are everything in the reaction mixture except the diluent and any additional processing aids which do not become part of the structure of the polymer.

As used herein "(meth)" refers to an optional methyl substitution. Thus, a term such as "(meth)acrylate" denotes both methacrylic and acrylic radicals.

All percentages in this specification are weight percentages unless otherwise noted.

As used herein, the phrase "without a surface treatment" or "not surface treated" means that the exterior surfaces of the devices of the present invention are not separately treated to improve the wettability of the device. Treatments which may be foregone because of the present invention include, plasma treatments, grafting, coating and the like. Coatings which provide properties other than improved wettability, such as, but not limited to antimicrobial coatings and the application of color or other cosmetic enhancement, are not considered surface treatment.

As used herein "silicone macromers" and silicone "prepolymers" mean mono- and multi-functional silicone containing compounds having molecular weights of greater than about 2000.

As used herein "hydroxyl-containing component" is any component containing at least one hydroxyl group.

As used herein "kinetic half life" means the time elapsed at the given reaction conditions for 50% of the reactive component to be consumed. It should be appreciated that the kinetic half life for a given component will be influenced by the other reaction mixture components, as well as the cure conditions selected, as is described in detail herein. Kinetic half life is calculated as described in the examples.

The kinetic half life ratios calculated herein must be calculated using the kinetic half lives measured from that particular reaction mixture and cure conditions.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. Non-limiting examples of the free radical reactive groups include (meth)acrylate, acryloxy, (meth)acrylamide, and mixtures thereof.

It has been surprisingly found that by selecting the components of the reaction mixture, silicone hydrogels having a desirable balance of properties may be formed. The reaction mixtures of the present invention comprise about 25 to about 75 wt %, about 30 to about 75 wt %, between about 37 and about 75 wt %; between about 39 and about 70 wt %; and between about 39 and about 60 wt % of at least one slow-reacting hydrophilic monomer;

at least one reactive silicone-containing component;

at least one photoinitiator; and at least one crosslinker which has a kinetic half life which is not slower than the kinetic half life of the fastest reacting silicone containing component. The slowest reacting silicone-containing component has a kinetic half life which is at least half the kinetic half life of the slow-reacting hydrophilic monomer. At least one of said components comprises at least one hydroxyl group. The at least one component may be a hydroxyalkyl(meth)acrylate or hydroxyalkyl(meth)acrylamide.

In the present invention the components are selected to react at specific points in the reaction. For example, "fast reacting" components are selected to polymerize primarily at the beginning of the overall copolymerization reaction, while the slow reacting hydrophilic monomer is selected to polymerize primarily at the end of the overall copolymerization reaction. Fast reacting components include the silicone-containing components, the hydroxyalkyl monomers and some crosslinkers. In one embodiment slow reacting components have kinetic half lives which are at least about two times greater than the fastest silicone containing monomer. Kinetic half lives may be measured as described herein. It should be appreciated that the kinetic half lives are relative to specific formulations.

Examples of slow reacting groups include (meth)acrylamides, vinyls, allyls and combinations thereof and a least one hydrophilic group. Non-limiting examples of the slow reacting group include N-vinyl amides, O-vinyl carbamates, O-vinyl carbonates, N-vinyl carbamates, O-vinyl ethers, O-2-propenyl, wherein the vinyl or allyl groups may be further substituted with a methyl group. The slow reacting group may be selected from N-vinyl amides, O-vinyl carbonates, and O-vinyl carbamates.

Examples of fast reacting groups include (meth)acrylates, styryls, (meth)acryamides and mixtures thereof. Generally (meth)acrylates are faster than (meth)acrylamides, and acrylamides are faster than (meth)acrylamides.

Throughout the specification, wherever chemical structures are given, it should be appreciated that alternatives disclosed for the substituents on the structure may be combined in any combination. Thus if a structure contained substituents $R_1$ and $R_2$, each of which contained three lists of potential groups, 9 combinations are disclosed. The same applies for combinations of properties.

The first component of the reactive mixture is at least one slow-reacting hydrophilic monomer. The slow-reacting hydrophilic monomer comprises a slow reacting group and at least one hydrophilic group including hydroxyls, amines, ethers, amides, ammonium groups, carboxylic acid, carbamates, combinations thereof and the like. Suitable hydrophilic groups include hydroxyls, ethers, amides, carboxylic acid combinations thereof and the like.

If a (meth)acrylamide is selected as the slow-reacting hydrophilic monomer, a silicone-containing monomer having a very short kinetic half life, such as an acrylate must be used. Methacrylamides are generally slower reacting that acrylamides, and bulky (meth)acrylamides are slower than smaller (meth)acrylamides. Examples of a suitable (meth) acrylamide include bis-(2-hydroxyethyl) methacrylamide, 2,3-dihydroxypropyl methacrylamide, N-[3-(Dimethylamino)propyl]methacrylamide, N-[tris(hydroxymethyl)methyl]acrylamide and methacrylamides substituted with one or two polyethylene glycol chains having 2-10, 2-5 repeating units and the like. Where a methacrylamide is used as the slow-reacting hydrophilic monomer, very fast silicone containing monomer, such as silicone acrylates should be used to provide the desired difference in kinetic half lives. For example, N-[3-(Dimethylamino)propyl]methacrylamide may be used as the slow-reacting hydrophilic monomer with silicone acrylates.

In another embodiment the slow-reacting hydrophilic monomer is selected from N-vinylamide monomer of Formula I, a vinyl pyrrolidone of Formula II-IV, n-vinyl piperidone of Formula V:

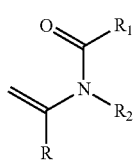

Formula I

-continued

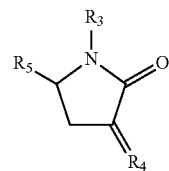

Formula II

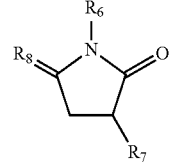

Formula III

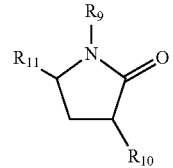

Formula IV

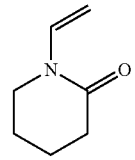

Formula V wherein R is H or methyl, and in one embodiment R is H;
$R_1, R_2, R_3, R_6, R_7, R_{10}$, and $R_{11}$ are independently selected from H, $CH_3$, $CH_2CH_3$, $CH_2CH_2CH_3$, $C(CH_3)_2$;
$R_4$ and $R_8$ are independently selected from $CH_2$, $CHCH_3$ and $—C(CH_3)$;
$R_5$ is selected from H, methyl, ethyl; and
$R_9$ is selected from $CH=CH_2$, $CCH_3=CH_2$, and $CH=CHCH_3$.

In one embodiment the total number of carbon atoms in $R_1$ and $R_2$ is 4 or less, and in another embodiment $R_1$ and $R_2$ are methyl.

In another embodiment the slow-reacting hydrophilic monomer is selected from the N-vinyl amide monomer of Formula I or a vinyl pyrrolidone of Formula II or IV. In yet another embodiment $R_6$ is methyl, $R_7$ is hydrogen, $R_9$ is $CH=CH_2$, $R_{10}$ and $R_{11}$ are H.

In another embodiment the slow-reacting hydrophilic monomer is selected from ethylene glycol vinyl ether (EGVE), di(ethylene glycol) vinyl ether (DEGVE), N-vinyl lactams, including N-vinyl pyrrolidone (NVP), 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, N-vinyl-N-methyl acetamide (VMA), N-vinyl-N-ethyl acetamide, N-vinyl-N-ethyl formamide, N-vinyl formamide, N-vinyl acetamide, N-vinyl isopropylamide, allyl alcohol, N-vinyl caprolactam, N-2-hydroxyethyl vinyl carbamate, N-carboxyvinyl-β-alanine (VINAL), N-carboxyvinyl-α-alanine and mixtures thereof.

In another embodiment the slow-reacting hydrophilic monomer is selected from NVP, VMA and 1-methyl-5-methylene-2-pyrrolidone. In yet another embodiment the slow-reacting hydrophilic monomer comprises NVP.

The slow reacting hydrophilic monomer is present in amounts to provide wettability to the resulting polymer. Wettability may be measured via contact angle, and desirable contact angles are less than about 80°, less than about 70° and in some embodiments less than about 60°.

The at least one silicone-containing monomer is monofunctional and comprises (a) a fast reacting group thereof and (b) a polydialkyl siloxane chain. In another embodiment the silicon-containing monomer comprises a fast reacting group selected from (meth)acrylates, styryls, amides and mixtures thereof. The at least one silicone-containing monomer may also contain at least one fluorine. In yet another embodiment the silicone-containing component is selected from mono (meth)acryloxyalkyl polydialkylsiloxane monomer of Formula VII or the styryl polydialkylsiloxane monomer of Formula VIII:

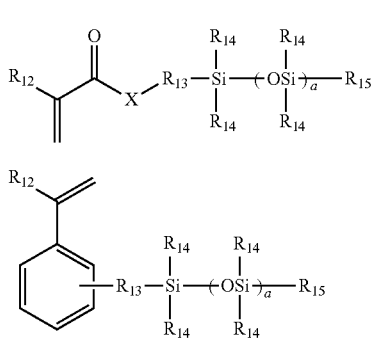

Formula VII

Formula VIII wherein $R_{12}$ is H or methyl;

X is O or $NR_{16}$;

Each $R_{14}$ is independently a phenyl or $C_1$ to $C_4$ alkyl which may be substituted with fluorine, hydroxyl or ether, and in another embodiment each $R_{14}$ is independently selected from ethyl and methyl groups, and in yet another embodiment, all $R_{14}$ are methyl;

$R_{15}$ is an unsubstituted $C_1$ to $C_4$ alkyl;

$R_{13}$ is a divalent alkyl group, which may further be functionalized with a group selected from the group consisting of ether groups, hydroxyl groups, carbamate groups and combinations thereof, and in another embodiment $C_1$-$C_6$ alkylene groups which may be substituted with ether, hydroxyl and combinations thereof, and in yet another embodiment $C_1$ or $C_3$-$C_6$ alkylene groups which may be substituted with ether, hydroxyl and combinations thereof;

a is 2 to 50, and in some embodiments 5 to 15.

$R_{16}$ is selected from H, $C_{1-4}$alkyls, which may be further substituted with one or more hydroxyl groups, and in some embodiments is H or methyl.

In yet another embodiment $R_{12}$ and each $R_{14}$ are methyl.

In yet another embodiment at least one $R_{14}$ is 3,3,3-trifluoropropyl.

Examples of suitable silicone-containing monomers include monomethacryloxyalkylpolydimethylsiloxane methacrylates selected from the group consisting of monomethacryloxypropyl terminated mono-n-butyl terminated polydimethylsiloxane, monomethacryloxypropyl terminated mono-n-methyl terminated polydimethylsiloxane, monomethacryloxypropyl terminated mono-n-butyl terminated polydiethylsiloxane, monomethacryloxypropyl terminated mono-n-methyl terminated polydiethylsiloxane, N-(2, 3-dihydroxypropane)-N'-(propyl tetra(dimethylsiloxy) dimethylbutylsilane)acrylamide, α-(2-hydroxy-1-methacryloxypropyloxypropyl)-ω-butyl-decamethylpentasiloxane, and mixtures thereof.

In another embodiment the silicone-containing component is selected from the group consisting of monomethacryloxypropyl terminated mono-n-butyl terminated polydimethylsiloxane, monomethacryloxypropyl terminated mono-n-methyl terminated polydimethylsiloxane, N-(2,3-dihydroxypropane)-N'-(propyl tetra(dimethylsiloxy) dimethylbutylsilane)acrylamide, α-(2-hydroxy-1-methacryloxypropyloxypropyl)-ω-butyl-decamethylpentasiloxane, and mixtures thereof.

In another embodiment the silicone containing component is selected from acrylamide silicones of US20110237766, and particularly the silicone monomers expressed in the following general formulae (s1) through (s6).

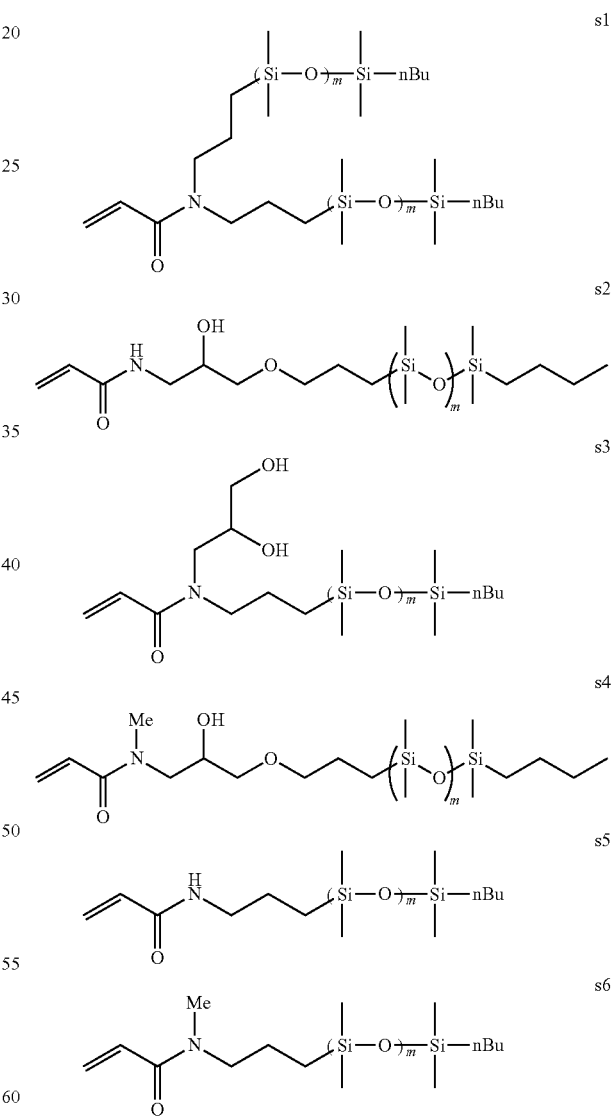

wherein m is 4-12 and in some embodiments 4-10.

Additional silicone containing components having one or more polymerizable groups may also be included. Any additional disclosed silicone components having the herein disclosed reactive groups may be included. Examples include silicone containing monomers displaying branched siloxane chains such as SiMAA and TRIS.

The at least one silicone-containing component is present in the reactive mixture in an amount sufficient to provide the desired oxygen permeability. It is a benefit of the present invention that oxygen permeabilities greater than about 70 barrers, greater than about 80 barrer, in some embodiments greater than about 90 barrer, and in other embodiments greater than about 100 barrer may be achieved. Suitable amounts will depend on the length of the siloxane chain included in the silicone-containing monomers, with silicone-containing monomers having longer chains requiring less monomer. Amounts include from about 20 to about 60 weight %, and in some embodiments from about 30 to about 55 weight %.

The slow-reacting hydrophilic monomer and the at least one silicone-containing monomer are selected such that the ratio of the kinetic half life of the slow-reacting hydrophilic monomer to the kinetic half life of the slowest silicone-containing component is at least about 2, at least about 3 and in some embodiments at least about 5.

As part of the present invention it is desirable to polymerize long chains of the slow-reacting hydrophilic monomer. A substantial amount of slow-reacting hydrophilic monomer must polymerize late in the process in order to achieve the desired balance of properties. In one embodiment this is characterized by the ratio (unit-less) of the concentrations (expressed in μmol/g) of the slow-reacting hydrophilic monomer to the slowest reacting silicone-containing monomer at 90% conversion of the slowest reacting silicone-containing monomer ("conversion ratio"). The conversion ratio is greater than about 10, at least about 20, at least about 30.

In one embodiment the reaction mixture is substantially free of TRIS, and in another is substantially free of silicone containing macromers or prepolymers.

At least one of the components of the reaction mixture must contain at least one hydroxyl group. The hydroxyl may be contained on the silicone-containing monomer, an additional monomer or a combination thereof. It is preferred that the kinetic half life of the hydroxyl-containing component be close to the kinetic half life of the silicone containing monomers. Preferred kinetic half life ratios of the hydroxyl-containing component to the silicone containing monomer include about 0.75 to about 1.5 and about 0.8 to 1.2. In one embodiment, the hydroxyl containing components have the same reactive functionality as the silicone-containing monomers.

Also, (meth)acrylate monomers with hydroxyl group(s), such as but not limited to SiMAA, and HEMA, have been found to be better at compatibilizing NVP, VMA and other amide containing monomers, than (meth)acrylamide monomers with hydroxyl group(s). Thus in one embodiment where clear lenses with dynamic advancing contact angles of less than about 80° are desired, the hydroxyl-containing monomers comprising (meth)acrylate monomers.

The hydroxyl-containing components may be present in mole percents which form a molar ratio of hydroxyl groups to the slow-reacting hydrophilic monomer of at least about 0.15 and in some embodiments between about 0.15 and about 0.4. This is calculated by dividing the number of moles of hydroxyl groups in the hydroxyl group-containing monomers (including any hydroxyl groups on the slow-reacting hydrophilic monomer and the silicone-containing monomer) by the number of moles of the slow-reacting hydrophilic monomer per a given mass of the monomer mix. In this embodiment, for a reaction mixture comprising HO-mPDMS, HEMA, EGVE and NVP, the hydroxyl groups on each of HO-mPDMS, HEMA and EGVE would be counted. Any hydroxyl groups present in the diluent (if used) are not included in the calculation. In one embodiment at least one silicone-containing monomer comprises at least one hydroxyl group.

Alternatively, the molar ratio of all hydroxyl groups on reactive components in the reaction mixture to silicon (HO: Si) is between about 0.16 and about 0.4. The molar ratio is calculated by dividing molar concentration of hydroxyl groups in the components of the reactive mixture (other than any hydroxyls which are part of the slow-reacting hydrophilic monomer or diluents) by the molar concentration of silicon. In this embodiment both the hydroxyalkyl monomers and any hydroxyl-containing silicone components are included in the calculation. Thus, in calculating the HO:Si ratio of the reaction mixture comprising HO-mPDMS, HEMA, NVP and EGVE, only the hydroxyl groups on each of HO-mPDMS, HEMA would be counted in calculating the HO:Si.

In another embodiment the molar ratio of hydroxyl groups in non-silicone containing components (other than any hydroxyls which are part of the slow-reacting hydrophilic monomer or diluents) to silicon is between about 0.13 and about 0.35. Thus, in calculating the $HO_{non-Si}$:Si ratio of the reaction mixture comprising HO-mPDMS, HEMA, EGVE, and NVP only the hydroxyl groups on, HEMA would be counted in calculating the $HO_{non-Si}$:Si ratio.

It will be appreciated that the minimum amount of hydroxyl component will vary depending upon a number of factors, including, the number of hydroxyl groups on the hydroxyalkyl monomer, the amount, molecular weight and presence or absence of hydrophilic functionality on the silicone containing components. For example, where HEMA is used as the hydroxyalkyl monomer and mPDMS is used in amounts about 38 wt % as the sole silicone containing monomer, at least about 8 wt % HEMA (0.16 HO:Si) is included to provide the desired haze values. However, when lesser amounts of mPDMS are used (about 20%), as little as about 2 or 3% HEMA provides silicone hydrogel contact lenses having haze values below about 50%. Similarly, when the formulation includes substantial amounts of a hydroxyl-containing silicone component (such as greater than about 20 wt % HO-mPDMS as in Examples 68-73), amounts of HEMA as low as about 7 wt % (0.13 HO:Si, or 0.24 $HO_{total}$:Si) may provide the desired level of haze.

Suitable hydroxyl-containing monomers include hydroxyalkyl(meth)acrylate or (meth)acrylamide monomer of Formula IX or a styryl compound of Formula X:

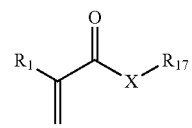

FORMULA IX

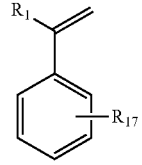

FORMULA X wherein $R_1$ is H or methyl,

X is O or $NR_{16}$, $R_{16}$ is a H, $C_1$ to $C_4$ alkyl, which may be further substituted with at least one OH, in some embodiments methyl or 2-hydroxyethyl and $R_{17}$ is selected from $C_2$-$C_4$ mono or dihydroxy substituted alkyl, and poly(ethylene glycol) having 1-10 repeating units; and in some embodiments 2-hydroxyethyl, 2,3-dihydroxypropyl, 2-hydroxypropyl.

In one embodiment $R_1$ is H or methyl, X is oxygen and R is selected from $C_2$-$C_4$ mono or dihydroxy substituted alkyl, and poly(ethylene glycol) having 1-10 repeating units. In another embodiment $R_1$ methyl, X is oxygen and R is selected from $C_2$-$C_4$ mono or dihydroxy substituted alkyl, and poly (ethylene glycol) having 2-20 repeating units, and in yet another embodiment $R_1$ methyl, X is oxygen and R is selected from $C_2$-$C_4$ mono or dihydroxy substituted alkyl. In one embodiment, at least one hydroxyl group is on the terminal end of the R alkyl group.

Examples of suitable hydroxyalkyl-containing monomers include 2-hydroxyethyl methacrylate, 2-hydroxyethyl acrylate, 3-hydroxypropyl(meth)acrylate, 2-hydroxypropyl (meth)acrylate, 1-hydroxypropyl-2-(meth)acrylate, 2-hydroxy-2-methyl-propyl(meth)acrylate, 3-hydroxy-2,2-dimethyl-propyl(meth)acrylate, 4-hydroxybutyl(meth) acrylate, glycerol(meth)acrylate, 2-hydroxyethyl(meth) acrylamide, polyethyleneglycol monomethacrylate, bis-(2-hydroxyethyl)(meth)acrylamide, 2,3-dihydroxypropyl (meth)acrylamide, and mixtures thereof.

In another embodiment the hydroxyl-containing monomer is selected from the group consisting of 2-hydroxyethyl methacrylate, glycerol methacrylate, 2 hydroxypropyl methacrylate, hydroxybutyl methacrylate, 3-hydroxy-2,2-dimethyl-propyl methacrylate, and mixtures thereof.

In yet another embodiment the hydroxyl-containing monomer comprises 2-hydroxyethyl methacrylate, and in another embodiment comprises 3-hydroxy-2,2-dimethyl-propyl methacrylate. In an alternate embodiment the hydroxyl-containing monomer comprises glycerol methacrylate.

The reactive mixture may further comprise additional hydrophilic monomers. Any hydrophilic momomers used to prepare hydrogels may be used. For example monomers containing acrylic groups ($CH_2$=CROX, where R is hydrogen or $C_{1-6}$alkyl an X is O or N) or vinyl groups (—C=$CH_2$) may be used. Examples of additional hydrophilic monomers are N,N-dimethylacrylamide, polyethyleneglycol monomethacrylate, methacrylic acid, acrylic acid, combinations thereof and the like.

If the additional hydrophilic monomers have kinetic half lives which are intermediate to the slow reacting hydrophilic monomers and silicone containing components as defined herein, their concentrations in the formulations of the present invention may be limited to concentrations which do not provide the lens with an advancing contact angle higher than about 80°. As used herein, "intermediate" half life is one that is between 20% and 70% faster than the slowest reacting silicone component. For example, if the additional hydrophilic monomer is N,N-dimethylacrylamide, the amount of the additional hydrophilic monomer is limited to below about 3 wt % in cases where uncoated lenses are desired. Where the lens is to be surface modified, higher amounts of additional monomers may be included.

The reaction mixtures of the present invention further comprise at least one crosslinker which has a kinetic half life less than or equal to the kinetic half life of at least one of the silicone-containing monomers included in the reaction mixture. A crosslinker is a monomer with two or more polymerizable double bonds. It has been found that when the kinetic half life of the crosslinker is longer than at least one of the silicone-containing monomers, the resulting hydrogel displays decreased modulus and increased water content. Surprisingly, the reaction rate of the crosslinker can be substantially reduced by the inclusion of a UV absorbing compound. This increases the kinetic half life, and in some systems changed the reaction order, such that the crosslinker reacted more slowly that the silicone-containing monomers. In this circumstance it may be desirable to use a crosslinker with a faster reaction rate in the presence of the selected UV absorber.

Suitable crosslinkers include ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The crosslinker may be used in the usual amounts, e.g., from about 0.000415 to about 0.0156 mole per 100 grams of reactive components in the reaction mixture. Alternatively, if the hydrophilic monomers and/or the silicone containing monomers act as the crosslinking agent, the addition of an additional crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone containing monomer which can act as a crosslinking agent and, when present, does not require the addition of a crosslinking monomer to the reaction mixture includes α,ω-bismethacryloypropyl polydimethylsiloxane.

The reaction mixtures can also contain multiple crosslinkers depending on the reaction rate of the hydrophilic component. With very slow reacting hydrophilic components (e.g. VMA, EGVE, DEGVE) crosslinkers having slow reacting functional groups (e.g. di-vinyl, tri-vinyl, di-allyl, tri-allyl) or a combination of slow reacting functional groups and fast reacting functional groups (e.g. HEMAVc, allylmethacrylate) can be combined with crosslinkers having fast reacting functional groups to improve the retention of the polymers of the slow-reacting monomers in the final hydrogel.

In one embodiment the reaction mixture comprises at least two crosslinkers, at least one fast reacting crosslinker having at least two fast reacting groups which will react with the silicone components and hydroxyl-containing components and at least one slow reacting crosslinker having at least two slow reacting groups which react with the slow reacting hydrophilic monomer. This mixture of fast and slow reacting crosslinkers provides the final polymer with improved resilience and recovery, particularly on the surface of the lens. Examples of suitable first crosslinkers include those having only (meth)acrylate functionality, such as EGDMA, TEGDMA and combinations thereof. Examples of suitable second crosslinkers include those having only vinyl functionality, such as triallyl cyanurate (TAC). When mixtures are used, suitable amounts of all crosslinker in the reactive mixture include between about 0.10% and about 1.0%, excluding diluent respectively. In another embodiment the total amount of all crosslinker in the reactive mixtures is between 0.7 to about 6.0 mmol/100 g of polymerizable components; between about 0.7 to about 4.0 mmoles per 100 g of reactive components. The fast and slow reacting crosslinkers are present in amounts of about 0.3 to about 2.0 mmol/100 g of polymerizable components each; and between about 0.4 to about 2.0 mmoles per 100 g of reactive components.

The reaction mixture may also comprise at least one UV absorbing compound. Surprisingly, UV absorbing compounds can have a substantially different impact on the reaction kinetics of the reactive components in the reaction mixtures of the present invention. For example, it has been found that benzotriazoles substantially slow the rate of reaction for NVP and TEGDMA is some systems much more than the reaction rates of the silicone-containing components. In the case of NVP, this is beneficial, as it provides additional processing flexibility and an exceptional balance of properties, including water contents in excess of about 60%, haze values less than about 50%, or less than about 10%, advancing contact angles less than about 60° and Dk's greater than about 80. When the silicone hydrogel will be used as an ophthalmic device it may be desirable to incorporate a reactive UV absorbing compound in the reaction mixture so that the resulting silicone hydrogel will be UV absorbing. However, in another embodiment non-reactive UV absorbing compounds may be used solely to achieve the desired reaction kinetics. Alternatively solution filters may be used. It is believed that the UV absorbers in the reactive mixtures block incident light below about 370 nm which alters the spectrum of light being imposed on the visible photoinitiator. This tends to reduce the rate of initiation as well as lower the concentration of initiator radicals present, which in turn is believed to have a significant impact on the rate of polymerization of the monomers. Typically, the monomers which are likely to be most significantly impacted are the slowest and fastest. In several of the examples included herein, NVP (slowest) and TEGDMA (the fastest) are the most sensitive to the presence of the UV absorber.

Suitable UV absorbers may be derived from 2-(2'-hydroxyphenyl)benzotriazoles, 2-hydroxybenzophenones, 2-hydroxyphenyltriazines, oxanilides, cyanoacrylates, salicylates and 4-hydroxybenzoates; which may be further reacted to incorporate reactive polymerizable groups, such as (meth)acrylates. Specific examples of UV absorbers which include polymerizable groups include 2-(2'-hydroxy-5-methacryloxyethylphenyl)-2H-benzotriazole (Norbloc), 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2,4-dihydroxyphenyl)-1,3-2H-dibenzotriazole, mixtures thereof and the like. When a UV absorber is included, it may be included in amounts between about 0.5 and about 4 wt %, and suitably between about 1 wt % and about 2 wt %.

A polymerization initiator is preferably included in the reaction mixture. The reaction mixtures of the present invention comprise at least one photoinitiator. The use of photoinitiation provides desirable cure times (time to reach essentially complete cure) of less than about 30 minutes, less than about 20 minutes or less than about 15 minutes. The photopolymerization systems also greater flexibility in tailoring the properties of the resulting silicone hydrogel through the use of UV absorbers in the reaction mixtures. Suitable photoinitiator systems include aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitiators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer. As is shown in the Examples, the concentration of photoinitiator used can affect the reaction kinetics of the reactive components. While increasing the amount of initiator generally decreases the kinetic half live of all the components, the half lives are not affected equally. Thus, the ratio of the slow-reacting hydrophilic monomer and silicone containing monomer can be adjusted by varying the initiator concentration. The effect can be increased by adding or increasing the concentration of inhibitors included in the reactive mixture. Some inhibitors may be included with the monomers which are selected Inhibitors may also be intentionally added to the reaction mixtures of the present application. The amount of inhibitor which may be included is from about 100 to about 2,500 μnm/gm of reaction mixture.

Inhibitors may optionally be included. Surprisingly the inclusion of even substantial amounts of BHT, a free radical inhibitor did not substantially change the half life ratios measured. However, inclusion of increasing amounts of inhibitor did change the properties of the resulting lenses, decreasing modulus. Thus, it may be desirable to include at least one inhibitor in the reactive mixture. Free radical inhibitors are compounds that react rapidly with propagating radicals to produce stable radical species that terminate the chain. Classes of inhibitors include quinones, substituted phenols, secondary aromatic amines, lactones and nitro compounds. Specific examples of inhibitors include BHT, MEHQ, hydroxyamines, benzofuranone derivatives, molecular oxygen, vitamin E, nitric oxide/nitrogen dioxide mixtures (which form nitroxides in situ) mixtures and combinations thereof and the like.

Examples of classes of chain transfer agents include alkyl thiols, dithiocarboxylic acid esters, combinations thereof and the like. Examples of controlled free radical initiators include nitroxide mediated polymerization (NMP) (including those disclosed in The Chemistry of Radical Polymerization, 2nd ed. Moad and Solomon, pgs 472-479), atom-transfer radical polymerization (ATRP), including low molecular weight activated organic halides (including those disclosed in The Chemistry of Radical Polymerization, 2nd ed. Moad and Solomon, pgs 488-89 and 492-497), and reversible addition fragmentation (chain) transfer (RAFT) polymerization, including thiocarbonylthio agents (such as those disclosed at including those disclosed in The Chemistry of Radical Polymerization, 2nd ed. Moad and Solomon, pgs 508-514). In the case where controlled free radical initiators are used, they are used as part or all of the initiator system.

Polymerization of the reaction mixture can be initiated using the appropriate choice visible or ultraviolet light. Alternatively, initiation can be conducted without a photoinitiator using, for example, e-beam. The initiators may be selected from bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO). In one embodiment a preferred method of polymerization initiation is visible light. In another bis(2,4,6-trimethylbenzoyl)-phenyl phosphine oxide (Irgacure 819®) is the photoinitiator.

The reaction mixture may also comprise at least one diluent or may be "neat". If a diluent is used, the selected diluents should solubilize the components in the reactive mixture. It will be appreciated that the properties of the selected hydrophilic and hydrophobic components may affect the properties of the diluents which will provide the desired compatibilization. For example, if the reaction mixture contains only moderately polar components, diluents having moderate δp may be used. If however, the reaction mixture contains strongly polar components, the diluent may need to have a high δp. However, as the diluent becomes more hydrophobic, processing steps necessary to replace the diluent with water will require the use of solvents other than water. This may undesirably increase the complexity and cost of the manufacturing process. Thus, it is important to select a diluent which provides the desired compatibility to the components with the necessary level of processing convenience.

The type and amount of diluent used also effects the properties of the resultant polymer and article. The haze, wettability and wettability of the final article may be improved by selecting relatively hydrophobic diluents and/or decreasing the concentration of diluent used.

Diluents useful in preparing the devices of this invention include polar diluents, such as ethers, esters, amides, alcohols, carboxylic acids and combinations thereof. Amides, carboxylic acids and alcohols are preferred diluents, and carboxylic acids, secondary and tertiary alcohols are more preferred diluents.

Examples of alcohols useful as diluents for this invention include those having the formula

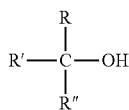

wherein R, R' and R" are independently selected from H, a linear, branched or cyclic monovalent alkyl having 1 to 10 carbons which may optionally be substituted with one or more groups including halogens, ethers, esters, aryls, amines, amides, alkenes, alkynes, carboxylic acids, alcohols, aldehydes, ketones or the like, or any two or all three of R, R' and R" can together bond to form one or more cyclic structures, such as alkyl having 1 to 10 carbons which may also be substituted as just described, with the proviso that no more than one of R, R' or R" is H.

It is preferred that R, R' and R" are independently selected from H or unsubstituted linear, branched or cyclic alkyl groups having 1 to 7 carbons. It is more preferred that R, R', and R" are independently selected form unsubstituted linear, branched or cyclic alkyl groups having 1 to 7 carbons. In certain embodiments, the preferred diluent has 4 or more, more preferably 5 or more total carbons, because the higher molecular weight diluents have lower volatility, and lower flammability. When one of the R, R' and R" is H, the structure forms a secondary alcohol. When none of the R, R' and R" are H, the structure forms a tertiary alcohol. Tertiary alcohols are more preferred than secondary alcohols. The diluents are preferably inert and easily displaceable by water when the total number of carbons is five or less.

Examples of useful secondary alcohols include 2-butanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, and the like.

Examples of useful tertiary alcohols include tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, and the like.

Examples of useful carboxylic acids include $C_2$-$C_{16}$, carboxylic acids, with one or two carboxylic acid groups and optionally a phenyl group. Specific examples include acetic acid, decanoic acid, dodecanoic acid, octanoic acid, benzylic acid, combinations thereof and the like.

A single alcohol or mixtures of two or more of the above-listed alcohols or two or more alcohols according to the structure above can be used as the diluent to make the polymer of this invention.

In certain embodiments, the diluent may be selected from secondary and tertiary alcohols having at least 4 carbons. Suitable examples of this embodiment include tert-butanol, tert-amyl alcohol, 2-butanol, 2-methyl-2-pentanol, 2,3-dimethyl-2-butanol, 3-methyl-3-pentanol, 3-ethyl-3-pentanol, 3,7-dimethyl-3-octanol.

In another embodiment the diluent may be selected from hexanol, heptanol, octanol, nonanol, decanol, tert-butyl alcohol, 3-methyl-3-pentanol, isopropanol, t amyl alcohol, ethyl lactate, methyl lactate, i-propyl lactate, 3,7-dimethyl-3-octanol, dimethyl formamide, dimethyl acetamide, dimethyl propionamide, N methyl pyrrolidinone and mixtures thereof. Additional diluents useful for this invention are disclosed in U.S. Pat. No. 6,020,445, and US 2010-0280146 A1 which is incorporated herein by reference.

In one embodiment of the present invention the diluent is water soluble at processing conditions and readily washed out of the lens with water in a short period of time. Suitable water soluble diluents include 1-ethoxy-2-propanol, 1-methyl-2-propanol, t-amyl alcohol, tripropylene glycol methyl ether, isopropanol, 1-methyl-2-pyrrolidone, N,N-dimethylpropionamide, ethyl lactate, dipropylene glycol methyl ether, mixtures thereof and the like. The use of a water soluble diluent allows the post molding process to be conducted using water only or aqueous solutions which comprise water as a substantial component.

The diluents may be used in amounts up to about 40% by weight of the total of all components in the reactive mixture. In one embodiment the diluent(s) are used in amounts less than about 30% and in another in amounts between about 2 and about 20% by weight of the total of all components in the reactive mixture.

It has been found that even amounts of diluent as low as 2-20 wt %, can lower the modulus of the resulting polymer by about 20% and improve wettability of the resulting polymers and lenses.

The diluent may also comprise additional components to lower the modulus of the resulting polymers and improve the lens curing efficiency and reducing residuals. Components capable of increasing the viscosity of the reactive mixture and/or increasing the degree of hydrogen bonding with the slow-reacting hydrophilic monomer, are desirable. Suitable components include polyamides, polylactams, such as PVP and copolymers thereof, polyols and polyol containing components such glycerin, boric acid, boric acid glycerol esters, polyalkylene glycols, combinations thereof and the like.

Suitable polylactams include PVP and copolymers comprising repeating units from NVP and hydrophilic monomers. In one embodiment, the polylactam is selected from, PVP, and the polyamide comprises DMA.

When polyamides or polylactams are used they have a molecular weight of between about K12-K120 (about 3900 to about 3,000,000 Dalton $M_w$) and in some embodiments from K30 to K90 (about 42,000 to about 1,300,000 Dalton $M_w$).

Suitable polyalkylene glycols include polyethylene glycol and polypropylene glycols having molecular weight up to about 350 and in some embodiments less than about 200 gm/mol.

When used, the polyols, polyol containing components, polyamides and polylactams are used in amounts less than about 5 wt %, or from about 0.2 to about 5 wt %. The diluents and co-diluents of the present invention also reduce the residuals remaining in the polymer at the end of the photo-cure. This provides lenses with more consistent properties, including diameter. In some embodiments the residual slow-reacting hydrophilic component present at the end of cure are less than about 2 wt % cured polymer ((wt of residual component/wt of cured polymer)*100%), or less than about 1 wt % and in some cases less than about 0.8 wt %. The reduction in residuals also leads to more consistent lens properties, including lens diameters, which can vary by less than about 0.05 mm.

The reactive mixture may contain additional components such as, but not limited to, medicinal agents, antimicrobial compounds, reactive tints, pigments, copolymerizable and non-polymerizable dyes, release agents and combinations thereof.

Combinations of reactive components and diluents include those having from about 20 to about 65 weight % silicone containing monomer, about 25 to about 70 weight % slow-reacting hydrophilic monomer, from about 2 to about 40 weight % of an hydroxyl containing component, from about 0.2 to about 3 weight % of at least one crosslinking monomer, from about 0 to about 3 weight % of a UV absorbing monomer, (all based upon the weight % of all reactive components). The mixture may further comprises between about 20 to about 60 weight % (weight % of all components, both reactive and non-reactive) of one or more diluents.

The reaction mixtures of the present invention can be formed by any of the methods known to those skilled in the art, such as shaking or stirring, and used to form polymeric articles or devices by known methods.

For example, the biomedical devices of the invention may be prepared by mixing reactive components and the diluent(s) with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197, 266. The method for producing contact lenses comprising the polymer of this invention may be by the direct molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product.

Referring to FIG. 1, a diagram is illustrated of an ophthalmic lens 100, such as a contact lens, and mold parts 101-102 used to form the ophthalmic lens 100. In some embodiments, the mold parts include a back surface mold part 101 and a front surface mold part 102. As used herein, the term "front surface mold part" refers to the mold part whose concave surface 104 is a lens forming surface used to form the front surface of the ophthalmic lens. Similarly, the term "back surface mold part" refers to the mold part 101 whose convex surface 105 forms a lens forming surface, which will form the back surface of the ophthalmic lens 100. In some embodiments, mold parts 101 and 102 are of a concavo-convex shape, preferably including planar annular flanges, which surround the circumference of the uppermost edges of the concavo-convex regions of the mold parts 101-102.

Typically, the mold parts 101-102 are arrayed as a "sandwich". The front surface mold part 102 is on the bottom, with the concave surface 104 of the mold part facing upwards. The back surface mold part 101 can be disposed symmetrically on top of the front surface mold part 102, with the convex surface 105 of the back surface mold part 101 projecting partially into the concave region of the front surface mold part 102. The back surface mold part 101 may be dimensioned such that the convex surface 105 thereof engages the outer edge of the concave surface 104 of the front mold part 102 throughout its circumference, thereby cooperating to form a sealed mold cavity in which the ophthalmic lens 100 is formed.

The mold parts 101-102 may be fashioned of thermoplastic and are transparent to polymerization-initiating actinic radiation, by which is meant that at least some, and in some embodiments all, radiation of an intensity and wavelength effective to initiate polymerization of the reaction mixture in the mold cavity can pass through the mold parts 101-102.

For example, thermoplastics suitable for making the mold parts can include: polystyrene; polyvinylchloride; polyolefin, such as polyethylene and polypropylene; copolymers or mixtures of styrene with acrylonitrile or butadiene, polyacrylonitrile, polyamides, polyesters, cyclic olefin copolymers such as Topas available from Ticona or Zeonor available from Zeon, copolymers and blends of any of the foregoing, or other known material.

Following polymerization of the reaction mixture to form a lens 100, the lens surface 103 will typically adhere to the mold part surface 104. The steps of the present invention facilitate release of the surface 103 from the mold part surface. The first mold part 101 can be separated from the second mold part 102 in a demolding process. The lens 100 may have adhered to the second mold part 102 (i.e. the front curve mold part) during the cure process and remain with the second mold part 102 after separation until the lens 100 has been released from the front curve mold part 102. Alternatively, the lens 100 can adhere to the first mold part 101.

The lens 100 may be released from the mold by any process, including contacting with a solvent or dry release. For example, the lens 100 and the mold part to which it is adhered after demolding may be contacted with an aqueous solution. The aqueous solution can be heated to any temperature below the boiling point of the aqueous solution. Heating can be accomplished with a heat exchange unit to minimize the possibility of explosion, or by any other feasible means or apparatus for heating a liquid.

As used herein, processing includes the steps of removing the lens from the mold and removing or exchanging the diluent with an aqueous solution. The steps may be done separately, or in a single step or stage. The processing temperature may be any temperatures between about 30° C. and the boiling point of the aqueous solutions, for example between about 30° C. and about 95° C., or between about 50° C. and about 95° C.

The aqueous solution is primarily water. In some embodiments, the aqueous solution is at least about 70 wt % water, and in other embodiments at least about 90 weight % water and in other embodiments at least about 95%. The aqueous solution may also be a contact lens packaging solution such as borate buffered saline solution, sodium borate solutions, sodium bicarbonate solutions and the like. The aqueous solution may also include additives, such as surfactants, preservatives, release aids, antibacterial agents, pharmaceutical and nutriceutical components, lubricants, wetting agents, salts, buffers, mixtures thereof and the like. Specific examples of additives which may be included in the aqueous solution include Tween 80, which is polyoxyethylene sorbitan monooleate, Tyloxapol, octylphenoxy(oxyethylene) ethanol, amphoteric 10), EDTA, sorbic acid, DYMED, chlorhexadine gluconate, hydrogen peroxide, thimerosal, polyquad, polyhexamethylene biguanide, mixtures thereof and the like. Where various zones are used, different additives may be included in different zones. Additives may be added to the hydration solution in amounts varying between 0.01% and 10% by weight, but cumulatively less than about 10% by weight.

Exposure of the ophthalmic lens 100 to the aqueous solution can be accomplished by any method, such as washing, spraying, soaking, submerging, or any combination of the aforementioned. For example, the lens 100 can be washed with an aqueous solution comprising deionized water in a hydration tower.

Using a hydration tower, front curve mold parts 102 containing lenses 100 can be placed in pallets or trays and stacked vertically. The aqueous solution can be introduced at the top of the stack of lenses 100 so that the solution will flow downwardly over the lenses 100. The solution can also be introduced at various positions along the tower. The trays can be moved upwardly allowing the lenses 100 to be exposed to increasingly fresher solution.

Alternatively, the ophthalmic lenses 100 may be soaked or submerged in the aqueous solution.

The contacting step can last up to about 12 hours, in some embodiments up to about 2 hours and in other embodiments from about 2 minutes to about 2 hours; however, the length of the contacting step depends upon the lens materials, including any additives, the materials that are used for the solutions or solvents, and the temperatures of the solutions. Sufficient treatment times typically shrink the contact lens and release the lens from the mold part. Longer contacting times will provide greater leaching.

The volume of aqueous solution used may be any amount greater than about 1 ml/lens and in some embodiments greater than about 5 ml/lens.

In some methods, after separation or demolding, the lenses on the front curves, which may be part of a frame, are mated with individual concave slotted cups to receive the contact lenses when they release from the front curves. The cups can be part of a tray. Examples can include trays with 32 lenses each, and 20 trays that can be accumulated into a magazine.

Alternatively, the lenses may be submerged in the aqueous solution. Magazines can be accumulated and then lowered into tanks containing the aqueous solution. The aqueous solution may also include other additives as described above.

The ophthalmic devices, and particularly ophthalmic lenses of the present invention have a balance of properties which makes them particularly useful. Such properties include clarity, optics, water content, oxygen permeability and advancing contact angle. Thus, the biomedical devices may be contact lenses having a water content of greater than about 55%, greater than about 60%.

As used herein clarity means substantially free from visible haze. Clear lenses have a haze value of less than about 70%, more preferably less than about 50% and less than about 10%.

Suitable oxygen permeabilities include those greater than about 80 barrer, greater than about 85 barrer, or at least about 100 barrer.

Also, the biomedical devices, and particularly ophthalmic devices and contact lenses have moduli which are less than about 150 psi, or less than about 100 psi.

The biomedical devices, and particularly ophthalmic devices and contact lenses have average contact angles (advancing) which are less than about 80°, less than about 75° or less than about 70°. The articles of the present invention may have combinations of the above described oxygen permeability, water content and contact angle. All combinations of the above ranges are deemed to be within the present invention.

Hansen Solubility Parameter

The Hansen solubility parameter, $\delta p$ may be calculated by using the group contribution method described in Barton, CRC Handbook of Solubility Par., 1st. Ed. 1983, page 85-87 and using Tables 13, 14.

Haze Measurement

Haze is measured by placing a hydrated test lens in borate buffered saline in a clear 20×40×10 mm glass cell at ambient temperature above a flat black background, illuminating from below with a fiber optic lamp (Dolan-Jenner PL-900 fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 2.2 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

Alternatively, instead of a −1.00 diopter CSI Thin Lenses®, a series of aqueous dispersions of stock latex spheres (commercially available as 0.49 μm Polystyene Latex Spheres—Certified Nanosphere Size Standards from Ted Pella, Inc., Product Number 610-30) can be used as standards. A series of calibration samples were prepared in deionized water. Each solution of varying concentration was placed in a cuvette (2 mm path length) and the solution haze was measured using the above method.

| Solution | Concentration (wt % × $10^{-4}$) | Mean GS |
|---|---|---|
| 1 | 10.0 | 533 |
| 2 | 6.9 | 439 |

| Solution | Concentration (wt % × 10⁻⁴) | Mean GS |
|---|---|---|
| 3 | 5.0 | 379 |
| 4 | 4.0 | 229 |
| 5 | 2.0 | 172 |
| 6 | 0.7 | 138 |

Mean GS = mean gray scale

A corrective factor was derived by dividing the slope of the plot of Mean GS against the concentration (47.1) by the slope of an experimentally obtained standard curve, and multiplying this ratio times measured scatter values for lenses to obtain GS values.

"CSI haze value" may be calculated as follows:

$$\text{CSI haze value} = 100 \times (GS-BS)/(217-BS)$$

Where GS is gray scale and BS is background scatter.

Water Content

The water content of contact lenses was measured as follows: Three sets of three lenses are allowed to sit in packing solution for 24 hours. Each lens is blotted with damp wipes and weighed. The lenses are dried at 60° C. for four hours at a pressure of 0.4 inches Hg or less. The dried lenses are weighed. The water content is calculated as follows:

$$\% \text{ water content} = \frac{(\text{wet weight} - \text{dry weight})}{\text{wet weight}} \times 100$$

The average and standard deviation of the water content are calculated for the samples and are reported.

Modulus

Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Percent elongation is =[(Lf−Lo)/Lo]×100. Tensile modulus is measured at the initial linear portion of the stress/strain curve.

Advancing Contact Angle

All contact angles reported herein are advancing contact angles. The advancing contact angle was measured as follows. Four samples from each set were prepared by cutting out a center strip from the lens approximately 5 mm in width and equilibrated in packing solution. The wetting force between the lens surface and borate buffered saline is measured at 23° C. using a Wilhelmy microbalance while the sample is being immersed into or pulled out of the saline. The following equation is used $$F = 2\gamma p \cos\theta \text{ or } \delta = \cos^{-1}(F/2\gamma p)$$

where F is the wetting force, $\gamma$ is the surface tension of the probe liquid, p is the perimeter of the sample at the meniscus and $\theta$ is the contact angle. The advancing contact angle is obtained from the portion of the wetting experiment where the sample is being immersed into the packing solution. Each sample was cycled four times and the results were averaged to obtain the advancing contact angles for the lens.

Oxygen Permeability (Dk)

The Dk is measured as follows. Lenses are positioned on a polarographic oxygen sensor consisting of a 4 mm diameter gold cathode and a silver ring anode then covered on the upper side with a mesh support. The lens is exposed to an atmosphere of humidified 2.1% $O_2$. The oxygen that diffuses through the lens is measured by the sensor. Lenses are either stacked on top of each other to increase the thickness or a thicker lens is used. The L/Dk of 4 samples with significantly different thickness values are measured and plotted against the thickness. The inverse of the regressed slope is the Dk of the sample. The reference values are those measured on commercially available contact lenses using this method. Balafilcon A lenses available from Bausch & Lomb give a measurement of approx. 79 barrer. Etafilcon lenses give a measurement of 20 to 25 barrer. (1 barrer=$10^{-10}$ ($cm^3$ of gas×$cm^2$)/($cm^3$ of polymer×sec×cm Hg)).

Lysozyme, Lipocalin & Mucin Uptake

Lysozyme uptake was measured as follows: The lysozyme solution used for the lysozyme uptake testing contained lysozyme from chicken egg white (Sigma, L7651) solubilized at a concentration of 2 mg/ml in phosphate saline buffer supplemented by Sodium bicarbonate at 1.37 g/l and D-Glucose at 0.1 g/l.

Three lenses for each example were tested using each protein solution, and three were tested using PBS (phosphate buffered saline) as a control solution. The test lenses were blotted on sterile gauze to remove packing solution and aseptically transferred, using sterile forceps, into sterile, 24 well cell culture plates (one lens per well) each well containing 2 ml of lysozyme solution. Each lens was fully immersed in the solution. 2 ml of the lysozyme solution was placed in a well without a contact lens as a control.

The plates containing the lenses and the control plates containing only protein solution and the lenses in the PBS, were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile conical tubes (1 lens per tube), each tube containing a volume of PBS determined based upon an estimate of lysozyme uptake expected based upon on each lens composition. The lysozyme concentration in each tube to be tested needs to be within the albumin standards range as described by the manufacturer (0.05 micogram to 30 micrograms). Samples known to uptake a level of lysozyme lower than 100 μg per lens were diluted 5 times. Samples known to uptake levels of lysozyme higher than 500 μg per lens (such as etafilcon A lenses) are diluted 20 times.

1 ml aliquot of PBS was used for all samples other than etafilcon. 20 ml were used for etafilcon A lens. Each control lens was identically processed, except that the well plates contained PBS instead of lysozyme solution.

Lysozyme uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lysozyme solution.

Optical density was measured using a SynergyII Microplate reader capable for reading optical density at 562 nm.

Lipocalin uptake was measured using the following solution and method. The lipocalin solution contained B Lactoglobulin (Lipocalin) from bovine milk (Sigma, L3908) solubilized at a concentration of 2 mg/ml in phosphate saline buffer (Sigma, D8662) supplemented by sodium bicarbonate at 1.37 g/l and D-Glucose at 0.1 g/l.

Three lenses for each example were tested using the lipocalin solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of lipocalin solution. Each lens was fully immersed in the solution. Control lenses were prepared using PBS as soak solution instead of lipocalin. The plates containing the lenses immersed in lipocalin solution as well as plates containing control lenses immersed in PBS, were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile 24 well plates each well containing 1 ml of PBS solution.

Lipocalin uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lipocalin solution. Optical density was measured using a SynergyII Micro-plate reader capable for reading optical density at 562 nm.

Mucin uptake was measured using the following solution and method. The Mucin solution contained Mucins from bovine submaxillary glands (Sigma, M3895-type 1-S) solubilized at a concentration of 2 mg/ml in phosphate saline buffer (Sigma, D8662) supplemented by sodium bicarbonate at 1.37 g/l and D-Glucose at 0.1 g/l.

Three lenses for each example were tested using Mucin solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of Mucin solution. Each lens was fully immersed in the solution. Control lenses were prepared using PBS as soak solution instead of lipocalin.

The plates containing the lenses immersed in Mucin as well as plates containing control lenses immersed in PBS were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile 24 well plates each well containing 1 ml of PBS solution.

Mucin uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in Mucin solution. Optical density was measured using a SynergyII Micro-plate reader capable for reading optical density at 562 nm.

Kinetics

Preparation of Reactive Monomer Mixes: 15-20 g Batch

The preparation of the reactive monomer mixtures for the kinetics studies were prepared under yellow light as follows. The components for each kinetics example were weighed into a 20 mL amber borosilicate glass scintillation vial (Wheaton 320 brand; Catalogue #80076-576, or equivalent). Vials were capped (using PTFE lined green cap, Qorpak; Supplier #5205/100, Catalogue #16161-213) and rolled on jar roller until all solids were dissolved and a homogeneous mixtures were obtained.

Degas

Figure 2:
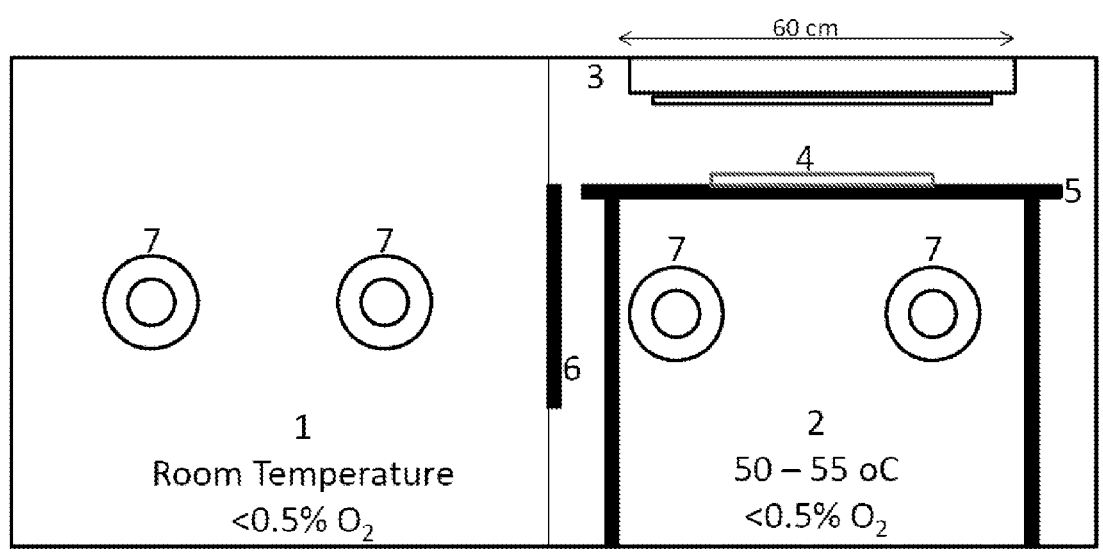
FIG. 2 is a schematic of the dual compartment cure box used for the kinetic evaluations.

Reactive monomer mixes were degassed under vacuum, under yellow light for 7-10 minutes, and back-filling with nitrogen after breaking vacuum. Vials were quickly capped and placed in compartment 1 of a two compartment nitrogen cure box, via the gated aperature, 7, as shown in FIG. 2. The conditions in compartment 1 were room temperature and <0.5% oxygen (using continuous nitrogen purge).

Nitrogen Cure Box—Compartment 2

The oxygen level in both compartments was maintained by continuous/constant nitrogen purge. The temperature in Compartment 2 was maintained by a heater (COY, Laboratory Products Inc.). The nitrogen cure box was allowed to equilibrate for a minimum of 4 hours prior to performing each kinetics study. The degassed reactive mixture (in tightly capped abmber vial) was placed in compartment 1 during the equilibration period.

Light Source and Intensity Setting

Figure 3:
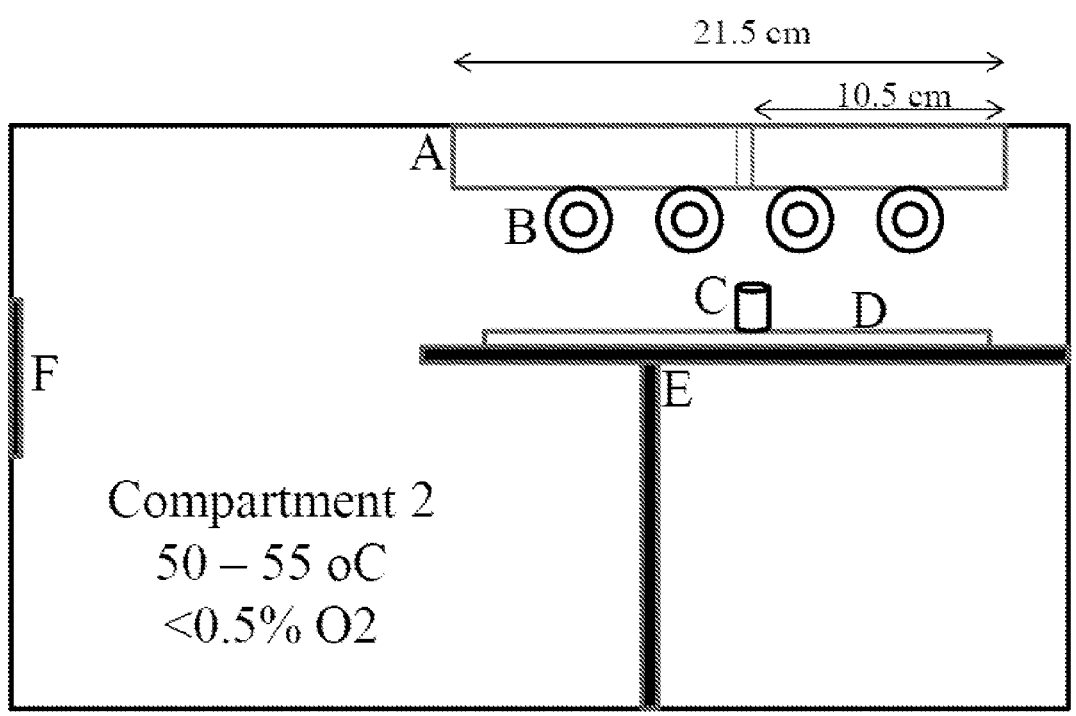
FIG. 3 is a schematic of compartment 2 of the cure box show in FIG. 2.

As depicted in FIG. 3, 2 fluorescent light fixtures (Lithonia Lighting Fluorescent Luminaire (Gas Tube Luminaire), 60 cm×10.5 cm) each equipped with 2 fluorescent lamps (Philips TLK 40 W/03, 58 cm) were arranged in parallel. The cure intensity was attenuated by adjusting the height of the shelf (shown in FIGS. 2 and 3) relative to the light source. The intensity at a given shelf height was measured by placing the sensor of a calibrated radiometer/photometer on the mirrored surface, consistent with the position of the sample, as shown in FIG. 3. The sensor was placed directly under the space between the $2^{nd}$ and $3^{rd}$ lamps in the 4 lamps arrangement.

Using a calibrated analytical balance (4 decimal places) the weight of a clear borosilicate glass scintillation vial (Wheaton 986541) with cap (white cap with polyethylene insert) was determined. The vial with cap was transferred to Compartment 1 of the Nitrogen Cure Box. The cap was unscrewed and using a calibrated 10-100 μL Eppendorf Pipet, 100 μL of the Reactive Monomer Mixture was transferred into the vial. The vial was tightly capped, quickly moved into Compartment 2, via door 6, and placed on the mirrored surface 4, as shown in FIG. 2. The sample was placed directly under the space between the $2^{nd}$ and $3^{rd}$ lamps in the 4 lamps arrangement. The light source 3, was turned on and the sample was exposed for a specified time period. Although the light source was set at 4-5 mW/cm$^2$, the actual intensity reaching the sample is 0.7-1.3 mW/cm$^2$, due the cap on the sample glass vials. After exposure, the light source 3, was turned off and the vial (with cap) was re-weighed to determine the sample weight by difference. Using a calibrated 500-5000 μL Eppendorf Pipet, 10 mL HPLC grade methanol was added to the vial.

Aliquots (100 μL) of the Reactive Monomer Mixture were pipetted into separate borosilicate glass scintillation vials and the above procedure described above was performed to generate samples at the following minimum time points (minutes): 0, 0.25, 0.50, 0.75, 1, 2, 4, 6, 8, 10.

Cured polymers were extracted in methanol overnight by gently shaking at room temperature.

Extracts were analyzed for residual components by High Performance Liquid Chromatography with UV detection (HPLC/UV) using the following procedures.

Quantitation of the mPDMS in the extracts was performed against external calibration standards (about 6-11, using the response of the n=6 oligomer), typically covering the range of 1 ng/mL-800 ng/mL. If the concentrations of mPDMS in the extracts were outside the calibration range, the extracts were diluted with methanol to render concentrations within the calibration range for more accurate quantitation.

Chromatographic Conditions
Column: Agilent Zorbax Eclipse XDB18, 4.6×50 mm×1.8 μm
Column Temperature: 30° C.
UV Detector: 217 nm
Injection Volume: 20 μl
Mobile Phase
Eluent A: De-ionized
Eluent B: Acetonitrile
Eluent C: Isopropanol
Flow Rate: 1 mL/min

| Time (mins) | % A | % B | % C |
| --- | --- | --- | --- |
| 0.0 | 50 | 48 | 2 |
| 0.5 | 50 | 48 | 2 |
| 2.0 | 0 | 60 | 40 |
| 5.0 | 0 | 60 | 40 |
| 5.1 | 0 | 30 | 70 |
| 8.0 | 0 | 30 | 70 |
| 8.1 | 50 | 48 | 2 |
| 10.0 | 50 | 48 | 2 |

Quantitation of the components in the extracts other than mPDMS was performed against external calibration standards (about 6-11) for each component, typically covering the range of 1 ng/mL-800 ng/mL. If the concentrations of components in the extracts were outside the calibration range, the extracts were appropriately diluted with methanol to render concentrations within the calibration range for more accurate quantitation.

Chromatographic Conditions
Column: Agilent Zorbax Eclipse Plus 18, 4.6×75 mm×1.8 μm
Column Temperature: 30° C.
UV Detector: 217 nm
Injection Volume: 5 μL
Mobile Phase
Eluent A: De-ionized water with 0.05% $H_3PO_4$
Eluent B: Acetonitrile with 0.05% $H_3PO_4$
Eluent C: Methanol
Flow Rate: 1 mL/min

| Time (mins) | % A | % B | % C |
| --- | --- | --- | --- |
| 0 | 95 | 5 | 0 |
| 5 | 95 | 5 | 0 |
| 15 | 0 | 100 | 0 |
| 23 | 0 | 100 | 0 |
| 24 | 0 | 30 | 70 |
| 28 | 0 | 30 | 70 |
| 29 | 95 | 5 | 0 |
| 35 | 95 | 5 | 0 |

Calculations
1. At each time point the following values are determined. The concentration (μg/mL) of each component in the sample extract.

The concentration of each component in the sample extract, expressed as a percent of the sample weight as follows:

% Component=[(μg/mL*Volume of Extract*Dilution Factor*$10^{-6}$ g/μg)/(g Sample Weight)]*100

The percent unreacted component present, expressed as a percent relative to $T_0$ (where $T_0$ represented 100% unreacted component)

% at $T_x$=(% Measured at $T_x$/% Measured at $T_0$)*100

2. Using the % Component calculated above, the concentration of each component in μmoles/g, is calculated as follows:

μmoles/g=(% Component*$10^3$)/(Molecular Weight of Component)

3. Using the concentration of each component determined in μmoles/g in step 2, the concentration at $Time_x$ was expressed as Log $[A_x]/[A_o]$, where $[A_x]$ is the concentration of component A at x minutes and $[A_o]$ is the concentration of component A at 0 minutes ($T_0$)

The expression Log $[A_x]/[A_o]$ was determined for each time point.

First order kinetics were assumed for determining both the polymerization kinetics rate and half life for each component. The following equations were used for calculating polymerization rate Log $[A]/[A_0]$=-kt/2.303 and half life ln $[A_0]/[0.5A_0]$=$k_{1/2}$ or $t_{1/2}$=0.693/k

For each component, a plot of Log $[A_x]/[A_0]$ versus time (minutes) was generated. Typically, the data points (x, y) that best correspond to linear growth (shorter cure times) were plotted and the data were fitted to a linear equation.

Using the slope, the kinetic rate constant (k) of each component was evaluated from the following equation:

k(minute$^{-1}$)=Slope*-2.303

The half-life (minutes) of each component was evaluated from the following equation:

$t_{1/2}$=0.693/k

The evaluated half-life for each component was compared to the data generated for the percent of each component relative to $T_0$, at each time point. Typically for each component, the time taken to attain 50% consumption was close to the half-life based on $1^{st}$ order kinetics. In cases where the two were significantly different (typically about 30% for half-life of less than about 1 minute, 25% for half-life less than about 2.5 minutes but greater than 1 minute and 20% for half-life greater than 2.5 minutes), the data points (x, y) were re-evaluated to generate kinetic rate constants (k) which would provide half-lives (based on $1^{st}$ order considerations) more consistent (within 20%) with the measured values.

The Examples below further describe this invention, but do not limit the invention. They are meant only to suggest a method of practicing the invention. Those knowledgeable in the field of contact lenses as well as other specialties may find other methods of practicing the invention. However, those methods are deemed to be within the scope of this invention. Some of the other materials that are employed in the Examples are identified as follows:

EXAMPLES

The following abbreviations are used in the examples below:
FC Front mold curves
BC Back mold curves
SiMAA (3-methacryloxy-2-hydroxypropoxy)propyl-bis(trimethylsiloxy)methylsilane (Also known as SiGMA)
DMA N,N-dimethylacrylamide
EGVE ethylene glycol vinyl ether
HEMA 2-hydroxyethyl methacrylate
HEAA hydroxyethylacrylamide
HBMA 2-hydroxybutyl methacrylate, prepared as in Example 118
HPMA 2-hydroxypropyl methacrylate (ACROS)
DMHEMA dimethylhydroxyethylmethacrylate, prepared as in Example 119
mPDMS 800-1000 MW ($M_n$) monomethacryloxypropyl terminated mono-n-butyl terminated polydimethylsiloxane
OH-mPDMS α-(2-hydroxy-1-methacryloxypropyloxypropyl)-ω-butyl-decamethylpentasiloxane, (MW 612 g/mol), prepared as in Example 8 of US20100249356 A1
Norbloc 2-(2'-hydroxy-5-methacrylyloxyethylphenyl)-2H-benzotriazole
D3O 3,7-dimethyl-3-octanol
IPA isopropyl alcohol
TAC triallylcyanurate
TEGDMA tetraethyleneglycol dimethacrylate
TRIS 3-methacryloxypropyltris(trimethylsiloxy)silane
acPDMS bis-3-methacryloxy-2-hydroxypropyloxypropyl polydimethylsiloxane (MW about 1000 g/mole)
CGI 819 bis(2,4,6-trimethylbenzoyl)-phenylphosphineoxide
EtOAc ethyl acetate
DA decanoic acid
Macromer A Described in Example 25 of U.S. Pat. No. 6,943,203
GMMA 2,3-dihydroxypropyl methacrylate
TAA t-amyl alcohol
ETOH ethanol
SA-2 N-(2,3-dihydroxypropane)-N'-(propyl tetra(dimethylsiloxy)dimethylbutylsilane)acrylamide, as shown in Formula XI

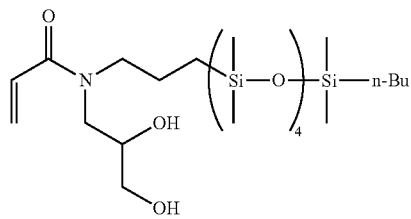

VMA N-vinyl-N-methyl acetamide
NVP N-vinylpyrrolidone
BHT butylated hydroxytoluene
PVP poly(N-vinylpyrrolidone)
EGVE ethyleneglycol vinyl ether
VINAL an ionic amide containing vinyl ether having the structure

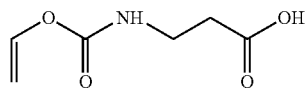

and prepared in Example 120

BAE (Boric Acid Ester) was formed as follows:

1.24 parts of a 5% (wt) solution of ethylenediaminetetraacetic acid, 299 parts (wt) glycerol and 100 parts (wt) boric acid were added to a reaction flask. The mixture was heated with stirring to 90° C. Vacuum was applied to reduce the pressure to less than 6 torr as the mixture was stirred for 155 minutes, with removal of water vapor. The pressure was reduced to less than 2 torr and the reaction was continued for 2 hours, or longer as needed until the % water of the mixture was reduced to less than 0.2% using a Karl Fischer test.

BAGE (Boric Acid Glycerol Ester) was formed as follows:
To BAE prepared as described above was added 624 parts (wt) glycerol with stirring for 60 minutes at 35-40° C.

Example 1 and Comparative Example 1

A reaction mixture was formed by mixing the components listed in Table 1 and degassed by applying vacuum at ambient temperature for about 17(±3) minutes. The reaction mixture (75 μL) was then dosed at room temperature and <0.5% $O_2$, into thermoplastic contact lens molds (FC-Zeonor, BC Polypropylene) which had been degassed in $N_2$ box at RT (Compartment 1, FIG. 2) for a minimum of 12 hours prior to dosing. The BC was placed on the FC mold to produce 8 BC/FC assemblies in a pallet. Eight pallets were assembled and moved into the cure compartment (Compartment 2, FIG. 2). Pallets were placed on a mirrored surface and a quartz plate (0.50 mm thick) was placed over each pallet. The lenses were cured for 18 minutes, at an intensity of 4-5 mW/cm², <0.5% $O_2$, and 50-55° C.

The molds were manually demolded (lenses remained in FC) and lenses were released in 50/50 IPA/$H_2O$ (8 pallets, 8 lenses per pallet), 1 L solution, 1 hour.

Lenses were "stepped down" into PS in the following order: 25/75IPA/$H_2O$ (10 mins), $H_2O$ (30 mins), $H_2O$ (10 mins), $H_2O$ (10 mins), and stored in borate buffered packing solution in lens vials and sterilized at 122° C. for 30 minutes.

TABLE 1

| Component | Ex. 1 NVP | CE 1 DMA |
|---|---|---|
| OH-mPDMS, n = 4 | 40 | 40 |
| NVP | 50.5 | 0 |
| DMA | 0 | 50.5 |
| HEMA | 6.75 | 6.75 |
| TEGDMA | 0.5 | 0.5 |
| Norblock | 2 | 2 |
| CGI 819 | 0.25 | 0.25 |

TABLE 2

| | % | | | Mechanicals | | |
|---|---|---|---|---|---|---|
| Ex. # | % $H_2O$ | Haze | DCA | Mod. (psi) | Elong. (%) | Dk |
| 1 | 58.4 (0.2) | 4 (0) | 44 (4) | 102.9 (11.4) | 220.3 (36.2) | 74.7 |
| CE1 | 59.8 (0.1) | 5 (1) | 127 (14) | 54.1 (7.4) | 227.3 (52.3) | 48.5 |

The lenses of Example 1 exhibited exceptional haze (4%), wettability (DCA) 44°, modulus, elongation and Dk. The lenses of Comparative Example 1 exhibited greatly increased advancing contact angle (127°), indicating a marked decrease in wettability. Comparative Example 1 also displayed a substantially reduced modulus (54.1 psi) and oxygen permeability (48.5) compared to Example 1 (102.9 and 74.7, respectively).

Examples 2 and Comparative Example 2

The polymerization rate and half life for each component in the Formulations of Example 1 and Comparative Example 1 were determined using the procedure described in the kinetics section above. In each Example, for each of the components in the sample extract and at each of the time points the following information is reported, the wt % of each residual component measured (Table 3), % incorporation of each residual component at each time point relative to the % residual measured at $T_0$ (Table 4), the μmole/g of each residual component at each time point (Table 5) and, log $[A]/[A_0]$ (Table 6), and the polymerization rate constants and half-lives (Tables 7 and 8).

TABLE 5

Ex. 2 RESIDUAL MONOMERS (umoles/g)

| Cure Time mins | NVP | HEMA | TEGDMA | Norbloc | CGI 819 | OH-mPDMS |
|---|---|---|---|---|---|---|
| 0.00 | 4386.23 | 508.60 | 17.25 | 62.66 | 5.04 | 604.57 |
| 0.25 | 4515.93 | 441.52 | 13.20 | 55.55 | 3.99 | 548.76 |
| 0.50 | 4509.28 | 381.39 | 10.58 | 49.31 | 3.08 | 488.62 |
| 1.00 | 4327.69 | 277.76 | 6.48 | 35.46 | 1.60 | 373.43 |
| 2.00 | 4083.51 | 132.44 | 2.51 | 17.04 | 0.48 | 191.32 |
| 4.00 | 3361.70 | 39.99 | 1.05 | 2.62 | 0.05 | 60.85 |
| 6.00 | 3149.41 | 33.74 | 0.94 | 1.14 |  | 55.44 |
| 8.00 | 2896.87 | 25.37 | 0.72 | 0.48 |  | 41.86 |
| 10.00 | 2218.40 |  |  |  |  |  |

TABLE 6

| Cure Time | NVP Log[A]/[A₀] | HEMA Log[A]/[A₀] | TEGDMA Log[A]/[A₀] | Norblock Log[A]/[A₀] | CGI 819 Log[A]/[A₀] | OH-mPDMS Log[A]/[A₀] |
|---|---|---|---|---|---|---|
| 0.25 | 0.0127 | −0.0614 | −0.1164 | −0.0523 | −0.1017 | −0.0421 |
| 0.50 | 0.0120 | −0.1250 | −0.2122 | −0.1041 | −0.2136 | −0.0925 |
| 1.00 | −0.0058 | −0.2627 | −0.4253 | −0.2473 | −0.4997 | −0.2092 |
| 2.00 | −0.0311 | −0.5844 | −0.8371 | −0.5656 | −1.0250 | −0.4997 |
| 4.00 | −0.1155 | −1.1044 | −1.2146 | −1.3784 | −1.9814 | −0.9972 |
| 6.00 | −0.1439 | −1.1783 | −1.2634 | −1.7418 |  | −1.0377 |
| 8.00 | −0.1802 | −1.3021 | −1.3814 | −2.1130 |  | −1.1596 |
| 10.00 | −0.2961 |  |  |  |  |  |

TABLE 3

Ex. 2 RESIDUAL MONOMERS WT %

| Cure Time | NVP | HEMA | TEGDMA | Norbloc | CGI 819 | OH-mPDMS |
|---|---|---|---|---|---|---|
| 0.00 | 48.687 | 6.612 | 0.493 | 2.036 | 0.211 | 36.999 |
| 0.25 | 50.127 | 5.740 | 0.377 | 1.805 | 0.167 | 33.584 |
| 0.50 | 50.053 | 4.958 | 0.303 | 1.602 | 0.129 | 29.903 |
| 1.00 | 48.037 | 3.611 | 0.185 | 1.152 | 0.067 | 22.854 |
| 2.00 | 45.327 | 1.722 | 0.072 | 0.554 | 0.020 | 11.709 |
| 4.00 | 37.315 | 0.520 | 0.030 | 0.085 | 0.002 | 3.724 |
| 6.00 | 34.959 | 0.439 | 0.027 | 0.037 |  | 3.393 |
| 8.00 | 32.155 | 0.330 | 0.021 | 0.016 |  | 2.562 |
| 10.00 | 24.624 |  |  |  |  |  |
| 12.00 | 21.977 |  |  |  |  |  |
| 15.00 | 17.041 |  |  |  |  |  |
| 20.00 | 8.579 |  |  |  |  |  |
| 30.00 | 3.241 |  |  |  |  |  |

TABLE 4

Ex. 2% Incorporation

| Cure Time | % NVP | % HEMA | % TEGDMA | % Norbloc | % CGI 819 | % OH-mPDMS |
|---|---|---|---|---|---|---|
| 0.00 | 100.00 | 100.00 | 100.00 | 100.00 | 100.00 | 100.00 |
| 0.25 | 102.96 | 86.81 | 76.49 | 88.65 | 79.13 | 90.77 |
| 0.50 | 102.81 | 74.99 | 61.35 | 78.69 | 61.15 | 80.82 |
| 1.00 | 98.67 | 54.61 | 37.56 | 56.59 | 31.64 | 61.77 |
| 2.00 | 93.10 | 26.04 | 14.55 | 27.19 | 9.44 | 31.65 |
| 4.00 | 76.64 | 7.86 | 6.10 | 4.18 | 1.04 | 10.06 |
| 6.00 | 71.80 | 6.63 | 5.45 | 1.81 |  | 9.17 |
| 8.00 | 66.04 | 4.99 | 4.15 | 0.77 |  | 6.92 |
| 10.00 | 50.58 |  |  |  |  |  |

TABLE 7

Ex. 2

| Component | Time Points | $R^2$ | Slope | k (min⁻¹) | Half-life (t½), min |
|---|---|---|---|---|---|
| NVP | 0.25-8 min | 0.973 | −0.0265 | 0.0610 | 11.36 |
| HEMA | 0.25-4 min | 0.998 | −0.2810 | 0.6471 | 1.07 |
| TEGDMA | 0.25-4 min | 0.963 | −0.2951 | 0.6796 | 1.02 |
| Norblock | 0.25-4 min | 0.993 | −0.3568 | 0.8217 | 0.84 |
| CGI 819 | 0.25-4 min | 0.999 | −0.5037 | 1.1600 | 0.60 |
| OH-mPDMS | 0.25-4 min | 0.999 | −0.2582 | 0.5946 | 1.17 |

TABLE 8

CE 2

| Component | Time Points | $R^2$ | Slope | k (min⁻¹) | Half-life (t₁/₂), min |
|---|---|---|---|---|---|
| DMA | 0.25-8 min | 0.975 | −0.1496 | 0.3445 | 2.01 |
| HEMA | 0.25-4 min | 0.978 | −0.2167 | 0.4991 | 1.39 |
| TEGDMA | 0.25-4 min | 0.971 | −0.2254 | 0.5191 | 1.34 |
| Norblock | 0.25-4 min | 0.976 | −0.1873 | 0.4314 | 1.61 |
| CGI 819 | 0.25-4 min | 0.981 | −0.3088 | 0.7112 | 0.97 |
| OH-mPDMS | 0.25-4 min | 0.988 | −0.1814 | 0.4178 | 1.66 |

TABLE 9

| | Ex.# 2 | CE2 |
|---|---|---|
| Hydrophile (HP) | NVP | DMA |
| HP ½ life | 11.36 | 2.01 |
| Si ½ life | 1.17 | 1.66 |
| HP/Si | 9.7 | 1.2 |

TABLE 9-continued

| | Ex.# | |
|---|---|---|
| | 2 | CE2 |
| [μmol HP/μmol Si] @90% conversion of Si | 55.25 | 9.27 |

In Example 2, the half-life of the NVP is nearly ten times slower (11.36 minutes) than the half-lives for the other monomers HEMA (1.07) and OH-mPDMS (1.17). In Comparative Example 1, the half-life of the DMA (2.01) is nearly the same as the half life of the silicone-containing component, OH-mPDMS (1.66). It is believed that the difference in wettability between the formulations of Example 1 and Comparative Example 1 is due to the substantially slower polymerization of the slow-reacting hydrophilic monomer in Example 1 (NVP) as compared to the hydrophilic monomer in Comparative Example 1 (DMA). Table 9 also shows that at 90% conversion of the silicone monomer, the molar ratio of the unreacted slow-reacting hydrophilic monomer NVP, compared to the unreacted silicone (mPDMS), is 55.25 for NVP, and only 9.27 for the DMA system. The NVP containing system displays improved wettability, as measured by advancing contact angle, and increased oxygen permeability. The modulus of the DMA-containing formulation was substantially lower, which is believed to be an indication that the DMA and silicone monomers are more randomly incorporated in network. NVP system is believed to have larger blocks of silicone and NVP. Moreover the ratio of the kinetic half lives for the Comparative Example 2 system containing DMA as the hydrophile (1.21) is insufficient to provide a wettable lens. The ratio of molar concentrations of DMA and HO-PDMS for Comparative Example 1 was less than 10 (9.74).

Examples 3-5 and Comparative Example 3

The preparation described in Example 1 and kinetics evaluation described in Example 2 were repeated for the formulations listed in Table 10 below. The formulations for Example 2 and Comparative Example 2 are listed in Table 10 for convenience. Tables 11-14 show a summary of the calculated kinetics data for Examples 3-5 and Comparative Example 3, and Table 15 shows the ratios of slow hydrophilic component to the silicone component. The kinetics data for Example 2 and Comparative Example 2 is shown in Tables 5 and 6, above.

TABLE 10

| Comp. | Ex. 2 | Ex. 3 | CE2 | CE 3 | Ex. 4 | Ex. 5 |
|---|---|---|---|---|---|---|
| OH-mPDMS | 40 | 40 | 40 | 40 | 0 | 0 |
| SA2 | 0 | 0 | 0 | 0 | 41 | 40 |
| NVP | 50.5 | 50.5 | 0 | 0 | 51.5 | 50.5 |
| DMA | 0 | 0 | 50.5 | 50.5 | 0 | 0 |
| HEMA | 6.75 | 8.75 | 6.75 | 8.75 | 6.75 | 6.75 |
| TEGDMA | 0.5 | 0.5 | 0.5 | 0.5 | 0.5 | 0.5 |
| Norblock | 2 | 0 | 2 | 0 | 0 | 2 |
| CGI 819 | 0.25 | 0.25 | 0.25 | 0.25 | 0.25 | 0.25 |

TABLE 11

Summary of Example 3 Kinetic Calculations

| Component | Time Points | $R^2$ | Slope | k (min$^{-1}$) | Half-life (t½), min |
|---|---|---|---|---|---|
| NVP | 0.25-4 min | 0.869 | −0.1133 | 0.2609 | 2.66 |
| HEMA | 0.25-8 min | 0.869 | −0.2911 | 0.6704 | 1.03 |
| TEGDMA | 0.25-4 min | 0.998 | −0.5114 | 1.1778 | 0.59 |
| CGI 819 | 0.25-4 min | 1.000 | −0.5228 | 1.2040 | 0.58 |
| OH-mPDMS | 0.25-2 min | 0.987 | −0.3080 | 0.7093 | 0.98 |

TABLE 12

Summary of Comparative Example 3 Kinetics Calculations

| Component | Time Points | $R^2$ | Slope | k (min$^{-1}$) | Half-life (t½), min |
|---|---|---|---|---|---|
| DMA | 0.25-2 min | 0.993 | −0.1736 | 0.3998 | 1.73 |
| HEMA | 0.25-1 min | 0.989 | −0.3734 | 0.8599 | 0.81 |
| TEGDMA | 0.25-2 min | 0.993 | −0.5279 | 1.2158 | 0.57 |
| CGI 819 | 0.25-2 min | 0.991 | −0.5106 | 1.1759 | 0.59 |
| OH-mPDMS | 0.25-1 min | 0.987 | −0.3262 | 0.7512 | 0.92 |

TABLE 13

Summary of Example 4 Kinetics Calculations

| Component | Time Points | $R^2$ | Slope | k (min$^{-1}$) | Half-life (t½), min |
|---|---|---|---|---|---|
| NVP | 0.25 - 1 min | 0.944 | −0.1839 | 0.4235 | 1.64 |
| HEMA | 0.25 - 2 min | 0.970 | −1.1455 | 2.6381 | 0.26 |
| TEGDMA | 0.25 - 2 min | 0.942 | −1.0470 | 2.411 | 0.29 |
| CGI 819 | 0.25 - 4 min | 0.959 | −0.3555 | 0.8187 | 0.85 |
| SA2 | 0.25 - 2 min | 0.913 | −0.7599 | 1.7500 | 0.40 |

TABLE 14

Summary of Example 5 Kinetics Calculations

| Component | Time Points | $R^2$ | Slope | k (min$^{-1}$) | Half-life (t½), min |
|---|---|---|---|---|---|
| NVP | 0.25 - 1 min | 0.891 | −0.0630 | 0.1451 | 4.78 |
| HEMA | 0.25 - 2 min | 0.947 | −1.2118 | 2.7908 | 0.25 |
| TEGDMA | 0.25 - 2 min | 0.886 | −2.1365 | 4.9204 | 0.14 |
| Norbloc | 0.25 - 2 min | 0.981 | −1.4710 | 3.3877 | 0.20 |
| CGI 819 | 0.25 - 2 min | 0.988 | −0.4677 | 1.0771 | 0.64 |
| SA2 | 0.25 - 2 min | 0.712 | −0.4544 | 1.0465 | 0.66 |

TABLE 15

| | Ex. # | | | | | |
|---|---|---|---|---|---|---|
| | 2 | 3 | CE2 | CE3 | 4 | 5 |
| Norbloc | Y | N | Y | N | N | Y |
| Hydrophile | NVP | NVP | DMA | DMA | NVP | NVP |
| HP ½ life | 11.36 | 2.66 | 2.01 | 1.73 | 1.64 | 4.78 |
| Silicone | HO-mPDMS | HO-mPDMS | HO-mPDMS | HO-mPDMS | SA2 | SA2 |
| Si ½ life | 1.17 | 0.98 | 1.66 | 0.92 | 0.4 | 0.66 |
| HP/Si | 9.7 | 2.7 | 1.2 | 1.88 | 4.1 | 7.24 |
| [μmol HP/μmol Si] @90% conversion | 55.25 | 40.21 | 9.27 | 8.99 | 55.79 | 60.23 |

Considering the data in Table 15, including a UV absorbing compound in a photoinitiated reactive monomer mixture causes the half life of the slow-reacting hydrophilic monomer NVP to increase by between 60 and 400%, while the half life of DMA increases marginally from 1.73 to 2.01 (16%). The half life of the HO-mPDMS was also increased. The half life of the SA2 silicone decreased upon addition of the UV absorber, Norbloc, but the decrease was not enough to offset the substantial increase in the half life of the NVP. Comparing Comparative Example 2 (formulation containing DMA and Norbloc) to Comparative Example 3 (formulation containing DMA without Norbloc), it can be seen that the inclusion of Norbloc in a DMA-containing formulation slowed the reaction rate for the crosslinker TEGDMA and more than doubled its half life. In the DMA/Norbloc-containing formulation, this meant that the crosslinker had a reactivity rate much more similar to the hydrophilic monomer and silicone-containing component. Even though the inclusion of a UV absorber such as Norbloc slowed the reaction rate for TEGDMA, it was still faster (4.92) than both the hydrophilic monomer (0.145) and silicone-containing component (1.05).

Contact lenses were made from the Formulations of Examples 3-5 and Comparative Example 3 using the method described in Example 2. The properties of the lenses were measured and are shown in Table 16, below.

TABLE 16

| Ex. # | % $H_2O$ | % Haze | DCA | Mechanicals Mod. (psi) | Elong. (%) | Dk |
|---|---|---|---|---|---|---|
| 2 | 58.4 (0.2) | 4 (0) | 44 (4) | 103 (11) | 220 (36) | 75 |
| 3 | 66.6 (0.1) | 24 (1) | 50 (3) | 63 (8) | 192 (76) | 79 |
| CE2 | 59.8 (0.1) | 5 (1) | 127 (14) | 54 (7) | 227 (52) | 49 |
| CE3 | 58.1 (0.2) | 3 (1) | 132 (7) | 78 (7) | 199 (39) | 49 |
| 4 | 67 (0.2) | 67 (2) | 51 (3) | 64 (7) | 229 (97) | 82 |
| 5 | 65.5 (0.1) | 8 (1) | 68 (7) | 105 (9) | 242 (49) | 57 |

The lenses of Examples 2 through 5 show desirable haze and wettability, as well as a balance of other desirable properties. Each of these Examples had ratios of the slow-reacting hydrophilic monomer half life:silicone-containing component half life greater than about 2. Comparative Examples 2 and 3 had half life ratios of below 2 (1.2 and 1.88 respectively). Thus, half life ratios greater than about 2, and in some embodiments greater than about 3 are desirable to provide desirable wettability.

Comparing the modulii of Comparative Example 2 (54 psi, with Norbloc) and Comparative Example 3 (78 psi without Norbloc) it can be seen that the change in the reactivity rate for TEGDMA caused by the inclusion of Norbloc was sufficient to decrease crosslinking in the network of the resulting polymer. Thus, in additional to changing the amount of crosslinker, one can also choose a crosslinker with a different reactivity ratio to achieve a desired polymer structure and modulus. The same behavior is also observed comparing the SA2/NVP-containing formulations of Examples 4 and 5.

Examples 6-7

Example 1 and 2 were repeated except the amount of initiator was increased to 0.5 and 0.75%, respectively and the amount of NVP was decreased. The kinetics of each of the formulations was measured and calculated as described in Example 1, and lenses were made as described in Example 2. The kinetics results are shown in Tables 17 through 19 and the lens properties are shown in Table 19a.

TABLE 17

Example 6: 0.50% CGI 819

| Component | Time Points | $R^2$ | Slope | k (min$^{-1}$) | Half-life (t½), min |
|---|---|---|---|---|---|
| NVP | 0.25 - 6 min | 0.956 | −0.0502 | 0.1156 | 5.99 |
| HEMA | 0.25 - 4 min | 0.941 | −0.3357 | 0.7731 | 0.90 |
| TEGDMA | 0.25 - 2 min | 0.997 | −0.6348 | 1.4619 | 0.47 |
| Norbloc | 0.25 - 4 min | 0.996 | −0.5534 | 1.2745 | 0.54 |
| CGI 819 | 0.25 - 4 min | 0.999 | −0.4902 | 1.1289 | 0.61 |
| OH-mPDMS | 0.25 - 2 min | 0.994 | −0.4720 | 1.0870 | 0.64 |

TABLE 18

Example 7, 0.75% CGI 819

| Component | Time Points | $R^2$ | Slope | k (min$^{-1}$) | Half-life (t½), min |
|---|---|---|---|---|---|
| NVP | 0.25 - 4 min | 0.995 | −0.0511 | 0.1177 | 5.89 |
| HEMA | 0.25 - 4 min | 0.930 | −0.3754 | 0.8645 | 0.80 |
| TEGDMA | 0.25 - 2 min | 0.976 | −0.6392 | 1.4721 | 0.47 |
| Norblock | 0.25 - 4 min | 0.984 | −0.9843 | 2.2668 | 0.31 |
| CGI 819 | 0.25 - 4 min | 0.998 | −0.4357 | 1.0034 | 0.69 |
| OH-mPDMS | 0.25 - 4 min | 0.998 | −0.3688 | 0.8493 | 0.82 |

TABLE 19

| | Ex.# 2 | Ex.# 6 | Ex.# 7 |
|---|---|---|---|
| CGI819 | 0.25 | 0.5 | 0.75 |
| NVP ½ life | 11.36 | 5.99 | 5.89 |
| Si ½ life | 1.17 | 0.64 | 0.82 |
| HP/Si | 9.7 | 9.4 | 7.2 |
| [μmol HP]/[μmol Si] @90% conversion | 55.25 | 56.05 | 56.40 |

TABLE 19a

| Ex. # | % $H_2O$ | % Haze | DCA | Mechanicals Mod. (psi) | Elong. (%) | Dk |
|---|---|---|---|---|---|---|
| 2 | 58.4 (0.2) | 4 (0) | 44 (4) | 102.9 (11.4) | 220.3 (36.2) | 74.7 |
| 6 | 62.4 (0) | 3 (0) | 45 (6) | 76.3 (6.7) | 202.9 (55.2) | 61.7 |
| 7 | 65.3 (0.2) | 4 (0) | 69 (11) | 58.5 (6.5) | 198.3 (49.8) | 78.1 |

Changing the initiator concentration from 0.25 (Ex. 2) to 0.5 (Ex. 6) had relatively little effect on the half life ratio of slow-reacting hydrophilic monomer to silicone-containing component in the formulations or the ratio of the concentrations of the slow-reacting hydrophilic monomer and silicone-containing components at 90% conversion. Increasing the initiator concentration to 0.75 wt % (Ex. 75) did measurably change the half life ratio of slow-reacting hydrophilic monomer to silicone-containing component but had a negligble effect on the ratio of the concentrations of the slow-reacting hydrophilic monomer and silicone-containing components at 90% conversion. The lenses of Example 7 displayed acceptable properties including haze and advancing contact angle.

Examples 8-12

The level of BHT and initiator was varied as shown in Table 20. In Example 10 2 wt % VINAL, was added to the formulation of Example 8.

TABLE 20

| | Ex# | | | | |
|---|---|---|---|---|---|
| | 8 | 9 | 10 | 11 | 12 |
| [BHT] ug/g | 1429 | 166 | 166 | 166 | 1429 |
| mPDMS 1000 | 15 | 15 | 15 | 15 | 15 |
| OH-mPDMS, n = 4 | 25 | 25 | 25 | 25 | 25 |
| NVP | 50.5 | 50.5 | 50.38 | 50.25 | 48.5 |
| HEMA | 6.75 | 6.75 | 6.75 | 6.75 | 6.54 |
| VINAL | 0 | 0 | 0 | 0 | 2 |
| TEGDMA | 0.5 | 0.5 | 0.5 | 0.5 | 0.5 |
| Norbloc | 2 | 2 | 2 | 2 | 2 |
| CGI 819 | 0.25 | 0.25 | 0.37 | 0.5 | 0.25 |

The kinetics for the two formulations were measured and calculated as described in Example 1, and contact lenses were made as described in Example 2. The kinetics for the formulations are shown in Tables 21-26, and the lens properties are shown in Table 25.

TABLE 21

Example 8

| Component | Time Points | $R^2$ | Slope | k (min$^{-1}$) | Half-life (t½), min |
|---|---|---|---|---|---|
| NVP | 0.25 - 8 min | 0.975 | −0.0267 | 0.0615 | 11.27 |
| HEMA | 0.25 - 4 min | 0.993 | −0.2044 | 0.4707 | 1.47 |
| TEGDMA | 0.25 - 2 min | 0.947 | −0.3171 | 0.7303 | 0.95 |
| Norblock | 0.25 - 4 min | 0.999 | −0.2441 | 0.5622 | 1.23 |
| CGI 819 | 0.25 - 4 min | 1.000 | −0.5438 | 1.2524 | 0.55 |
| OH-mPDMS | 0.25 - 4 min | 0.997 | −0.1885 | 0.4341 | 1.60 |
| mPDMS 1000 | 0.25 - 4 min | 0.997 | −0.1515 | 0.3489 | 1.99 |

TABLE 22

Example 9

| Component | Time Points | $R^2$ | Slope | k (min$^{-1}$) | Half-life (t½), min |
|---|---|---|---|---|---|
| NVP | 0.25 - 8 min | 0.989 | −0.0294 | 0.0677 | 10.24 |
| HEMA | 0.25 - 4 min | 0.997 | −0.2527 | 0.5820 | 1.19 |
| TEGDMA | 0.25 - 2 min | 0.989 | −0.4923 | 1.1338 | 0.61 |
| Norblock | 0.25 - 4 min | 0.999 | −0.3536 | 0.8143 | 0.85 |
| CGI 819 | 0.25 - 4 min | 1.000 | −0.5228 | 1.2040 | 0.58 |
| OH-mPDMS | 0.25 - 4 min | 0.999 | −0.2499 | 0.5755 | 1.20 |
| mPDMS 1000 | 0.25 - 2 min | 0.996 | −0.1474 | 0.3395 | 2.04 |

TABLE 23

Example 10

| Component | Time Points | $R^2$ | Slope | k (min$^{-1}$) | Half-life (t½), min |
|---|---|---|---|---|---|
| NVP | 0.25 - 8 min | 0.990 | −0.0381 | 0.0877 | 7.90 |
| HEMA | 0.25 - 4 min | 0.985 | −0.3395 | 0.7819 | 0.89 |
| TEGDMA | 0.25 - 4 min | 0.946 | −0.3549 | 0.8173 | 0.85 |
| Norblock | 0.25 - 4 min | 0.980 | −0.5042 | 1.1612 | 0.60 |
| CGI 819 | 0.25 - 4 min | 0.999 | −0.4793 | 1.1038 | 0.63 |
| OH-mPDMS | 0.25 - 4 min | 0.989 | −0.3222 | 0.7420 | 0.93 |
| mPDMS 1000 | 0.25 - 4 min | 0.993 | −0.2765 | 0.6368 | 1.09 |

TABLE 24

Example 11

| Component | Time Points | $R^2$ | Slope | k (min$^{-1}$) | Half-life (t½), min |
|---|---|---|---|---|---|
| NVP | 0.25 - 8 min | 0.887 | −0.0611 | 0.1407 | 4.92 |
| HEMA | 0.25 - 4 min | 0.924 | −0.4627 | 1.0656 | 0.65 |
| TEGDMA | 0.25 - 4 min | 0.852 | −0.4986 | 1.1483 | 0.60 |
| Norblock | 0.25 - 4 min | 0.985 | −0.6741 | 1.5525 | 0.45 |
| CGI 819 | 0.25 - 4 min | 1.000 | −0.4326 | 0.99628 | 0.70 |
| OH-mPDMS | 0.25 - 4 min | 0.940 | −0.4831 | 1.1126 | 0.62 |
| mPDMS 1000 | 0.25 - 4 min | 0.989 | −0.4703 | 1.0831 | 0.64 |

TABLE 25

Example 12

| Component | Time Points | $R^2$ | Slope | k (min$^{-1}$) | Half-life (t1/2), min |
|---|---|---|---|---|---|
| VINAL | 0.25 - 18 min | 0.904 | −0.0126 | 0.0290 | 23.88 |
| NVP | 0.25 - 8 min | 0.949 | −0.0273 | 0.0629 | 11.02 |
| HEMA | 0.25 - 2 min | 0.979 | −0.3082 | 0.7098 | 0.98 |
| TEGDMA | 0.25 - 2 min | 0.984 | −0.4253 | 0.9795 | 0.71 |
| Norblock | 0.25 - 2 min | 0.975 | −0.2924 | 0.6734 | 1.03 |
| CGI 819 | 0.25 - 4 min | 1.000 | −0.4882 | 1.1243 | 0.62 |
| OH-mPDMS | 0.25 - 2 min | 0.971 | −0.2819 | 0.6492 | 1.07 |
| mPDMS 1000 | Not Measured | | | | |

TABLE 26

| | Ex.# | | | | |
|---|---|---|---|---|---|
| | 8 | 9 | 10 | 11 | 12 |
| [BHT] ug/g | 9324 | 901 | 901 | 901 | 9324 |
| [CGI 819] | 0.25 | 0.25 | 0.37 | 0.5 | 0.25 |
| NVP ½ life | 11.27 | 10.24 | 7.90 | 4.92 | 11.02 |
| mPDMS ½ life | 1.99 | 2.04 | 1.09 | 0.64 | ** |
| OH-mPDMS ½ life | 1.60 | 1.02 | 0.93 | 0.62 | 1.07 |
| NVP/MPDMS | 5.7 | 5.0 | 7.3 | 7.7 | ** |
| NVP/OH-mPDMS | 7.0 | 8.5 | 8.5 | 7.9 | 10.3 |
| VINAL/HO-PDMS | ** | ** | ** | ** | 22.3 |
| [μmol NVP]/[μmol mPDMS] @90% conversion | 211.45 | 233.18 | 273.5 | 251.9 | XX |
| [μmol NVP]/[μmol HO-mPDMS] @90% conversion | 94.71 | 83.6 | 92 | 99 | 68.57 |

**Not applicable
XX not measured.

TABLE 27

| | Ex. # | | | | |
|---|---|---|---|---|---|
| | 8 | 9 | 10 | 11 | 12 |
| % H$_2$O | 59.1 (0.1) | 60.0 (0.2) | 61.3 (0.2) | 63.6 (0.2) | 61.3 (0.2) |
| % Haze | 3 (1) | 5 (1) | 4 (1) | 5 (0) | NT |
| DCA | 49 (2) | 47 (3) | 52 (4) | 56 (5) | 51 (3) |
| Mod. (psi) | 92 (10) | 84 (10) | 65 (9) | 66 (7) | 84 (12) |
| Elong. (%) | 188 (67) | 194 (64) | 197 (25) | 163 (61) | 149 (61) |
| Dk | 86.7 | 90.7 | 82.8 | 82.3 | 90.4 |
| Lipocalin (μg/lens) | 3.16 (0.6) | 3.37 (0.2) | NT | NT | 2.98 (0.3) |
| Total lipids (μg/lens) | 22.7 (2.9) | 23 (1.9) | NT | NT | 13.2 (1.9) |
| Lysozyme (μg/Lens) | 5.6 (0.9) | NT | NT | NT | 39 (6.2) |

TABLE 27-continued

| | Ex. # | | | | |
|---|---|---|---|---|---|
| | 8 | 9 | 10 | 11 | 12 |
| Lysozyme Activity (%) | 68 (2.7) | NT | NT | NT | 78.7 (2.5) |
| PQ1 Uptake (μg/mL) | 7.4 (0.4) | NT | NT | NT | 7.1 (0.1) |

All the lenses of Examples 8-12 have half life ratios greater than about 5, and all display desirably low advancing contact angles (less than 60°), very low haze (less than 10) and desirable oxygen permeabilities greater than 80. The lenses of Examples 8-12 also have concentration ratios of the slow-reacting hydrophilic monomer to the silicone-containing components at 90% conversion of greater than about 83. Comparing Examples 8 and 9 shows that decreasing the inhibitor concentration from 1429 ng/g to 166 ng/g reduces the modulus slightly, but has a negligible impact on the other measured lens properties. Comparing Examples 9-11, decreases both the modulus and the Dk and increases the water content of the resultant lenses, particularly comparing Examples 9 and 11. This would suggest that the incorporation of the HO-PDMS is having a larger effect on the Dk than the incorporation of the mPDMS, as the kinetic ratio of NVP to HO-PDMS is trending in the same direction as the Dk for Examples 9-11.

Examples 13-15

The preparation described in Example 1 and kinetics evaluation described in Example 2 were repeated for the formulations listed in Table 28 below. Tables 29-30 show a summary of the calculated kinetics data for Examples 13-14, and Table 31 shows the ratios of slow-reacting hydrophilic monomer to the silicone-containing component. Lens properties are shown in Table 32.

TABLE 28

| Component wt % | 13 | 14 | CE4 |
|---|---|---|---|
| SA2 | 40 | 40 | 40 |
| GMMA | 57.25 | 57.25 | 0 |
| EGVE | 0 | 0 | 57.25 |
| TEGDMA | 0.5 | 0.5 | 0.5 |
| Norbloc | 2 | 2 | 2 |
| CGI 819 | 0.25 | 0.25 | 0.25 |
| Diluent (TAA) | 0 | 20 | 0 |

TABLE 29

Example 13

| Component | Time Points | $R^2$ | Slope | k (min$^{-1}$) | Half-life (t½), min |
|---|---|---|---|---|---|
| GMMA | 0.033 - 0.5 min | 0.849 | −1.8339 | 4.2235 | 0.16 |
| TEGDMA | 0.033 - 0.5 min | 0.825 | −1.9297 | 4.4441 | 0.16 |
| Norbloc | 0.033 - 0.5 min | 0.834 | −1.8209 | 4.1935 | 0.17 |
| CGI 819 | 0.033 - 1 min | 0.980 | −0.3888 | 0.8954 | 0.77 |
| SA2 | 0.083 - 0.75 min | 0.776 | −0.8522 | 1.9626 | 0.35 |

TABLE 30

Example 14

| Component | Time Points | $R^2$ | Slope | k (min$^{-1}$) | Half-life (t½), min |
|---|---|---|---|---|---|
| EGVE | 0.25 - 6 min | 0.944 | −0.0138 | 0.03178 | 21.81 |
| TEGDMA | 0.25 - 1 min | 0.974 | −0.8791 | 2.02457 | 0.34 |
| Norbloc | 0.25 - 4 min | 0.990 | −0.4128 | 0.95068 | 0.73 |
| CGI 819 | 0.25 - 4 min | 0.994 | −0.3326 | 0.76598 | 0.90 |
| SA2 | 0.25 - 4 min | 0.994 | −0.3630 | 0.83599 | 0.83 |

TABLE 31

| | 13 | 14 | 15 |
|---|---|---|---|
| HP | GMMA | GMMA | EGVE |
| HP ½ life | 0.16 | NC | 21.81 |
| SA2 ½ life | 0.35 | NC | 0.83 |
| HP/SA2 | 0.46 | NC | 26.3 |
| [μmol HP]/[μmol SA2] @90% conversion | 1.8 | NC | 93.9 |

TABLE 32

| | Ex. # | | |
|---|---|---|---|
| | 13 | 14 | 15 |
| % H₂O | 56.5 (0.1) | 60.7 (0.3) | NT |
| % Haze | 89 (8) | 15 (1) | NT |
| DCA | 131 (9) | 123 (7) | NT |
| Mod. (psi) | NT | 137 (19) | NT |
| Elong. (%) | NT | 147 (51) | NT |
| Dk | 37.5 | 41.2 | NT |

In Example 13, the hydrophilic component, GMMA, cures much faster than the silicone-containing component, SA2, yielding a kinetic half life ratio of 0.45. Lenses made from the formulation of Example 13 had an advancing contact angle of 131°, which were very unwettable and a Dk of only 37.5. Example 13 shows that it is not enough for the kinetic rates of the hydrophile and the silicone containing component to be different, at least one hydrophile must be slower to get the desired properties described in the present invention. Example 14 shows that the inclusion of a diluent in the reactive mixture improved the haze without substantially changing the water content, advancing contact angle or Dk. Example 15 showed a kinetic ratio of 26.3, however, lenses made from this formulation were not fully cured within the 18 minute cure time and lens properties were not measured.

Examples 16-18

The preparation and kinetics evaluation described in Examples 1 and 2 were repeated for the formulations listed in Table 35 below. Tables 36-38 show a summary of the calculated kinetics data for Examples 16-18, and Table 39 shows the ratios of slow hydrophilic component to the silicone component.

TABLE 35

| Component | 16 | 17 | 18 |
|---|---|---|---|
| mPDMS 1000 | 15.00 | 15.00 | 15.00 |
| OH-mPDMS, n = 4 | 25.00 | 25.00 | 25.00 |

TABLE 35-continued

| Component | 16 | 17 | 18 |
|---|---|---|---|
| VMA | 50.25 | 49.75 | 52.25 |
| HEMA | 6.75 | 6.75 | 6.75 |
| TEGDMA | 0.50 | 0.50 | 0.50 |
| Norbloc | 2.00 | 2.00 | 0.00 |
| CGI 819 | 0.50 | 1.00 | 0.50 |

TABLE 36

Example 16, 0.5% CGI 819

| Component | Time Points | $R^2$ | Slope | k (min$^{-1}$) | Half-life (t½), min |
|---|---|---|---|---|---|
| VMA | 0.25 - 6 min | 0.963 | −0.0111 | 0.0256 | 27.11 |
| HEMA | 0.25 - 10 min | 0.954 | −0.2126 | 0.4896 | 1.42 |
| TEGDMA | 0.25 - 10 min | 0.734 | −0.0864 | 0.1990 | 3.48 |
| Norbloc | 0.25 - 6 min | 0.981 | −0.3048 | 0.7020 | 0.99 |
| CGI 819 | 0.25 - 4 min | 0.996 | −0.3056 | 0.7038 | 0.98 |
| OH-mPDMS | 0.25 - 10 min | 0.949 | −0.1878 | 0.4325 | 1.60 |
| mPDMS 1000 | 0.25 - 4 min | 0.991 | −0.1085 | 0.2499 | 2.77 |

TABLE 37

Example 17, 1% CGI 819

| Component | Time Points | $R^2$ | Slope | k (min$^{-1}$) | Half-life (t1/2), min |
|---|---|---|---|---|---|
| VMA | 0.25 - 6 min | 0.925 | −0.0134 | 0.0309 | 22.46 |
| HEMA | 0.25 - 6 min | 0.999 | −0.3642 | 0.8388 | 0.83 |
| TEGDMA | 0.25 - 4 min | 0.495 | −0.0735 | 0.1693 | 4.09 |
| Norblock | 0.25 - 4 min | 0.998 | −0.4342 | 1.0000 | 0.69 |
| CGI 819 | 0.25 - 4 min | 0.998 | −0.3398 | 0.7826 | 0.89 |
| OH-mPDMS | 0.25 - 6 min | 0.998 | −0.3185 | 0.7335 | 0.94 |
| mPDMS 1000 | 0.25 - 10 min | 0.944 | −0.1860 | 0.4284 | 1.62 |

TABLE 38

Example 18, No Norbloc

| Component | Time Points | $R^2$ | Slope | k (min$^{-1}$) | Half-life (t½), min |
|---|---|---|---|---|---|
| VMA | 0.25 - 10 min | 0.852 | −0.0247 | 0.0569 | 12.18 |
| HEMA | 0.25 - 8 min | 0.999 | −0.2553 | 0.5880 | 1.18 |
| TEGDMA | 0.25 - 2 min | 0.998 | −0.4201 | 0.9675 | 0.72 |
| CGI 819 | 0.25 - 2 min | 0.999 | −0.3280 | 0.7554 | 0.92 |
| OH-mPDMS | 0.25 - 8 min | 0.999 | −0.2252 | 0.5186 | 1.34 |
| mPDMS 1000 | 0.25 - 10 min | 0.989 | −0.1637 | 0.3770 | 1.84 |

TABLE 39

| | 16 | 17 | 18 |
|---|---|---|---|
| [CGI] | 0.5 | 1 | 0.5 |
| [Norbloc] | 2 | 2 | 0 |
| VMA ½ life | 27.11 | 22.46 | 12.18 |
| mPDMS ½ life | 2.77 | 1.62 | 1.84 |
| HO-mPDMS ½ life | 1.6 | 0.94 | 1.34 |
| VMA/mPDMS | 9.8 | 13.9 | 6.6 |
| VMA/HO-mPDMS | 16.9 | 23.9 | 9.1 |
| [μmol VMA]/[μmol mPDMS] @90% conversion | 287.9 | 298.2 | 311.9 |
| [μmol VMA]/[μmol HOPDMS] @90% conversion | 110.2 | 112.1 | 116.4 |

TABLE 40

| Ex# | % H$_2$O | % Haze | DCA | Mechanicals Mod. (psi) | Elong. (%) | Dk |
|---|---|---|---|---|---|---|
| 16 | 66.0 (0.2) | 25 (1) | NT | NT | NT | 103.9 |
| 17 | 77.9 (0.2) | NT | 64 (10) | 19.0 (2.9) | 161.3 (57.8) | |
| 18 | 84.0 (0.1) | NT | NT | NT | NT | 119.6 |

The formulations of Examples 16-18 all made very wettable contact lenses. Examples 16 and 18 displayed Dk greater than 100 and water contents greater than 60%. All lenses felt flimsy upon handling, which is evidenced by the modulus of 19 for Example 17. The inclusion of Norbloc in the VMA systems substantially (>300%,) slowed the kinetic rate of the crosslinker, TEGDMA (from 0.967 for Example 18, without Norbloc to 0.199 for Example 16 with Norbloc). The kinetic rate of the crosslinker in Example 18 (no UV absorber) was faster than the silicone components but slower than the silicones in Example 16 (UV absorber).

Comparing Examples 16 and 17, increasing the amount of intiator in the formulation provided a significant increase in the kinetic ratios for both HO-PDMS and mPDMS. Comparing Example 16 (UV absorber) to Example 18 (no UV absorber), shows that the inclusion of Norbloc slows the kinetic rate of the VMA by more 100%, and decreases the kinetic half life. The influence on the kinetics of the silicone components were not nearly as substantially impacted.

The properties of the lenses can be improved by improving the efficiency in the incorporation of the slow components. In addition to optimizing the level of the initiator and UV absorber and cure conditions (cure intensity, cure temperature and oxygen level), the concentration and chemistry of the crosslinker(s) can significantly affect the overall cure efficiency. Crosslinkers with two or more functional groups in which at least one group is fast curing or a mixture of crosslinkers having varying cure rates can improve the cure efficiency. Thus, crosslinkers with at least one functional group (e.g. vinyl, allyl; HEMAVc) which is slow curing compared to the silicone components may be used as the sole crosslinker or in a mixture with at least one additional crosslinker can improve the efficiency in the incorporation of the slow curing hydrophile. Fast curing crosslinkers with at least two reactive groups in which at least two of the reactive groups are fast curing (e.g. acryloxy; acPDMS) can improve the efficiency in the cure of the crosslinkers and silicones.

Comparative Examples 4-6

Comparative Examples 2 and 3 were repeated except that the formulations were changed to add a high molecular weight wetting agent PVP, as shown in Table 41. The cure intensity was 4-5 mW/cm$^2$. The preparation and kinetics evaluation described in Comparative Examples 2 and 3 were repeated. Tables 42-44 show a summary of the calculated kinetics data for Comparative Examples 4-6. Table 45 shows the ratios of slow hydrophilic component to the silicone component and Table 46 shows the lenses properties.

TABLE 41

| Component | CE2 | CE3 | CE4 | CE5 | CE6 |
|---|---|---|---|---|---|
| OH-mPDMS, n = 4 | 40.00 | 40.00 | 40.00 | 40.00 | 40.00 |
| DMA | 50.50 | 50.50 | 44.50 | 44.50 | 42.50 |

TABLE 41-continued

| Component | CE2 | CE3 | CE4 | CE5 | CE6 |
|---|---|---|---|---|---|
| HEMA | 6.75 | 8.75 | 8.75 | 6.75 | 8.75 |
| TEGDMA | 0.50 | 0.50 | 0.50 | 0.50 | 0.50 |
| Norbloc | 2.00 | 0.00 | 0.00 | 2.00 | 2.00 |
| PVP K90 | 0.00 | 0.00 | 6.00 | 6.00 | 6.00 |
| CGI 819 | 0.25 | 0.25 | 0.25 | 0.25 | 0.25 |

TABLE 45

|  | CE2 | CE3 | CE4 | CE5 | CE6 |
|---|---|---|---|---|---|
| DMA ½ life | 2.01 | 1.73 | 0.71 | 0.97 | 1.05 |
| HO-mPDMS ½ life | 1.66 | 0.92 | 0.45 | 0.71 | 0.79 |
| DMA ½ life/HO-mPDMS ½ life | 1.2 | 1.9 | 1.6 | 1.4 | 1.3 |
| [µmol DMA]/[µmol HOPDMS] @90% conversion of HOPDMS | 9.3 | 9 | 10.9 | 7.0 | 3.6 |

TABLE 46

| Ex # | % $H_2O$ | % Haze | DCA | Mechanicals Mod. (psi) | Elong. (%) | Dk |
|---|---|---|---|---|---|---|
| CE2 | 59.8 (0.1) | 5 (1) | 127 (14) | 54.1 (7.4) | 227.3 (52.3) | 48.5 |
| CE3 | 58.1 (0.2) | 3 (1) | 132 (7) | 78.1 (6.9) | 198.6 (39.4) | 49.2 |
| CE4 | 63.0 (0.2) | 10 (0) | 107 (6) | 42.8 (3.8) | 271.0 (61.0) | 53.4 |
| CE5 | 62.0 (0.3) | 547 (1) | 121 (7) | 47.3 (4.8) | 274.1 (71.3) | 56.5 |
| CE6 | 58.7 (0.3) | 7 (0) | 99 (7) | 74.6 (6.3) | 242.3 (35.6) | 49.8 |

All of the formulations other than Comparative Example 5 displayed very low haze values. All of the kinetic rate ratios are well below 3. Comparative Examples 2 and 3 contain no PVP, and based upon the present invention it was expected that they would display poor in vitro wettability as measured by advancing contact angle. Comparative Examples 4-6 contain 6 wt % PVP, a wetting agent known to be effective at improving wettability. However, the advancing contact angles for Comparative Examples 4-6 are not substantially better than those for Comparative Examples 2-3.

Comparative Example 7

Comparative Example 6 was repeated at an intensity of 0.9 mW/cm$^2$. The kinetics calculations are shown in Table 47. The half-life ratio of DMA:OH-mPDMS was 1.3 and the advancing contact angle was 114.

TABLE 42

Comparative Example 4

| Component | Time Points | $R^2$ | Slope | k (min$^{-1}$) | Half-life (t½), min |
|---|---|---|---|---|---|
| DMA | 0.25 - 4 min | 0.915 | −0.4257 | 0.9804 | 0.71 |
| HEMA | 0.25 - 4 min | 0.876 | −0.4703 | 1.0831 | 0.64 |
| TEGDMA | 0.25 - 2 min | 0.962 | −0.8083 | 1.8615 | 0.37 |
| CGI 819 | 0.25 - 1 min | 0.998 | −0.5913 | 1.3618 | 0.51 |
| OH-mPDMS | 0.25 - 2 min | 0.975 | −0.6646 | 1.5306 | 0.45 |

TABLE 43

Comparative Example 5

| Component | Time Points | $R^2$ | Slope | k (min$^{-1}$) | Half-life (t½), min |
|---|---|---|---|---|---|
| DMA | 0.25 - 4 min | 0.894 | −0.3113 | 0.7169 | 0.97 |
| HEMA | 0.25 - 2 min | 0.744 | −0.5696 | 1.3118 | 0.53 |
| TEGDMA | 0.25 - 1 min | 0.988 | −1.4805 | 3.4096 | 0.20 |
| Norbloc | 0.25 - 1 min | 0.947 | −1.1100 | 2.5563 | 0.27 |
| CGI 819 | 0.25 - 2 min | 0.958 | −0.4512 | 1.0391 | 0.67 |
| OH-mPDMS | 0.25 - 2 min | 0.635 | −0.4243 | 0.9771 | 0.71 |

TABLE 44

Comparative Example 6

| Component | Time Points | $R^2$ | Slope | k (min$^{-1}$) | Half-life (t½), min |
|---|---|---|---|---|---|
| DMA | 0.25 - 1; 6 min | 0.961 | −0.2858 | 0.6582 | 1.05 |
| HEMA | 0.25 - 2 min | 0.775 | −0.5679 | 1.3079 | 0.53 |
| TEGDMA | 0.25 - 0.75 min | 1.000 | −0.7276 | 1.6757 | 0.41 |
| Norbloc | 0.25 - 2 min | 0.719 | −0.4515 | 1.0398 | 0.67 |
| CGI 819 | 0.25 - 1 min | 0.988 | −0.4852 | 1.1174 | 0.62 |
| OH-mPDMS | 0.25 - 2 min | 0.659 | −0.3786 | 0.8719 | 0.79 |

TABLE 47

Comparative Example 7, 0.9 mW/cm$^2$

| Component | Time Points | $R^2$ | Slope | k (min$^{-1}$) | Half-life (t½), min |
|---|---|---|---|---|---|
| DMA | 0.25 - 4 min | 0.914 | −0.1206 | 0.2777 | 2.50 |
| HEMA | 0.25 - 2 min | 0.987 | −0.1742 | 0.4012 | 1.73 |
| TEGDMA | 0.25 - 6 min | 0.996 | −0.2155 | 0.4963 | 1.40 |
| Norbloc | 0.25 - 4 min | 0.984 | −0.1388 | 0.3196 | 2.17 |
| CGI 819 | 0.25 - 6 min | 0.868 | −0.0279 | 0.0643 | 10.79 |
| OH-mPDMS | 0.25 - 6 min | 0.976 | −0.1567 | 0.3609 | 1.92 |

Examples 19-22

The effect of thermal initiation (Examples 21-22) and photoinitiation (Examples 19-20) on the ratio of the hydrophilic monomer to the hydrophobic monomers and the cure time was evaluated on the formulations shown in Table 48. The kinetics for Examples 19 and 20 were evaluated as in Example 1 and lenses of Examples 21 and 22 were made and evaluated as in Example 2. The kinetics for Examples 21 and 22 were evaluated as in Example 1, except the light source was turned off and samples were generated at 50-55° C., at the following time points: 0 hour to 5.00 hours in 0.25 hour increments; and from 5.00 hours to 8.00 hours in 0.50 hour increments. The kinetics are shown in Tables 49-52, and the lens properties are shown in Table 53. The lenses of Examples 19 and 20 were cured at a temperature of about 55° C. for 24 hours.

TABLE 48

| Component | Ex. 19 | Ex. 20 | Ex. 21 | Ex. 22- |
|---|---|---|---|---|
| mPDMS 1000 | 19.50 | 19.50 | 19.50 | 19.50 |
| TRIS | 19.50 | 19.50 | 19.50 | 19.50 |
| NVP | 47.88 | 47.88 | 47.88 | 47.88 |
| HEMA | 10.75 | 10.37 | 10.75 | 10.37 |
| TEGDMA | 2.00 | 2.00 | 2.00 | 2.00 |
| CGI 819 | 0.37 | 0.75 | 0.00 | 0.00 |
| AIBN | 0.00 | 0.00 | 0.37 | 0.75 |
| Diluent | 20.00 | 20.00 | 20.00 | 20.00 |
| Ethanol | 50.00 | 50.00 | 50.00 | 50.00 |
| Ethyl Acetate | 50.00 | 50.00 | 50.00 | 50.00 |

TABLE 49

Example 19

| Component | Time Points | $R^2$ | Slope | k (min$^{-1}$) | Half-life (t½), min |
|---|---|---|---|---|---|
| NVP | 0.25-8 min | 0.748 | −0.0336 | 0.0774 | 8.96 |
| HEMA | 0.25-6 min | 0.999 | −0.1519 | 0.3498 | 1.98 |
| TEGDMA | 0.25-8 min | 0.988 | −0.1942 | 0.4472 | 1.55 |
| CGI 819 | 0.25-1 min | 0.997 | −0.3746 | 0.8627 | 0.80 |
| TRIS | 0.25-1 min | 0.979 | −0.0714 | 0.1644 | 4.21 |
| mPDMS 1000 | 0.25-4 min | 0.998 | −0.0769 | 0.1771 | 3.91 |

TABLE 50

Example 20

| Component | Time Points | $R^2$ | Slope | k (min$^{-1}$) | Half-life (t½), min |
|---|---|---|---|---|---|
| NVP | Calculated Based on Measured % Residuals | | | *0.1298 | 5.34 |
| HEMA | 0.25-2 min | 0.996 | −0.2446 | 0.5633 | 1.23 |
| TEGDMA | 0.25-4 min | 0.998 | −0.4205 | 0.9684 | 0.72 |
| CGI 819 | 0.25-1 min | 0.999 | −0.3117 | 0.7179 | 0.97 |
| TRIS | 0.25-2 min | 0.995 | −0.1294 | 0.2980 | 2.33 |
| mPDMS 1000 | 0.25-2 min | 0.992 | −0.1327 | 0.3056 | 2.27 |

*k = 0.693/5.34

TABLE 51

Example 21

| Component | Time Points (hr) | $R^2$ | Slope | k (hr$^{-1}$) | Half-life (t½), hr |
|---|---|---|---|---|---|
| NVP | 0.25-4 | 0.759 | −0.0654 | 0.1506 | 4.60 |
| HEMA | 0.25-1.75 | 0.891 | −0.2137 | 0.4922 | 1.41 |
| TEGDMA | 0.25-1.75 | 0.926 | −0.3307 | 0.7616 | 0.91 |
| TRIS | 0.25-2 | 0.743 | −0.1607 | 0.3701 | 1.87 |
| mPDMS 1000 | 0.25-2 | 0.741 | −0.1716 | 0.3952 | 1.75 |

TABLE 52

Example 22

| Component | Time Points (hr) | $R^2$ | Slope | k (hr$^{-1}$) | Half-life (t½), hr |
|---|---|---|---|---|---|
| NVP | 0.25-1.25, 1.75-2.00, 3.00 | 0.867 | −0.0867 | 0.1997 | 3.47 |
| HEMA | 0.25-0.75 | 0.893 | −0.2668 | 0.6144 | 1.13 |
| TEGDMA | 0.25-0.75 | 0.908 | −0.4034 | 0.9290 | 0.75 |
| TRIS | 0.25-1.00 | 0.747 | −0.2225 | 0.5124 | 1.35 |
| mPDMS 1000 | 0.25-1.00 | 0.704 | −0.2319 | 0.5341 | 1.30 |

TABLE 53

| | Ex. # | | | |
|---|---|---|---|---|
| | 19 | 20 | 21 | 22 |
| NVP ½ life | 8.96 | 5.34 | 4.6 | 3.47 |
| TRIS ½ life | 4.21 | 2.33 | 1.87 | 1.35 |
| mPDMS ½ life | 3.91 | 2.27 | 1.75 | 1.3 |
| NVP/TRIS | 2.13 | 2.29 | 2.46 | 2.57 |
| NVP/mPDMS | 2.29 | 2.35 | 2.63 | 2.67 |
| [μmol NVP]/[μmol TRIS] @90% conversion | 37.8 | 41.2 | 61.6 | 58.9 |
| [μmol NVP]/[μmol mPDMS] @90% conversion mPDMS | 115.6 | 127.8 | 200.9 | 135.7 |

TABLE 54

| | % | % | | Mechanicals | | |
|---|---|---|---|---|---|---|
| Ex.# | $H_2O$ | Haze | DCA | Mod. (psi) | Elong. (%) | Dk |
| 19 | 56.7 (0.1) | 6 (0) | 41 (4) | 149.8 (9.9) | 107.9 (18.3) | 74.9 |
| 20 | 60.8 (0.1) | 9 (1) | 45 (6) | 102.2 (11.5) | 83.4 (18.0) | 77.2 |
| 21 | 51.9 (0.1) | 5 (1) | 44 (3) | 218.0 (4.3) | 111.2 (16.4) | 77.4 |
| 22 | 53.4 (0.1) | 6 (1) | 34 (6) | 216.5 (12.5) | 125.0 (19.7) | 59 |

Examples 19 and 20 used visible light initiation, and Examples 21-22 used thermal initiation. All examples displayed desirable water content, haze and advancing contact angles. However, Examples 21 and 22 displayed undesirably high modulii (greater than 200 psi) and also undesirably long cure times 24 hours (compared with the cure times of the formulations of the present invention (less than 30 minutes).

FIGS. 4-7 show the importance of the kinetic half life ratios and the conversion ratios on the resulting advancing contact angle and Dk of the lenses.

Figure 4:
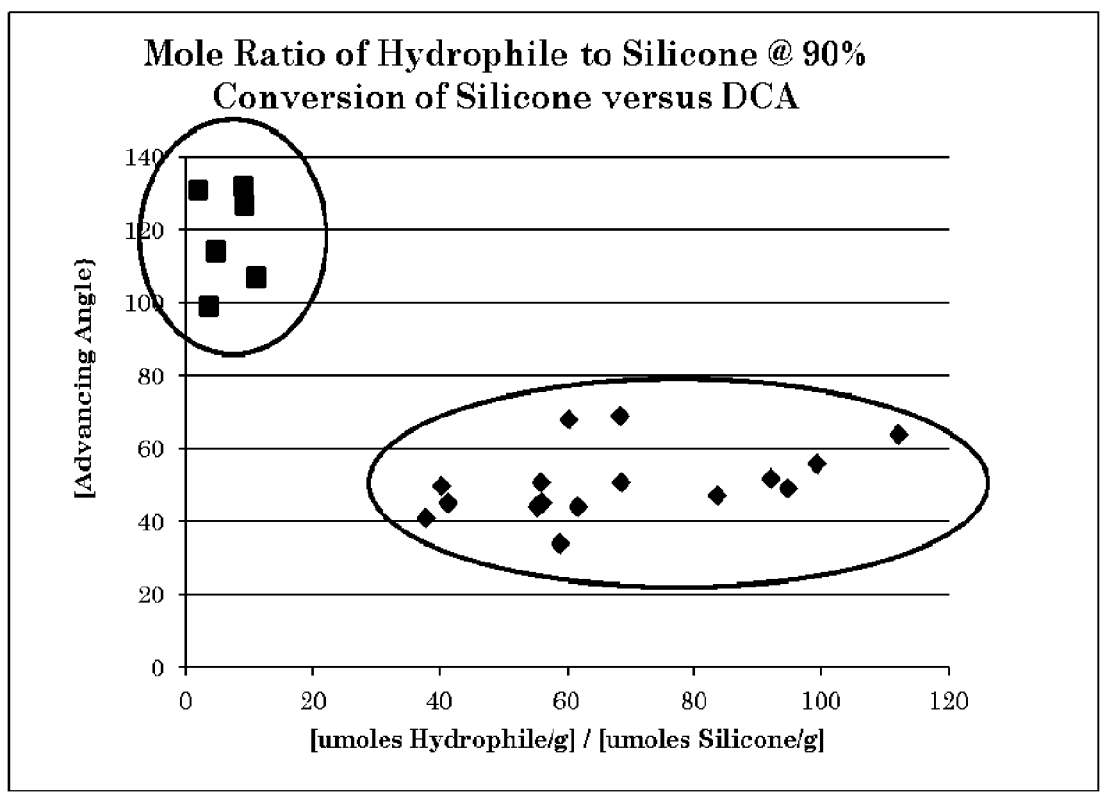
FIG. 4 is a graph of the conversion mole ratio vs. advancing contact angle of the contact lenses made in Examples 1, 3-13, 17, 19-23 and Comparative Examples 1, 3, 4 and 6-7.
Figure 5:
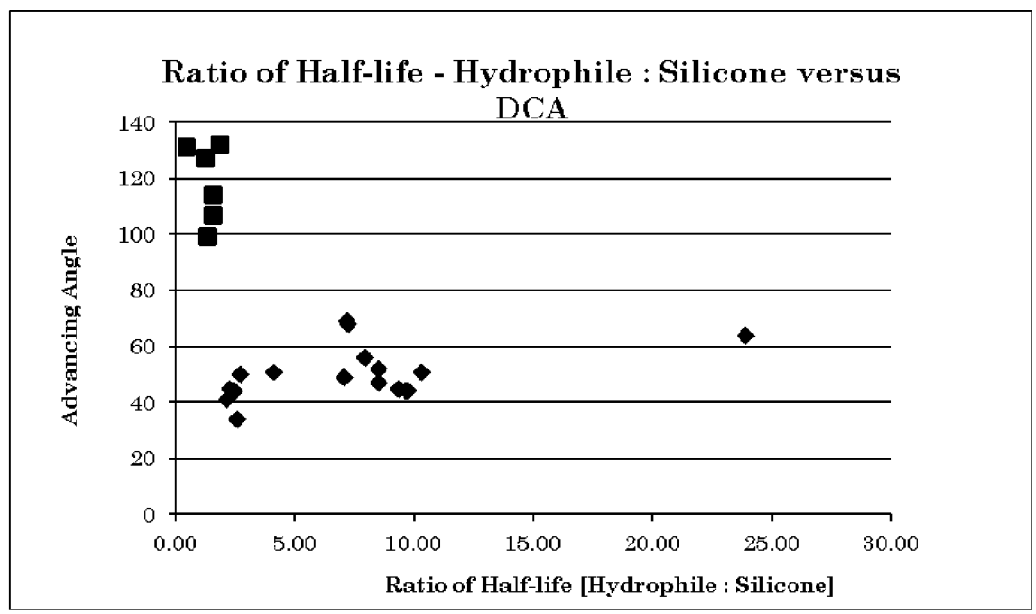
FIG. 5 is a graph of the half life ratio vs. advancing contact angle for the contact lenses made in Examples 1, 3-13, 17, 19-23 and Comparative Examples 1, 3, 4 and 6-7.
Figure 6:
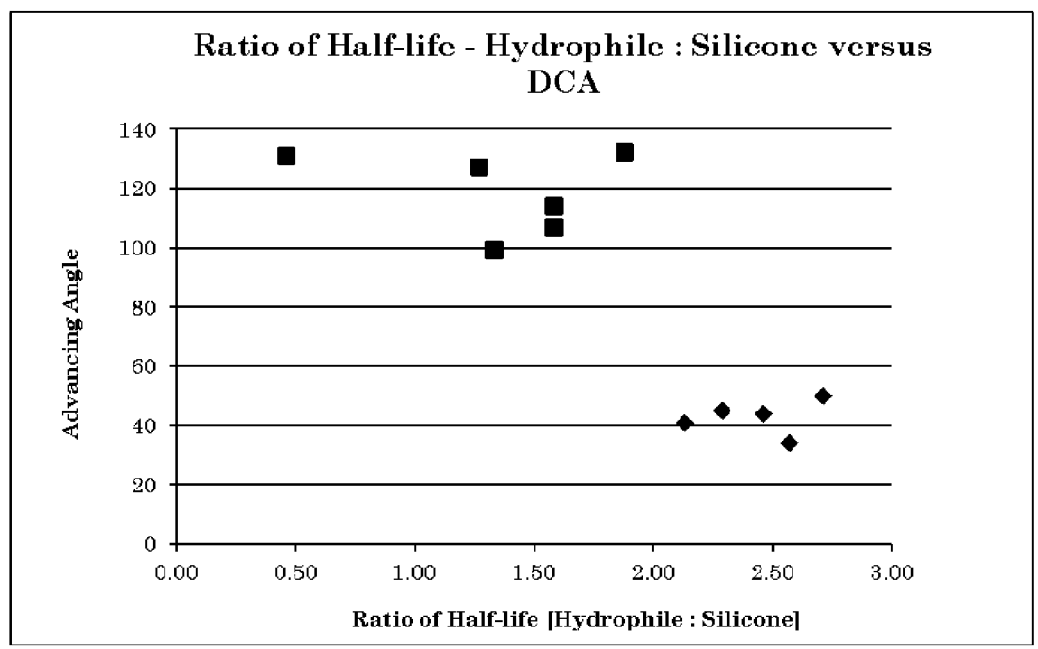
FIG. 6 is a graph of the half life ratio vs. advancing contact angle for the contact lenses, with the axis for the half life ratios expanded to show the area up to 3.
Figure 7:
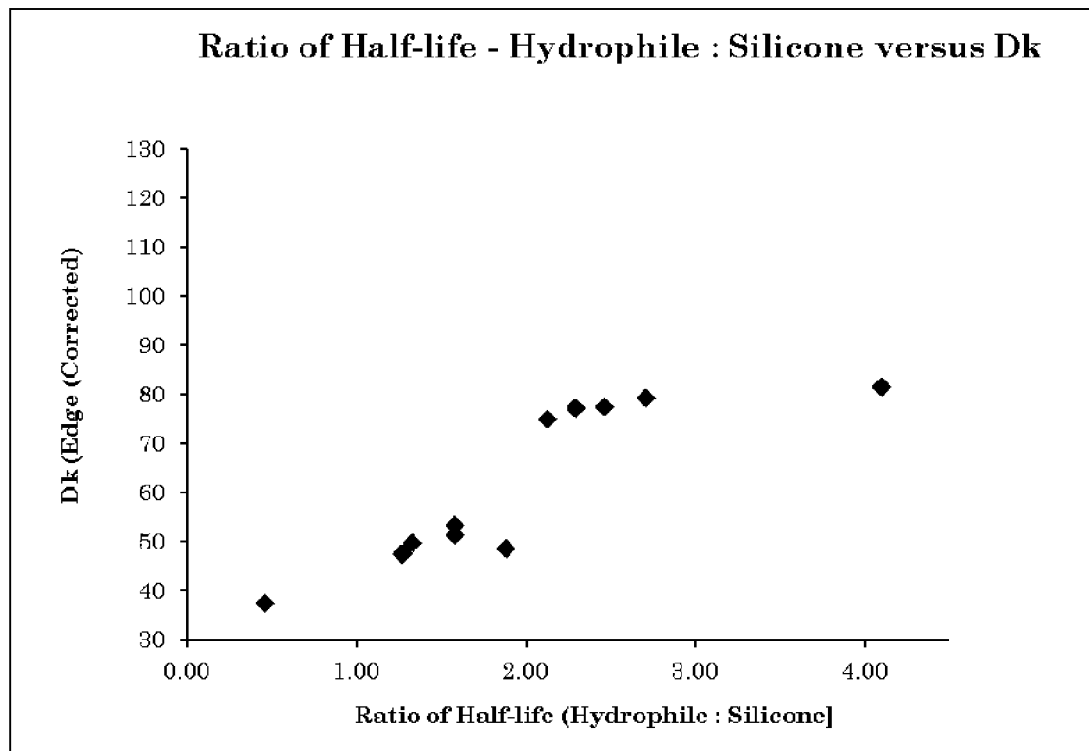
FIG. 7 is a graph of the half life ratio vs. Dk for the contact lenses with the axis for the half life ratios expanded to show the area up to 4.

FIG. 4 is a graph of the conversion mole ratio vs. advancing contact angle of the contact lenses made in Examples 1, 3-13, 17, 19-23 and Comparative Examples 1, 3, 4 and 6-7, and FIG. 5 is a graph of the half life ratio vs. advancing contact angle for the same contact lenses. FIG. 6 is a graph of the half life ratio vs. advancing contact angle, but with the axis for the half life ratios expanded to show the area up 3. Looking at FIGS. 4 and 6 it can be seen that conversion ratios of at least 20, and kinetic half-life ratios of at least about 2 surprisingly form lenses with exceptional wettability. FIG. 7 also shows that at a kinetic half life ratio of about 2 there is a surprising discontinuity in the Dk of the resulting lenses, with contact lenses formed from reaction mixtures where kinetic half life ratio of the slow-reacting hydrophilic monomer:silicone-containing was 2 or greater had a surprisingly increased Dk compared to formulations where the kinetic half life ratio of the slow-reacting hydrophilic monomer:silicone-containing was less than 2.

Example 23 and Comparative Examples 8-12

A reaction mixture was formed by mixing the components listed in Table 55 and degassed by applying vacuum at ambient temperature for about 7-10 minutes. The amounts of the reaction components are listed as the weight % of reaction components, without diluent. The reaction mixture (75 µL) was dosed, cured, and the lenses demolded, released, packaged and autoclaved using the process of Example 1, with a cure time of 20 minutes.

Lens properties are shown in Table 56.

TABLE 55

| Component | Ex. 23 | CE 8 | CE9 | CE10 | CE11 | CE12 |
|---|---|---|---|---|---|---|
| mPDMS 1000 | 16.50 | 16.50 | 16.50 | 16.50 | 16.50 | 16.50 |
| OH-mPDMS, n = 4 | 27.50 | 27.50 | 27.50 | 27.50 | 27.50 | 27.50 |
| NVP | 46.65 | 44.15 | 41.65 | 39.15 | 35.15 | 23.35 |
| HEMA | 6.75 | 6.75 | 6.75 | 6.75 | 6.75 | 6.75 |
| DMA | 0.00 | 2.50 | 5.00 | 7.50 | 11.50 | 23.30 |
| EGDMA | 0.35 | 0.35 | 0.35 | 0.35 | 0.35 | 0.35 |
| Norbloc | 1.75 | 1.75 | 1.75 | 1.75 | 1.75 | 1.75 |
| CGI 819 | 0.50 | 0.50 | 0.50 | 0.50 | 0.50 | 0.50 |
| Diluent | 10.00 | 10.00 | 10.00 | 10.00 | 10.00 | 10.00 |
| TAA | 100.00 | 100.00 | 100.00 | 100.00 | 100.00 | 100.00 |

TABLE 56

| Ex # | % $H_2O$ | % Haze | DCA | Mechanicals Mod. (psi) | Elong. (%) | Dk |
|---|---|---|---|---|---|---|
| Ex 23 | 61 (0) | 6 (1) | 48 (6) | 75 (10) | 145 (57) | 92 |
| CE8 | 63 (0) | 7 (1) | 79 (6) | 57 (6) | 171 (36) | 89 |
| CE9 | 63 (0) | 9 (1) | 107 (3) | 52 (4) | 164 (53) | 89 |
| CE10 | 63 (0) | 9 (1) | 110 (4) | 46 (6) | 162 (45) | 89 |
| CE11 | 60 (0) | 6 (1) | 119 (15) | 53 (6) | 184 (56) | 85 |
| CE12 | 56 (0) | 4 (0) | 114 (13) | 66 (6) | 195 (44) | 72 |

DMA is a hydrophilic component with intermediate reaction kinetics. It can be seen from the data in Table 56, that amounts of DMA as small as 2.5 wt % (Comparative Example 8), dramatically decrease the modulus, but increase the advancing contact angle of the resulting contact lenses. Depending upon the other properties of the lens, an advancing contact angle of about 80°, as shown by Comparative Example 8, may be acceptable. The Dk of the lenses also decreased as the amount of DMA increased, even though the amount of silicone containing components remained constant. The kinetics for Examples 23, and Comparative Examples 8 and 9 are shown in Tables 57-59, below. The kinetic data was collected and calculated as described above, except that all time points were measured in seconds.

TABLE 57

| Ex. 23 | | | | | | |
|---|---|---|---|---|---|---|
| Component | Time Points | $R^2$ | Slope | k ($s^{-1}$) | Half-life ($t^{1/2}$), s | Half-life ($t^{1/2}$), min |
| NVP | 5-600 s | 0.978 | −0.0007 | 0.00161 | 429.87 | 7.16 |
| HEMA | 5-120 s | 0.999 | −0.0068 | 0.01566 | 44.25 | 0.74 |
| EGDMA | 5-120 s | 0.994 | −0.0120 | 0.02764 | 25.08 | 0.42 |
| Norbloc | 5-120 s | 0.995 | −0.0071 | 0.01635 | 42.38 | 0.71 |
| CGI 819 | 5-240 s | 0.999 | −0.0076 | 0.01750 | 39.59 | 0.66 |
| OH-mPDMS | 5-120 s | 0.996 | −0.0060 | 0.01382 | 50.15 | 0.84 |
| mPDMS 1000 | 5-120 s | 0.994 | −0.0038 | 0.00875 | 79.19 | 1.32 |

TABLE 58

| CE 8 | | | | | | |
|---|---|---|---|---|---|---|
| Component | Time Points | $R^2$ | Slope | k ($s^{-1}$) | Half-life ($t^{1/2}$), s | Half-life ($t^{1/2}$), min |
| DMA | 5-60 s | 0.978 | −0.0032 | 0.00737 | 94.03 | 1.57 |
| NVP | 5-360 s | 0.992 | −0.0008 | 0.00184 | 376.14 | 6.27 |
| HEMA | 5-60 s | 0.986 | −0.0064 | 0.01474 | 47.02 | 0.78 |
| EGDMA | 5-60 s | 0.987 | −0.0126 | 0.02902 | 23.88 | 0.40 |
| Norbloc | 5-60 s | 0.996 | −0.0061 | 0.01405 | 49.33 | 0.82 |
| CGI 819 | 5-120 s | 0.995 | −0.0068 | 0.01566 | 44.25 | 0.74 |
| OH-mPDMS | 5-60 s | 0.995 | −0.0055 | 0.01267 | 54.71 | 0.91 |
| mPDMS 1000 | 5-60 s | 0.983 | −0.0034 | 0.00783 | 88.50 | 1.48 |

TABLE 59

| CE 9 | | | | | | |
|---|---|---|---|---|---|---|
| Component | Time Points | $R^2$ | Slope | k ($s^{-1}$) | Half-life ($t^{1/2}$), s | Half-life ($t^{1/2}$), min |
| DMA | 5-60 s | 0.984 | −0.0034 | 0.00783 | 88.50 | 1.48 |
| NVP | 5-360 s | 0.995 | −0.0009 | 0.00207 | 334.35 | 5.57 |
| HEMA | 5-120 s | 0.996 | −0.0070 | 0.01612 | 42.99 | 0.72 |
| EGDMA | 5-60 s | 0.988 | −0.0126 | 0.02902 | 23.88 | 0.40 |
| Norbloc | 5-60 s | 0.994 | −0.0061 | 0.01405 | 49.33 | 0.82 |
| CGI 819 | 5-120 s | 0.996 | −0.0072 | 0.01658 | 41.79 | 0.70 |
| OH-mPDMS | 5-60 s | 0.99/8 | −0.0054 | 0.01244 | 55.72 | 0.93 |
| mPDMS 1000 | 5-60 s | 0.982 | −0.0034 | 0.00783 | 88.50 | 1.48 |

Comparing the kinetic data from Tables 57-59, it can be seen that as DMA is added to the formulations in increasing amounts the kinetic half life of NVP decreases from 7.16 in Example 23 to 5.57 in Comparative Example 9. The ratio of the kinetic half life to the silicone monomer HO-PMDS also decreases.

Examples 24-26, and Comparative Example 13

Lenses were made using the formulations listed in Table 60,

Each reaction mixture was formed by mixing the components listed in Table 60 and degassed by applying vacuum at ambient temperature for about 25 minutes. The reaction mixture (75 µL) was then dosed at room temperature and <0.1% $O_2$, into thermoplastic contact lens molds (FC-Zeonor, BC Polypropylene) which had been degassed in $N_2$ box at RT (Compartment 1, FIG. 2) for a minimum of 12 hours prior to dosing. The BC was placed on the FC mold to produce 8 BC/FC assemblies in a pallet. Eight pallets were assembled and moved into the cure compartment (Compartment 2, FIG. 2). Pallets were placed on a mirrored surface and a quartz plate (0.50 mm thick) was placed over each pallet. The lenses were cured for 20 minutes, an intensity of 4-5 mW/cm$^2$, <0.1% $O_2$, and 62-65° C.

The molds were mechanically separated demolded (lenses remained in FC). The lenses were dry released by pressing on the back of the front curve. Lenses were extracted in DI water and equilibrated in borate buffered packing solution in lens vials and sterilized at 122° C. for 30 minutes.

The properties of the lenses were measured and are shown in Table 61, below.

TABLE 60

| Component | Ex 24 | Ex 25 | Ex. 26 | CE 13 |
|---|---|---|---|---|
| mPDMS 1000 | 16.50 | 16.50 | 16.50 | 16.50 |
| OH-mPDMS, n = 4 | 27.50 | 27.50 | 27.50 | 27.50 |
| NVP | 46.55 | 46.05 | 45.55 | 44.05 |
| HEMA | 6.75 | 6.75 | 6.75 | 6.75 |
| DMA | 0.00 | 0.50 | 1.00 | 2.50 |
| EGDMA | 0.45 | 0.45 | 0.35 | 0.45 |
| Norbloc | 1.75 | 1.75 | 1.75 | 1.75 |
| CGI 819 | 0.50 | 0.50 | 0.50 | 0.50 |

TABLE 61

| Lens | % H$_2$O | % Haze | DCA | Mod. (psi) | Elong. (%) | Dk |
|---|---|---|---|---|---|---|
| Ex 24 | 54 (0) | 9 (0) | 50 (4) | 111 (12) | 148 (39) | 98 |
| Ex 25 | 54 (0) | 11 (1) | 58 (9) | 117 (8) | 167 (36) | 97 |
| Ex 26 | 55 (0) | 10 (1) | 64 (4) | 122 (9) | 170 (27) | 97 |
| CE 13 | 54 (0) | 10 (0) | 93 (11) | 100 (7) | 146 (31) | 100 |

Examples 24-26 show that small amounts of non-hydroxyl containing hydrophilic monomers, which are not slow reacting hydrophilic monomers may be incorporated into the formulations of the present invention without losing wettablity. Also, comparing Comparative Example 13, with Comparative Example 8 (both had 2.5 wt % DMA), it can be seen that where a formulation cured without diluents displays undesirable properties (Comparative Example 13, DCA of 93°), including a small amount of diluent may reduce the advancing contact angle (Comparative Example 8, DCA of 79° and 10% t-amyl alcohol as a diluent).

Residual NVP in the reaction mixture was analyzed as function of cure time With the degassed reaction mixtures in Examples 24-26 and CE13, cure studies were conducted as follows. For each reaction mixture (75 μL) was dosed at room temperature and <0.1% O$_2$, into thermoplastic contact lens molds (2 pallets containing 8 assemblies each, FC-Zeonor, BC Polypropylene) which had been degassed in N$_2$ box at RT (Compartment 1, FIG. 2) for a minimum of 12 hours prior to dosing. The BC was placed on the FC mold and the 2 pallets were moved into Compartment 2 and placed a mirrored surface. A quartz plate (0.50 mm thick) was placed over each pallet and the assembly was cured for 5 minutes at an intensity of 4-5 mW/cm$^2$, <0.1% O$_2$, and 62-65° C.

The molds were mechanically separated and using metallic tweezers and spatula, about five lenses were removed from the molds and accurately weighed into a glass scintillation vial. Using a calibrated Eppendorf pipet, 5 mL methanol was added to the vial. Samples were prepared in duplicate.

The cure and sample preparation procedures were repeated to generate duplicate samples at the following cure times (minutes): 10, 15 and 20. Cured polymers were extracted in methanol overnight by gently shaking at room temperature. Analysis of NVP in the cured samples was accomplished by HPLC following the method described earlier.

The concentration of NVP in each sample, expressed as a percent of the sample weight as follows:

% NVP=[(μg/mL in Sample Extract*Volume of Extract*Dilution Factor*10$^{-6}$ g/μg)/(g Sample Weight)]*100

The results are shown in Table 62.

TABLE 62a

Residual NVP, Wt % of Cured Polymer (Stdev.)

| | DMA (Wt. %) | | | |
|---|---|---|---|---|
| Cure Time (mins) | 0.0% Ex. 24 | 0.5% Ex. 25 | 1.0% Ex. 26 | 2.5% CE 13 |
| 5 | 14.58 (1.71) | 11.12 (0.72) | 13.41 (0.20) | 8.14 (0.05) |
| 10 | 1.92 (0.02) | 1.91 (0.07) | 2.07 (0.09) | 1.71 (0.06) |
| 15 | 1.12 (0.01) | 1.12 (0.02) | 1.13 (0.01) | 0.97 (0.01) |
| 20 | 0.80 (0.01) | 0.77 (0.00) | 0.82 (0.02) | 0.70 (0.00) |

TABLE 62b

Residual NVP, Expressed as % of Initial NVP in Reactive Mixture

| | DMA (Wt. %) | | | |
|---|---|---|---|---|
| Cure Time (mins) | 0.0% Ex. 24 | 0.5% Ex. 25 | 1.0% Ex. 26 | 2.5% CE 13 |
| 5 | 31.32 | 24.15 | 29.44 | 18.48 |
| 10 | 4.12 | 4.15 | 4.54 | 3.88 |
| 15 | 2.41 | 2.43 | 2.57 | 2.20 |
| 20 | 1.72 | 1.67 | 1.80 | 1.59 |

From the data in Tables 62a and b, it can be seen that as the concentration of DMA increases, the amount of NVP incorporated into the lenses across all the times measured increases. The difference is particularly noticeable at 5 minutes, which indicates that more NVP is polymerizing with the silicone monomers when DMA is included in amounts of 2.5 wt % or more.

Examples 27-33

A series of lens formulations were formed from the following reactive components:
38.5 wt % mPDMS
NVP
hydroxyalkyl methacrylate, shown in Table 63
1 wt % TEGDMA
0.25 CGI 819

The amount of hydroxylalkyl(meth)acrylate and NVP were varied to provide molar ratios of the hydroxylalkyl (meth)acrylate:NVP of about 0.2. GMMA has two hydroxyl groups. Accordingly, formulations having two different concentrations of GMMA were prepared, Example 32 (13.23 wt % GMMA, 0.408 ratio, counting both hydroxyls) and Example 33 (6.62 wt % GMMA, 0.204, counting two hydroxyl).

The reactive components were mixed with a diluent (50% TAA/50% DA) in a ratio of 80 wt % reactive components: 20 wt % diluent. Examples 31 and 32 produce hazy reaction mixtures which were not cured into lenses. Examples 27-30 and 33 produced clear reaction mixtures which were cast into lenses using the following procedure. The reaction mixture was degassed by applying vacuum at ambient temperature for about 17(±3) minutes. The reaction mixture was then dosed into thermoplastic contact lens molds (front curves made from Zeonor, and back curves from polypropylene), The BC was placed on the FC mold to produce 8 BC/FC assemblies in a pallet. Pallets were placed on a mirrored surface and a quartz plate (12.50 mm×6.25 mm×0.50 mm) was placed over each pallet. The lenses were cured for about 15 minutes at 45° C., under a nitrogen atmosphere, using Philips TL 20 W/03T fluorescent bulbs and 4-5 mW/cm$^2$.

Lenses were released in 50/50 IPA/water, extracted in 70/30 IPA/water and subsequently equilibrated in de-ionized water. Lenses were transferred into vials containing borate buffered saline for at least 24 hours and then autoclaved at 122° C. for 30 minutes. Lens properties were measured and are reported in Table 63, below.

TABLE 63

| Example | 27 | 28 | 29 | 30 | 31 | 32 | 33 |
|---|---|---|---|---|---|---|---|
| Component | HEMA | HPMA | HBMA | DMHEMA | HEAA | GMMA | GMMA |
| [NVP] wt % | 47.5 | 47.5 | 45.18 | 45.18 | 48.75 | 45.01 | 51.63 |
| [HOMA] wt % | 10.75 | 10.75 | 13.07 | 13.07 | 9.50 | 13.23 | 6.62 |
| HOMA:NVP (molar) | 0.193 | 0.174 | 0.203 | 0.203 | 0.188 | 0.408 | 0.204 |
| HO:Si | 0.19 | 0.19 | 0.19 | 0.19 | 0.19 | 0.38 | 0.19 |
| % H$_2$O | 59.1 (0) | 58.9 (0.1) | 54.5 | 60.4 | NT* | NT | 62.6 |
| % Haze | 8 (0) | 16 (0) | 8 | 15 | NT* | NT* | 12 |
| DCA | 60 (7) | 63 (5) | 46 | 70 | NT* | NT* | 49 |
| MOD (psi) | 79.9 (1.9) | 73.4 (1.4) | 120.5 | 68.7 | NT* | NT* | 70.4 |
| Elong (%) | 196.2 (24.6) | 230.1 (1.8) | 179.3 | 206.5 | NT* | NT* | 203.5 |
| Dk | 89.1 | 93.4 | 93.4 | 90 | NT* | NT* | 85.3 |

NT* = Not Tested

Comparing Examples 32 and 33, it can be seen that when the molar amount of GMMA was adjusted to account for both hydroxyls, clear lenses were formed. It is believed that Example 20, which included HEAA as the hydroxyalkyl(meth)acrylate, did not provide wettable lenses because the HEAA contains two polar groups, the amide and hydroxyl groups, making the HEAA more polar than the other hydroxylalkyl(meth)acrylates used in Examples 27-30 and 32-33. It is believed that the increased polarity of HEAA caused compatibility issues with the mPDMS. However, HEAA has the potential to work with more polar silicones, such as SiMAA, OH-mPDMS, N-(2,3-dihydroxypropane)-N'-(propyl tetra(dimethylsiloxy)dimethylbutylsilane)acrylamide. Thus, a variety of hydroxylalkyl(meth)acrylate compounds can be used to form the hydrogels of the present invention.

Examples 34-41

Additional reaction mixtures were made varying the diluents system used and the siloxane components as shown in Tables 64 and 65, below. All mixtures were formed using 80 wt % reactive components and 20 wt % diluents. The lenses were molded, cured, processed and sterilized according to the procedure described in Example 27, above. The lens properties were measured and are shown in Tables 64 and 65.

TABLE 64

|  | Ex 34 | Ex 35 | Ex 36 | Ex 37 |
|---|---|---|---|---|
| mPDMS | 20 | 20 | 20 | 20 |
| TRIS | 18.5 | 18.5 | 18.5 | 18.5 |
| NVP | 47.5 | 47.5 | 47.5 | 47.5 |
| HEMA | 10.75 | 10.75 | 10.75 | 10.75 |
| TEGDMA | 1 | 1 | 1 | 1 |
| Norbloc | 2 | 2 | 2 | 2 |
| CGI819 | 0.25 | 0.25 | 0.25 | 0.25 |
| Diluent | 1:1 EtOAc:EtOH | TAA | D3O | 1:1 TAA:DA |
| EWC | 46.0 ± 1.6% | 55.5 ± 0.1% | 58.9 ± 0.1% | 57.4 ± 0.1% |
| Haze | 50 ± 19 | 10 ± 2 | 12 ± 1 | 7 ± 0 |

TABLE 64-continued

|  | Ex 34 | Ex 35 | Ex 36 | Ex 37 |
|---|---|---|---|---|
| DCA | NT | NT | 66 ± 4° | 69 ± 6° |
| Modulus | 100 ± 13 psi | 83 ± 9 psi | 80 ± 7 psi | 88 ± 6 psi |
| Elongation | 305 ± 105% | 330 ± 49% | 307 ± 39% | 285 ± 73% |
| Dk | NT | 80 | 64 | 75 |

NT = Not tested

TABLE 65

|  | Ex 38** | Ex 39 | Ex 40** | Ex 41 |
|---|---|---|---|---|
| mPDMS | 38.5 | 38.5 | 38.5 | 38.5 |
| NVP | 47.5 | 47.5 | 47.5 | 47.5 |
| HEMA | 10.75 | 10.75 | 10.75 | 10.75 |
| TEGDMA | 1 | 1 | 1 | 1 |
| Norbloc | 2 | 2 | 2 | 2 |
| CGI819 | 0.25 | 0.25 | 0.25 | 0.25 |
| diluent | 1:1 EtOAc:EtOH | TAA | D3O | 1:1 TAA:DA |
| EWC | ** | 56.3 ± 0.2% | ** | 59 ± 0.1% |
| Haze | ** | 8 ± 0 | ** | 9 ± 1 |
| DCA | ** | 74 ± 2° | ** | 54 ± 3° |
| Modulus | ** | 62 ± 9 psi | ** | 70 ± 5 psi |
| % Elongation | ** | 252 ± 63% | ** | 245 ± 62% |
| Dk | ** | 107 | ** | 91 |

**Blends were immiscible

The blends of Examples 38 and 40 were immiscible and were not cast into lenses. These Examples show that a wide range of diluents may be used to form the lenses of the present invention. These examples also show that secondary alcohols provide formulations with a desirable balance of properties, including clarity and modulus, when photocured.

Examples 42-47

A reaction mixture was formed by mixing the components listed in Table 66 and degassed by applying vacuum at ambient temperature for about 17(±3) minutes. The amounts of the reaction components are listed as the weight % of reaction components, without diluent. The reaction mixture was mixed with the diluents listed in Table 67 to form the reaction mixtures. The reaction mixture (75 µL) was then dosed at room temperature and <0.1% O$_2$, into thermoplastic contact lens molds (FC-Zeonor, BC Polypropylene) which had been degassed in N$_2$ box at RT (Compartment 1, FIG. 2) for a minimum of 12 hours prior to dosing. The BC was placed on the FC mold to produce 8 BC/FC assemblies in a pallet. Eight pallets were prepared, moved into the cure compartment (Compartment 2) and placed on a mirrored surface. A quartz plate (12.50 mm×6.25 mm×0.50 mm) was placed over each pallet and the lenses were cured for 20 minutes, at an intensity of 4-5 mW/cm², <0.1% $O_2$, and 62-65° C.

The molds for all the lenses were mechanically separated demolded (lenses remained in FC). The lenses were dry released by pressing on the back of the front curve. Lenses were extracted in DI water All lenses were stored in borate buffered packing solution in lens vials and sterilized at 122° C. for 30 minutes. The properties of the lenses are shown in Table 68.

TABLE 66

| Base Formulation | |
|---|---|
| Component | % |
| mPDMS 1000 | 16.50 |
| OH-mPDMS, n = 4 | 27.50 |
| NVP | 46.55 |
| HEMA | 6.75 |
| EGDMA | 0.45 |

TABLE 66-continued

| Base Formulation | |
|---|---|
| Component | % |
| Norbloc | 1.75 |
| CGI 819 | 0.50 |

TABLE 67

| Ex# | 42 | 43 | 44 | 45 | 46 | 47 |
|---|---|---|---|---|---|---|
| Diluent @ 10% | NONE | 100% TAA | 50/50 TAA/BA | 50/50 TAA/BAGE | 70/30 TAA/BAGE | 50/50 TAA/PG |
| Level | 0.00 | 10.00 | 10.00 | 10.00 | 10.00 | 10.00 |
| TAM | N/A | 100.00 | 50.00 | 50.00 | 70.00 | 50.00 |
| BAGE | N/A | N/A | N/A | 50.00 | 30.00 | N/A |
| BA | N/A | N/A | 50.00 | N/A | N/A | N/A |
| PG | N/A | N/A | N/A | N/A | N/A | 50.00 |

TABLE 68

| Ex# | % $H_2O$ | % Haze | DCA | Mechanicals Mod. (psi) | Elong. (%) | Dk | Diameter (mm) | Residual NVP Wt % @ 20 min. |
|---|---|---|---|---|---|---|---|---|
| 42 | 53.7 (0.1) | 9 (1) | 40 (5) | 136 (16) | 142 (42) | 98 | 13.95 (0.11) | 1.76 (0.01) |
| 43 | 54.6 (0.3) | 8 (1) | 47 (4) | 127 (17) | 163 (36) | 93 | 13.62 (0.16) | 2.08 (0.12) |
| 44 | 60.0 (0.2) | 17 (0) | 82 (8) | 92 (13) | 138 (40) | 98 | 14.38 (0.03) | 0.44 (0.03) |
| 45 | 60.8 (0.2) | 17 (1) | 84 (4) | 78 (10) | 162 (34) | 95 | 14.53 (0.03) | 0.27 (0.00) |
| 46 | 60.4 (0.3) | 13 (2) | 79 (6) | 90 (11) | 134 (39) | 96 | 14.49 (0.03) | 0.27 (0.01) |
| 47 | 60.5 (0.2) | 2 (0) | 81 (6) | 87 (12) | 121 (40) | 97 | 14.41 (0.04) | 0.49 (0.04) |

Example 42 displayed very low haze (9%) and advancing contact angle) (40°, but a modulus of 136, which in some cases is higher than desired. In Examples 43 through 47 various diluent mixtures were evaluated to determine their impact on lens properties. In each of Example 43 through 47, 10% diluent was added, with different polyhydric alcohols as codiluents. As can be seen from Examples 44 through 47 the inclusion of a polyhydric alcohol decreased the modulus of the resulting lenses by up to about 40%. The lenses of Examples 42 and 43 displayed higher than desired deviations in lens diameter, due to their high levels of extractables at the end of cure. Examples 44-47 show that inclusion of a polyhydric component as a codiluent can reduce the level of extractables, and the variation in lens diameter.

Examples 47-52

A reaction mixture was formed by mixing the components listed in Table 69 and degassed by applying vacuum at ambient temperature for about 17(±3) minutes. The reaction mixture (75 μL) was then dosed at room temperature and <0.1% $O_2$, into thermoplastic contact lens molds (FC-Zeonor, BC Polypropylene) which had been degassed in $N_2$ box at RT (Compartment 1, FIG. 2) for a minimum of 12 hours prior to dosing. The BC was placed on the FC mold and the lenses were moved into Compartment 2 and cured for 20 minutes, at an intensity of 4-5 mW/cm², <0.1% $O_2$, and 62-65° C.

The molds for all the lenses were mechanically separated demolded (lenses remained in FC). The lenses were dry released by pressing on the back of the front curve. Lenses were extracted in DI water.

All lenses were stored in borate buffered packing solution in lens vials and sterilized at 122° C. for 30 minutes. The properties of the lenses are shown in Table 70.

TABLE 69

| | BAGE (Wt. %) | | | | | |
|---|---|---|---|---|---|---|
| Component | 0.0%<br>47 | 0.0%<br>48 | 0.5%<br>49 | 1.0%<br>50 | 1.5%<br>51 | 2.5%<br>52 |
| mPDMS 1000 | 16.50 | 16.50 | 16.50 | 16.50 | 16.50 | 16.50 |
| OH-mPDMS, n = 4 | 27.50 | 27.50 | 27.50 | 27.50 | 27.50 | 27.50 |
| NVP | 46.55 | 46.55 | 46.55 | 46.55 | 46.55 | 46.55 |
| HEMA | 6.75 | 6.75 | 6.75 | 6.75 | 6.75 | 6.75 |
| EGDMA | 0.45 | 0.45 | 0.45 | 0.45 | 0.45 | 0.45 |
| Norbloc | 1.75 | 1.75 | 1.75 | 1.75 | 1.75 | 1.75 |
| CGI 819 | 0.50 | 0.50 | 0.50 | 0.50 | 0.50 | 0.50 |
| Diluent | 0 | 5.00 | 5.00 | 5.00 | 5.00 | 5.00 |
| TAM | 0 | 100.00 | 90.00 | 80.00 | 70.00 | 50.00 |
| BAGE | 0 | 0.00 | 10.00 | 20.00 | 30.00 | 50.00 |

TABLE 70

| | | | | Mechanicals | | | |
|---|---|---|---|---|---|---|---|
| Ex# | % H$_2$O | % Haze | DCA | Mod.<br>(psi) | Elong.<br>(%) | Dk | Diameter<br>(mm) |
| 47 | 54 (0) | 7 (0) | 41 (7) | 133 (8) | 170 (31) | 95 | 14.09 (0.08) |
| 48 | 56 (0) | 8 (1) | 36 (13) | 130 (8) | 178 (33) | 93 | 13.96 (0.05) |
| 49 | 56 (0) | 10 (1) | 48 (4) | 115 (7) | 193 (28) | 101 | 14.04 (0.05) |
| 50 | 57 (0) | 18 (1) | 62 (8) | 110 (9) | 159 (22) | 98 | 14.27 (0.05) |
| 51 | 58 (0) | 18 (1) | 84 (6) | 107 (8) | 157 (31) | 94 | 14.55 (0.02) |
| 52 | 59 (0) | 15 (1) | 83 (6) | 99 (7) | 169 (39) | 93 | 14.60 (0.05) |

Example 47 contained no diluent and displayed desirably low haze and advancing contact angle. Examples 48 through 52 comprised 5 wt % diluent, with Examples 49 through 52 containing between 0.5 and 2.5 wt % BAGE as a codiluent. Examples 49 and 50 displayed desirable advancing contact angles and reduced modulus compared with both the no diluent formulation of Example 47 and Example 48 which contained t-amyl alcohol as the only diluent.

Examples 53-59

The reaction components listed in Table 71 were combined with the diluents listed in Table 72. The resulting reaction mixtures were dispensed into lens molds, cured, and processed as described in Examples 42-47. The properties of the lenses were measured and are shown in Table 73, below.

TABLE 71

| Base Formulation | |
|---|---|
| Component | % |
| mPDMS 1000 | 16.50 |
| OH-mPDMS, n = 4 | 27.50 |
| NVP | 44.55 |
| HEMA | 8.75 |
| EGDMA | 0.45 |
| Norbloc | 1.75 |
| CGI 819 | 0.50 |

TABLE 72

| Diluent | 80 | 81 | 82 | 83 | 84 | 85 | 86 |
|---|---|---|---|---|---|---|---|
| TAA | None | 5.0% | 4.9% | 4.75% | 4.5% | 4.0% | 2.5% |
| PVP K90 | None | None | 0.1% | 0.25% | 0.5% | 1.0% | 2.5% |

TABLE 73

| | | | | Mechanicals | | | | |
|---|---|---|---|---|---|---|---|---|
| Lens | % H$_2$O | % Haze | DCA | Mod.<br>(psi) | Elong.<br>(%) | Dk | Dia.<br>(mm) | Residual NVP % |
| 80 | 54 (0) | 11 (1) | 71 (6) | 142 (8) | 164 (32) | 87 | 14.10 (0.05) | 0.69 90.04) |
| 81 | 55 (0) | 10 (1) | 48 (7) | 144 (7) | 153 (31) | 99 | 13.98 (0.03) | 0.13 (0.01) |
| 82 | 56 (0) | 11 (1) | 39 (8) | 140 (9) | 151 (43) | 93 | 14.00 (0.02) | 0.13 (0.00) |
| 83 | 56 (0) | 11 (0) | 64 (10) | 132 (10) | 181 (30) | 94 | 13.99 (0.04) | 0.13 (0.02) |
| 84 | 55 (0) | 11 (1) | 55 (4) | 115 (13) | 188 (36) | 97 | 14.02 (0.04) | 0.14 (0.01) |
| 85 | 55 (0) | 14 (1) | 54 (10) | 117 (12) | 105 (20) | 98 | 14.03 (0.05) | 0.17 (0.01) |
| 86 | 55 (0) | 36 (5) | 64 (7) | 122 (11) | 199 (34) | 90 | 14.13 (0.06) | 0.27 (0.1) |

Small amounts of PVP (0.1 to 2.5 w % based upon all components in the reaction mixtures) were added with the diluent. Amounts of PVP between about 0.5 and 2.5 wt % (Examples 57-59) reduced modulus without negatively impacting advancing contact angle. The decrease in modulus is surprising based upon the small amount of PVP added, and the fact that the PVP used (molecular weight, K90) is a viscous liquid. Generally increasing the viscosity of the reaction mixture tends to increase modulus.

Examples 87-102

The effect of crosslinker on lens properties was evaluated using the base formulation in Table 74, and the crosslinker type, amount and the concentration of NVP shown in Table 75, with concentration of the reactive components, excluding the diluent, adding up to 100 wt %.

TABLE 74

Base Formulation

| Component | % |
|---|---|
| mPDMS 1000 | 19 |
| OH-mPDMS, n = 4 | 27.50 |
| NVP | 44.55 |
| HEMA | 6.75 |
| Norbloc | 1.75 |
| CGI 819 | 0.50 |
| TAA | 5 |

TABLE 75

| Ex. # | [NVP] | [EGDMA] | [AMA] | [HEMA-Vc] |
|---|---|---|---|---|
| 87 | 44.25 | 0.25 | 0 | 0 |
| 88 | 44 | 0.5 | 0 | 0 |
| 89 | 43.5 | 1 | 0 | 0 |
| 90 | 43 | 1.5 | 0 | 0 |
| 91 | 44.34 | 0 | 0.16 | 0 |
| 92 | 44.18 | 0 | 0.32 | 0 |
| 93 | 43.87 | 0 | 0.63 | 0 |
| 94 | 43.56 | 0 | 0.94 | 0 |
| 95 | 44.25 | 0 | 0 | 0.25 |
| 96 | 44 | 0 | 0 | 0.5 |
| 97 | 43.5 | 0 | 0 | 1 |
| 98 | 43 | 0 | 0 | 1.5 |
| 99 | 44.05 | 0.45 | 0 | 0 |
| 100 | 43.05 | 0.45 | 0 | 1 |
| 101 | 42.05 | 0.45 | 0 | 2 |
| 102 | 41.05 | 0.45 | 0 | 3 |

The reaction mixtures were degassed by applying vacuum at ambient temperature for about 17(±3) minutes. The reaction mixture (75 µL) was then dosed at room temperature and <0.1% $O_2$, into thermoplastic contact lens molds (FC-Zeonor, BC Polypropylene) which had been degassed in $N_2$ box at RT (Compartment 1, FIG. 2) for a minimum of 12 hours prior to dosing. The BC was placed on the FC mold and the lenses were moved into Compartment 2 and cured for 20 minutes, at an intensity of 4-5 mW/cm², <0.1% $O_2$, and 62-65° C.

The molds for all the lenses were mechanically separated and the lenses remained in the FC. The lenses were dry released by pressing on the back of the front curve. Lenses were extracted in DI water All lenses were stored in borate buffered packing solution in lens vials and sterilized at 122° C. for 30 minutes.

The ability of the lenses to recover from mechanical stress, such as folding was evaluated. A crease was generated in each lens by placing a folded unsterilized lens between two rectangular glass plates (12.5 cm×6.3 cm×0.5 cm (~113 g)) for five minutes. The lens was subsequently sterilized and visually inspected using a DL2 (17.5x) and Optimec, to discern the level of recovery.

Increasing degrees of creasing/stress were created in unsterilized lenses by using 2, 3, 4 or 5 top plates. The results of the stress test are shown in Tables 76-79.

The stress test values for three commercial lenses, ACUVUE OASYS with HYDRACLEAR Plus, Biofinity and Clariti lenses are shown as controls.

The properties of the lenses were measured and are shown in Table 80.

TABLE 76

Post Sterilization Inspection - DL2 (17.5X) and Optimec

| Ex# | Control (0 Plate) | 1 Plate | 2 Plates | 3 Plates | 4 Plates | 5 Plates |
|---|---|---|---|---|---|---|
| 87 | G | DL | DL | DL | DL | DL |
| 88 | G | DL | DL | DL | DL | DL |
| 89 | G | DL | DL | DL | DL | DL |
| 90 | G | DL | DL | DL | DL | DL |
| Oasys | G | G | G | G | G | G |
| Clariti | G | G | G | G | G | G |
| Biofinity | G | G | G | G | G | G |

G = Good (No Detectable Line)
DL = Definitive Line

TABLE 77

Post Sterilization Inspection - DL2 (17.5X) and Optimec

| Lens | Control (0 Plate) | 1 Plate | 2 Plates | 3 Plates | 4 Plates | 5 Plates |
|---|---|---|---|---|---|---|
| 91 | G | FL | FL | FL | FL | FL |
| 92 | G | VFL | VFL | VFL | VFL | VFL |
| 93 | G | G | G | G | G | G |
| 94 | G | G | G | G | G | G |

G = Good (No Detectable Line)
FL = Faint Line
VFL = Very Faint Line

TABLE 78

Post Sterilization Inspection - DL2 (17.5X) and Optimec

| Lens | Control (0 Plate) | 1 Plate | 2 Plates | 3 Plates | 4 Plates | 5 Plates |
|---|---|---|---|---|---|---|
| 95 | G | FL | FL | FL | FL | FL |
| 96 | G | FL | FL | FL | FL | FL |
| 97 | G | G | G | G | G | G |
| 98 | G | G | G | G | G | G |

G = Good (No Detectable Line)
FL = Faint Line

TABLE 79

Post Sterilization Inspection - DL2 (17.5X) and Optimec

| Lens | Control (0 Plate) | 1 Plate | 2 Plates | 3 Plates | 4 Plates | 5 Plates |
|---|---|---|---|---|---|---|
| 99 | G | DL | DL | DL | DL | DL |
| 100 | G | G | G | G | G | G |
| 101 | G | G | G | G | G | G |
| 102 | G | G | G | G | G | G |

TABLE 80

| | | | | Mechanicals | | |
|---|---|---|---|---|---|---|
| Lens | % $H_2O$ | % Haze | DCA | Mod. (psi) | Elong. (%) | Dk |
| 87 | 56 (0) | 17 (1) | 46 (6) | 104 (9) | 239 (52) | 99 |
| 88 | 52 (0) | 11 (2) | 46 (6) | 156 (8) | 174 (42) | 99 |
| 89 | 46 (0) | 8 (1) | 41 (12) | 326 (25) | 52 (19) | 101 |
| 90 | 42 (1) | 4 (0) | 44 (3) | 454 (51) | 45 (6) | 101 |
| 91 | 55 (0) | 13 (1) | 92 (3) | 98 (5) | 259 (955) | 104 |
| 92 | 52 (0) | 7 (1) | 8 (10) | 135 (8) | 203 (32) | 101 |
| 93 | 47 (0) | 4 (0) | 102 (7) | 194 (13) | 153 (27) | 105 |
| 94 | 42 (0) | 3 (0) | 100 (5) | 294 (29) | 93 (27) | 92 |

TABLE 80-continued

| Lens | % H₂O | % Haze | DCA | Mod. (psi) | Elong. (%) | Dk |
|---|---|---|---|---|---|---|
| 95 | 55 (0) | 12 (0) | 82 (7) | 97 (10) | 266 (61) | 95 |
| 96 | 51 (0) | 8 (1) | 91 (9) | 137 (6) | 208 (48) | 100 |
| 97 | 47 (1) | 5 (1) | 92 (8) | 211 (11) | 135 (27) | 103 |
| 98 | 44 (0) | 5(1) | 102 (6) | 284 (15) | 85 (25) | 99 |
| 99 | NT | NT | 35 (7) | 155 (15) | 165 (36) | NT |
| 100 | NT | NT | 80 (12) | 317 (38) | 53 (21) | NT |
| 101 | NT | NT | 102 (18) | 538 (48) | 33 (7) | NT |
| 102 | NT | NT | 109 (7) | 678 (74) | 33 (7) | NT |

Examples 103-108

Examples 87-90 were repeated using a mixture of EGDMA and TAC as shown in Table 81 below. The recovery of the lenses is shown in Table 82, and the properties of the lenses are shown in Table 83.

TABLE 81

| Component | 103 | 104 | 105 | 106 | 107 | 108 |
|---|---|---|---|---|---|---|
| NVP | 44.30 | 44.20 | 44.10 | 44.00 | 43.80 | 43.55 |
| EGDMA | 0.20 | 0.20 | 0.20 | 0.20 | 0.20 | 0.20 |
| TAC | 0.00 | 0.10 | 0.20 | 0.30 | 0.50 | 0.75 |

TABLE 82

Post Sterilization Inspection - DL2 (17.5X) and Optimec

| Lens | Control (0 Plate) | 1 Plate | 2 Plates | 3 Plates | 4 Plates | 5 Plates |
|---|---|---|---|---|---|---|
| 103 | G | DL | DL | DL | DL | DL |
| 104 | G | VFL | VFL | VFL | VFL | VFL |
| 105 | G | G | G | G | G | G |
| 106 | G | G | G | G | G | G |
| 107 | G | G | G | G | G | G |
| 108 | G | G | G | G | G | G |

TABLE 83

| Lens | % H₂O | % Haze | DCA | Mod. (psi) | Elong. (%) | Dk |
|---|---|---|---|---|---|---|
| 103 | 56 (0) | 16 (1) | 65 (4) | 93 (9) | 236 (72) | 99 |
| 104 | 55 (0) | 8 (0) | 62 (4) | 132 (6) | 217 (39) | 101 |
| 105 | 55 (0) | 5 (0) | 62 (2) | 124 (10) | 258 (43) | 94 |
| 106 | 53 (0) | 4 (1) | 70 (4) | 143 (16) | 169 (53) | 98 |
| 107 | 51 (0) | 3 (0) | 80 (7) | 154 (13) | 133 (45) | 94 |
| 108 | 48 (0) | 3 (0) | 97 (4) | 170 (17) | 180 (34) | 88 |

Examples 109-114

Lenses were made using the formulations shown in Table 84 and the process described in Examples 87-102. Lens properties were measured and are shown in Table 85.

TABLE 84

| | Ex.# | | | | | |
|---|---|---|---|---|---|---|
| | 109 | 110 | 112 | 112 | 113 | 114 |
| mPDMS 1000 | 19.35 | 19.35 | 19.35 | 19.35 | 19.35 | 19.35 |
| OH-mPDMS (n = 4) | 27.50 | 27.50 | 27.50 | 27.50 | 27.50 | 27.50 |
| VMA | 0.00 | 8.00 | 12.00 | 22.00 | 32.00 | 44.00 |
| HEMA | 6.50 | 6.50 | 6.50 | 6.50 | 6.50 | 6.50 |
| NVP | 44.00 | 36.00 | 32.00 | 22.00 | 12.00 | 0.00 |
| TEGDMA | 0.20 | 0.20 | 0.20 | 0.20 | 0.20 | 0.20 |
| TAC | 0.20 | 0.20 | 0.20 | 0.20 | 0.20 | 0.20 |
| Norbloc | 1.75 | 1.75 | 1.75 | 1.75 | 1.75 | 1.75 |
| CGI 819 | 0.50 | 0.50 | 0.50 | 0.50 | 0.50 | 0.50 |
| Diluent | 0.00 | 0.00 | 0.00 | 0.00 | 0.00 | 0.00 |
| TAM | N/A | N/A | N/A | N/A | N/A | N/A |

TABLE 85

| Lens | % H₂O | % Haze | DCA | Mod. (psi) | Elong. (%) | Dk | Res. NVP | Res. VMA |
|---|---|---|---|---|---|---|---|---|
| 109 | 55 (0) | 6 (0) | 55 (3) | 95 (6) | 270 (34) | 96 | 0.8 (0.02) | N/A |
| 110 | 56 (0) | 6 (0) | 67 (5) | 104 (7) | 233 (49) | 100 | NT | NT |
| 111 | 56 (0) | 5 (0) | 58 (4) | 100 (8) | 258 (36) | 100 | 0.51 (0.02) | 1.15 (0.08) |
| 112 | 58 (0) | 6 (0) | 56 (9) | 91 (9) | 223 (54) | 96 | 0.4 (0.04) | 2.2 (0.2) |
| 113 | 58 (0) | 7 (0) | 56 (5) | 92 (10) | 260 (62) | 103 | 0.3 (0.01) | 2.98 (0.06) |
| 114 | 58 (0) | 13 (2) | 50 (10) | 86 (7) | 262 (54) | 106 | N/A | 4.52 (0.61) |

TABLE 86

| Ex# | Control (0 Plate) | 1 Plate | 2 Plates | 3 Plates | 4 Plates | 5 Plates |
|---|---|---|---|---|---|---|
| 109 | G | G | G | G | G | G |
| 110 | G | G | G | G | G | G |
| 111 | G | G | G | G | G | G |
| 112 | G | G | G | G | G | G |
| 113 | G | G | G | G | G | G |
| 114 | G | G | G | G | G | G |

Post Sterilization Inspection - DL2 (17.5X) and Optimec

Examples 115-117

A reaction mixture was formed by mixing the components listed in Table 87 with 20 wt % of a 50:50 mixture of TAA and decanoic acid and degassed by applying vacuum at ambient temperature for about 17(±3) minutes. The reaction mixture (75 μL) was then dosed at room temperature and <0.1% $O_2$, into thermoplastic contact lens molds (FC-Zeonor, BC Polypropylene) which had been degassed in $N_2$ box at RT (Compartment 1, FIG. 2) for a minimum of 12 hours prior to dosing. The BC was placed on the FC mold and the lenses were moved into Compartment 2 and cured for 20 minutes, at an intensity of 4-5 mW/cm², <0.1% $O_2$, and 62-65° C.

Lenses were released in 50/50 IPA/water, extracted in 70/30 IPA/water and subsequently equilibrated in de-ionized water. Lenses were transferred into vials containing borate buffered saline for at least 24 hours and then autoclaved at 122° C. for 30 minutes. Lens properties were measured and are reported in Table 88, below.

TABLE 67

| Component | 115 | 116 | 117 |
|---|---|---|---|
| mPDMS 1000 | 20.50 | 20.50 | 20.50 |
| NVP | 65.50 | 70.50 | 72.50 |
| DMA | 0.00 | 0.00 | 0.00 |
| HEMA | 10.75 | 5.75 | 3.25 |
| TEGDMA | 1.00 | 1.00 | 1.50 |
| Norblock | 2.00 | 2.00 | 2.00 |
| CGI 819 | 0.25 | 0.25 | 0.25 |

TABLE 68

| Ex.# Lens | % $H_2O$ | % Haze | DCA | Mod. (psi) | Elong. (%) | Dk | HO:Si (mol) |
|---|---|---|---|---|---|---|---|
| 115 | 70.5 (0.2) | 4 (1) | 55 (6) | 51.0 (6.3) | 208.7 (37.5) | 48.9 | 0.36 |
| 116 | 78.1 (0.1) | 6 (0) | 50 (6) | 30.8 (2.6) | 224.9 (29.6) | 58.1 | 0.19 |
| 117 | 77.9 (0.3) | 30 (1) | 51 (7) | 29.7 (2.2) | 172.0 (36.0) | 61.0 | 0.11 |

Example 118

Preparation of 2-hydroxybutyl methacrylate (HBMA)

A blend of 72 grams 1,2-epoxybutane (Aldrich), 0.85 g 4-methoxyphenol (Aldrich), and 6.5 g potassium hydroxide was stirred in a 500 ml round bottomed flask equipped with an addition funnel and thermocouple thermometer. 172 g methacrylic acid was added via the addition funnel, and the blend was slowly to 75° C., and stirred overnight under an air, then increased to 88° C. for 4 hours. The mixture was cooled, and 700 ml of 2.0 N NaOH was added to the mixture in a separatory funnel. The upper layer was washed with borate buffered saline three times. Ethyl ether (200 ml) was added to the combined saline washes to extract any product. The combined organic layers were dried over $NaSO_4$. The $NaSO_4$ was filtered out and the product was distilled (90-98° C./~4 mm Hg). 17.5 g product was collected, to which was added 4 mg 4-methoxyphenol. ¹H NMR: 6.1 ppm (1H, m), 5.5 (1H, m), 4.8 (0.25H m), 4.2 (0.64H, dd, 8.1 and 11.7 Hz), 4.0 (0.64 Hz, dd, 6.9 and 11.4 Hz), 3.6-3.8 1.26H, m), 2.3 (OH, br s), 1.9 (3H, m), 1.4-1.7 (2H, m), 0.9 (3H, m); consistent with a blend of 2-hydroxy-1-propylmethacrylate and 1-hydroxy-2-propylmethacrylate.

Example 119

Preparation of Dimethylhydroxyethylmethacrylate

The same procedure as for HBMA was used, but substituting 1,2-epoxy-2-methylpropane for the 1,2-epoxypropane. The product was isolated by distillation at 47-48°/0.4-0.6 mm Hg. ¹H NMR: 6.1 ppm (1H, s), 5.5 (1H, m), 4.0 (2H, s), 2.1 (OH, br s), 1.9 (3H, s), 1.2 (6H, m); consistent 2-hydroxy-2-methyl propylmethacrylate (dimethylhydroxyethylmethacrylate).

Example 120

Preparation of VINAL 4.82 g vinyl chloroformate was added to a mixture of 8.19 g β-alanine (Aldrich) in 74 ml acetonitrile. The resulting mixture was refluxed for 2 hours, then cooled to room temperature and allowed to sit for 2 hours. It was filtered and solvent was removed under reduced pressure. The crude product was dissolved in 30 ml distilled water and washed three times with ethyl acetate. The combined ethyl acetate washes were washed with 50 ml deionized water. Solvent was evaporated from the combined ethyl acetate washes to yield 4.5 g product as a fluffy yellowish solid. ¹H NMR: 7.1 ppm (dd, 1H), 5.4 ppm (br s, OH), 4.7 ppm (dd, 1H), 4.4 ppm (dd, 1H), 3.5 ppm (q, 2H), 2.6 ppm (t, 2H).

What is claimed is:

1. A silicone hydrogel formed from a reaction mixture comprising about 37 to about 75 wt % of at least one slow-reacting hydrophilic monomer having a slow-reacting hydrophilic monomer kinetic half life;
    at least one silicone-containing component having a silicone-containing component kinetic half life, which may be optionally substituted with at least one hydroxyl containing group;
    at least one photoinitiator; and
    at least one hydroxyl-containing component selected from said silicone-containing components substituted with at least one hydroxyl group, at least one hydroxyalkyl monomer, and mixtures thereof,
    wherein ratio of said slow-reacting hydrophilic component half life to said silicone-containing component half life is at least 2.

2. The silicone hydrogel of claim 1 wherein said kinetic half life ratio is at least about 3.

3. The silicone hydrogel of claim 1 wherein said kinetic half life ratio is at least about 5.

4. The silicone hydrogel of claim 1 further comprising a Dk of at least about 80.

5. The silicone hydrogel of claim 1 further comprising a Dk of at least about 85.

6. The silicone hydrogel of claim 1 further comprising a % haze of less than about 50%.

7. The silicone hydrogel of claim 1 further comprising a % haze of less than about 10%.

8. The silicone hydrogel of claim 1 further comprising a water content of at least about 55%.

9. The silicone hydrogel of claim 1 further comprising a water content of at least about 60%.

10. The silicone hydrogel of claim 1 further comprising a modulus of less than about 150 psi.

11. The silicone hydrogel of claim 1 further comprising a modulus of about 100 psi or less.

12. The silicone hydrogel of claim 1 wherein said reaction mixture further comprises at least one UV absorbing compound.

13. The silicone hydrogel of claim 12 wherein said at least one UV absorbing compound is selected from benzotriazoles.

14. The silicone hydrogel of claim 12 wherein said at least one UV absorbing compound is selected from the group consisting of reactive 2-(2'-hydroxyphenyl)benzotriazoles, 2-hydroxybenzophenones, 2-hydroxyphenyltriazines, oxanilides, cyanoacrylates, salicylates and 4-hydroxybenzoates.

15. The silicone hydrogel of claim 12 wherein said at least one UV absorbing compound is selected from the group consisting of 2-(2'-hydroxy-5-methacrylyloxyethylphenyl)-2H-benzotriazole, 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2,4-dihydroxyphenyl)-1,3-2H-dibenzotriazole, and mixtures thereof.

16. The silicone hydrogel of claim 12 comprising between about 0.5 and about 4 wt. %, of at least one UV absorber.

17. The silicone hydrogel of claim 12 comprising between about 1 wt % and about 2 wt % UV absorber.

18. The silicone hydrogel of claim 1 wherein said reaction mixture is substantially free of diluent.

19. The silicone hydrogel of claim 1 wherein said reaction mixture is substantially free of TRIS.

20. The silicone hydrogel of claim 1 wherein said reaction mixture is substantially free of silicone containing macromers or prepolymers.

21. The silicone hydrogel of claim 1 wherein said slow-reacting hydrophilic monomer comprises a reactive group selected from the group consisting of (meth)acrylamides, vinyls, allyls and combinations thereof and said silicone-containing component comprises a reactive group selected from the group consisting of (meth)acrylates, styryls, amides and mixtures thereof.

22. The silicone hydrogel of claim 1 wherein said slow-reacting hydrophilic monomer comprises a reactive group selected from the group consisting of vinyls, allyls and combinations thereof and said silicone-containing component comprises a reactive group selected from the group consisting of (meth)acrylates, styryls, amides and mixtures thereof.

23. The silicone hydrogel of claim 1 wherein said slow-reacting hydrophilic monomer is present in an amount between about 39 and about 70 wt %.

24. The silicone hydrogel of claim 1 wherein said slow-reacting hydrophilic monomer is present in an amount between about 39 and about 60 wt %.

25. The silicone hydrogel of claim 1 wherein said slow-reacting hydrophilic monomer comprises a reactive group selected from the group consisting of N-vinyl amides, O-vinyl carbamates, O-vinyl carbonates, N-vinyl carbamates, O-vinyl ethers, O-2-propenyl, wherein the vinyl or allyl groups may be further substituted with a methyl group.

26. The silicone hydrogel of claim 1 wherein said slow reacting hydrophilic monomer comprises at least one hydrophilic group selected from the group consisting of hydroxyls, amines, ethers, amides, ammonium groups, carboxylic acid, carbamates and combinations thereof.

27. The silicone hydrogel of claim 1 wherein said slow reacting hydrophilic monomer comprises at least one hydrophilic group selected from the group consisting of hydroxyls, ethers, amides, carboxylic acid combinations thereof.

28. The silicone hydrogel of claim 1 wherein said slow reacting hydrophilic monomer is selected from N-vinylamide monomer of Formula I, a vinyl pyrrolidone of Formula II-IV, n-vinyl piperidone of Formula V:

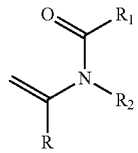

Formula I

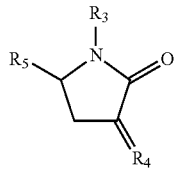

Formula II

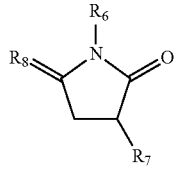

Formula III

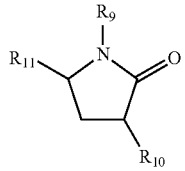

Formula IV

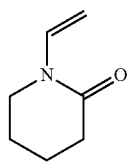

Formula V wherein R is H or methyl;

$R_1, R_2, R_3, R_6, R_7, R_{10}$, and $R_{11}$ are independently selected from H, $CH_3$, $CH_2CH_3$, $CH_2CH_2CH_3$, $C(CH_3)_2$;

$R_4$ and $R_5$ are independently selected from $CH_2$, $CHCH_3$ and $C(CH_3)$;

$R_5$ is selected from H, methyl, ethyl; and $R_9$ is selected from $CH=CH_2$, $CCH_3=CH_2$, and $CH=CHCH_3$.

29. The silicone hydrogel of claim 28 wherein the slow-reacting hydrophilic monomer is selected from the vinyl pyrrolidone of Formula II or IV or the N-vinyl amide monomer of Formula I, and the total number of carbon atoms in $R_1$ and $R_2$ is 4 or less.

30. The silicone hydrogel of claim 28 wherein the slow-reacting hydrophilic monomer is selected from a vinyl pyrrolidone of Formula III or IV and $R_6$ is methyl, $R_7$ is hydrogen, $R_9$ is $CH=CH_2$, $R_{10}$ and $R_{11}$ are H.

31. The silicone hydrogel of claim 1 wherein the slow-reacting hydrophilic monomer is selected from the slow-reacting hydrophilic monomer is selected from ethylene glycol vinyl ether (EGVE), di(ethylene glycol) vinyl ether (DEGVE), N-vinyl pyrrolidone (NVP), 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, N-vinyl-N-methyl acetamide (VMA), N-vinyl-N-ethyl acetamide, N-vinyl-N-ethyl formamide, N-vinyl formamide, N-vinyl acetamide, N-vinyl isopropylamide, allyl alcohol, N-vinyl caprolactam, N-2-hydroxyethyl vinyl carbamate, N-carboxy-β-alanine N-vinyl ester; N-carboxyvinyl-β-alanine (VINAL), N-carboxyvinyl-α-alanine and mixtures thereof.

32. The silicone hydrogel of claim 1 wherein the slow-reacting hydrophilic monomer is selected from NVP, VMA and 1-methyl-5-methylene-2-pyrrolidone.

33. The silicone hydrogel of claim 1 wherein the slow-reacting hydrophilic monomer comprises NVP.

34. The silicone hydrogel of claim 1 wherein said silicone-containing component comprises at least one hydroxyl group.

35. The silicone hydrogel of claim 1 further comprising at least one hydroxyalkyl monomer.

36. The silicone hydrogel of claim 35 wherein said hydroxyalkyl monomer is selected from hydroxyalkyl (meth)acrylate or (meth)acrylamide monomer of Formula VII or a styryl compound of Formula VIII

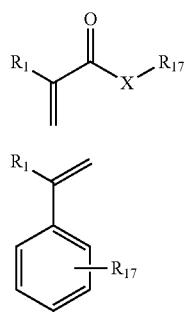

FORMULA VII

FORMULA VIII wherein $R_1$ is H or methyl,
X is O or $NR_{16}$, $R_{16}$ is a H, $C_1$ to $C_4$ alkyl, which may be further substituted with at least one OH, and
$R_{17}$ is selected from $C_2$-$C_4$ mono or dihydroxy substituted alkyl, and poly(ethylene glycol) having 1-10 repeating units.

37. The silicone hydrogel of claim 36 wherein $R_1$ is H or methyl, X is oxygen and R is selected from $C_2$-$C_4$ mono or dihydroxy substituted alkyl, and poly(ethylene glycol) having 1-10 repeating units.

38. The silicone hydrogel of claim 36 wherein $R_1$ methyl, X is oxygen and R is selected from $C_2$-$C_4$ mono or dihydroxy substituted alkyl, and poly(ethylene glycol) having 2-20 repeating units.

39. The silicone hydrogel of claim 36 wherein said hydroxyalkyl monomer is selected from 2-hydroxyethyl methacrylate, 2-hydroxyethyl acrylate, 3-hydroxypropyl (meth)acrylate, 2-hydroxypropyl (meth)acrylate, 1-hydroxypropyl-2-(meth)acrylate, 2-hydroxy-2-methyl-propyl (meth)acrylate, 3-hydroxy-2,2-dimethyl-propyl (meth)acrylate, 4-hydroxybutyl (meth)acrylate, glycerol (meth)acrylate, 2-hydroxyethyl(meth)acrylamide, polyethyleneglycol monomethacrylate, bis-(2-hydroxyethyl) (meth)acrylamide, 2,3-dihydroxypropyl (meth)acrylamide, and mixtures thereof.

40. The silicone hydrogel of claim 36 wherein said hydroxyalkyl monomer is selected from the group consisting of 2-hydroxyethyl methacrylate, glycerol methacrylate, 2-hydroxypropyl methacrylate, hydroxybutyl methacrylate, 3-hydroxy-2,2-dimethyl-propyl methacrylate, and mixtures thereof.

41. The silicone hydrogel of claim 36 wherein said hydroxyalkyl monomer comprises 2-hydroxyethyl methacrylate, 3-hydroxy-2,2-dimethyl-propyl methacrylate, glycerol methacrylate and mixtures comprising them.

42. The silicone hydrogel of claim 1 wherein the at least one silicone-containing component is monofunctional and comprises (a) a reactive group selected from (meth)acrylates, styryls, amides and mixtures thereof and (b) a polydialkyl siloxane chain and may optionally contain fluorine.

43. The silicone hydrogel of claim 1 wherein said silicone-containing component is selected from mono (meth)acryloxyalkyl polydialkylsiloxane monomer of Formula IX or the styryl polydialkylsiloxane monomer of Formula X:

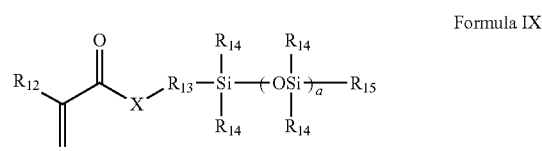

Formula IX

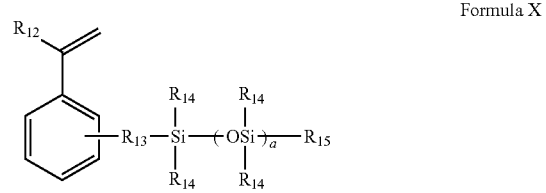

Formula X wherein $R_{12}$ is H or methyl;
X is O or $NR_{16}$,
each $R_{14}$ is independently a $C_1$ to $C_4$ alkyl which may be fluorine substituted, or phenyl;
$R_{15}$ is a $C_1$ to $C_4$ alkyl;
$R_{13}$ is a divalent alkyl group, which may further be functionalized with a group selected from the group consisting of ether groups, hydroxyl groups, carbamate groups and combinations thereof;
a is 3 to 50;
$R_{16}$ is selected from H, C1-4, which may be further substituted with one or more hydroxyl groups.

44. The silicone hydrogel of claim 43 wherein each $R_{14}$ is independently selected from ethyl and methyl groups.

45. The silicone hydrogel of claim 43 wherein all $R_{14}$ are methyl.

46. The silicone hydrogel of claim 43 wherein $R_{12}$ and each $R_{14}$ are methyl.

47. The silicone hydrogel of claim 43 wherein at least one $R_{14}$ is 3,3,3-trifluoropropyl.

48. The silicone hydrogel of claim 43 wherein $R_{13}$ is selected from C1-C6 alkylene groups which may be substituted with ether, hydroxyl and combinations thereof.

49. The silicone hydrogel of claim 43 wherein $R_{13}$ is selected from C1 or C3-C6 alkylene groups which may be substituted with ether, hydroxyl and combinations thereof.

50. The silicone hydrogel of claim 43 wherein a is 5 to 15.

51. The silicone hydrogel of claim 43 wherein $R_{16}$ is H or methyl.

52. The silicone hydrogel of claim 43 wherein said monomethacryloxyalkylpolydimethylsiloxane methacrylate is selected from the group consisting of monomethacryloxypropyl terminated mono-n-butyl terminated polydimethylsiloxane, monomethacryloxypropyl terminated mono-n-methyl terminated polydimethylsiloxane, monomethacryloxypropyl terminated mono-n-butyl terminated polydiethylsiloxane, monomethacryloxypropyl terminated mono-n-methyl terminated polydiethylsiloxane, N-(2,3-dihydroxypropane)-N'-(propyl tetra(dimethylsiloxy)dimethylbutylsilane)acrylamide, α-(2-hydroxy-1-methacryloxypropyloxypropyl)-ω-butyl-octamethylpentasiloxane, and mixtures thereof.

53. The silicone hydrogel of claim 43 wherein said monomethacryloxyalkylpolydimethylsiloxane methacrylate is selected from the group consisting of monomethacryloxypropyl terminated mono-n-butyl terminated polydimethylsiloxane, monomethacryloxypropyl terminated mono-n-methyl terminated polydimethylsiloxane, N-(2,3-dihydroxypropane)-N'-(propyl tetra(dimethylsiloxy)dimethylbutylsilane)acrylamide, and mixtures thereof.

54. The silicone hydrogel of claim 35 wherein said slow reacting hydrophilic monomer and said hydroxyl monomer form a molar ratio of hydroxyl groups to the slow-reacting hydrophilic monomer of between about 0.15 and about 0.4.

55. The silicone hydrogel of claim 1 further comprising at least one crosslinking monomer.

56. The silicone hydrogel of claim 1 wherein said slow-reacting hydrophilic monomer is selected from N-vinylpyrrolidone, N-vinylacetamide, 1-methyl-3-methylene-2-pyrrolidone, 1-methyl-5-methylene-2-pyrrolidone, 5-methyl-3-methylene-2-pyrrolidone, and mixtures thereof.

57. The silicone hydrogel of claim 1 wherein said photoinitiator is a visible light initiator.

58. The silicone hydrogel of claim 1 further comprising an advancing contact angle of less than about 80°.

59. The silicone hydrogel of claim 1 further comprising an advancing contact angle of less than about 70°.

60. The silicone hydrogel of claim 1 further comprising from about 5 to about 20 wt % of at least one polar diluent, based upon all components in the reaction mixture.

61. The silicone hydrogel of claim 60 wherein said diluent further comprises at least polyhydric codiluent.

62. The silicone hydrogel of claim 61 wherein said polyhydric codiluent is present in an amount between about 0.5 and 5 wt %, based upon all components in the reaction mixture.

63. The silicone hydrogel of claim 60 wherein said polar diluent is selected from the group consisting of carboxylic acids, secondary and tertiary alcohols.

64. The silicone hydrogel of claim 60 wherein said polyhydric codiluent is selected from the group consisting of glycerin, boric acid, boric acid glycerol esters, polyalkylene glycols and mixtures thereof.

65. The silicone hydrogel of claim 60 wherein said polar diluent further comprises up to about 3 wt % of at least one lactam polymer or copolymer.

66. The silicone hydrogel of claim 1 wherein said reaction mixture further comprises at least one slow reacting crosslinker and at least one fast reacting crosslinker.

67. The silicone hydrogel of claim 66 wherein said slow reacting crosslinkers have only vinyl reactive functionality and said fast reacting crosslinkers have (meth)acrylate reactive functionality only.

68. The silicone hydrogel of claim 66 wherein said slow reacting crosslinker comprises TAO and said fast reacting crosslinker is selected from the group consisting of EDGMA, TEGDMA and mixtures thereof.

69. The silicone hydrogel of claim 1 wherein said reaction mixture is substantially free from additional hydrophilic components.

70. The silicone hydrogel of claim 60 wherein said reaction mixture comprises less than about 5% of intermediate reacting hydrophilic components.

71. The silicone hydrogel of claim 67 wherein said at least one slow reacting crosslinker and at least one fast reacting crosslinker are each present in said reaction mixture in amounts between about 0.05 to about 0.3 wt %.

72. The silicone hydrogel of claim 67 wherein said at least one slow reacting crosslinker and at least one fast reacting crosslinker are each present in said reaction mixture in amounts between about 0.1 to about 0.2 wt %.

73. The silicone hydrogel of claim 67 wherein all crosslinkers are present in an amount less than about 0.5 wt %.

74. The silicone hydrogel of claim 12 wherein said at least one UV absorbing compound is reactive.

75. The silicone hydrogel of claim 1 wherein said reactive mixture further comprises at least one additional hydrophilic monomer, provided that if said at least one hydrophilic monomer has a kinetic half life between 120% and 170% of said silicone-containing component kinetic half life, said additional hydrophilic monomer is present in a concentration which provides said silicone hydrogel with a contact angle less than about 80°.

76. The silicone hydrogel of claim 75 wherein said at least one hydrophilic monomer has a kinetic half life between 120% and 170% of said silicone-containing component kinetic half life, and said reactive mixture comprises less than about 3 weight % said additional hydrophilic monomer.

* * * * *

UNITED STATES PATENT AND TRADEMARK OFFICE
CERTIFICATE OF CORRECTION

PATENT NO. : 8,937,110 B2  
APPLICATION NO. : 13/720218  
DATED : January 20, 2015  
INVENTOR(S) : Alli et al.

Page 1 of 1

It is certified that error appears in the above-identified patent and that said Letters Patent is hereby corrected as shown below:

In the Claims

Column 62, claim 28, line 58  
Correct "$R_5$"  
To read -- $R_6$ --

Column 66, claim 68, line 18  
Correct "reacting crosslinker comprises TAO"  
To read -- reading crosslinker comprises TAC --

Signed and Sealed this  
Fifth Day of May, 2015

Michelle K. Lee  
*Director of the United States Patent and Trademark Office*